US011927571B2

(12) United States Patent
Smith

(10) Patent No.: US 11,927,571 B2
(45) Date of Patent: *Mar. 12, 2024

(54) METHODS AND DEVICES FOR EVALUATING THE CONTENTS OF MATERIALS

(71) Applicant: Michael P. Smith, Tulsa, OK (US)

(72) Inventor: Michael P. Smith, Tulsa, OK (US)

(*) Notice: Subject to any disclaimer, the term of this patent is extended or adjusted under 35 U.S.C. 154(b) by 266 days.

This patent is subject to a terminal disclaimer.

(21) Appl. No.: 17/548,295

(22) Filed: Dec. 10, 2021

(65) Prior Publication Data

US 2023/0184645 A1 Jun. 15, 2023

Related U.S. Application Data

(63) Continuation of application No. 16/654,018, filed on Oct. 16, 2019, now Pat. No. 11,280,186, which is a
(Continued)

(51) Int. Cl.
*G01N 3/08* (2006.01)
*G01N 33/24* (2006.01)
(Continued)

(52) U.S. Cl.
CPC ............ *G01N 3/08* (2013.01); *G01N 33/241* (2013.01); *G01N 2203/0019* (2013.01); *G01N 2203/0076* (2013.01)

(58) Field of Classification Search
CPC .................. G01N 3/08; G01N 33/241; G01N 2203/0019; G01N 2203/0076;
(Continued)

(56) References Cited

U.S. PATENT DOCUMENTS 4,495,414 A 1/1985 Barrie
4,525,328 A 6/1985 Bredeweg
(Continued)

FOREIGN PATENT DOCUMENTS

CA 2068012 12/1992
CN 1609586 4/2005
(Continued)

OTHER PUBLICATIONS

Mazidi, et al. "Measurement of Uniaxal Compressive Strength of Rocks Using Reconstructed Cores from Rock Cuttings", Journal of Petroleum Science and Engineering 86-87 (2012) 39-43.
(Continued)

*Primary Examiner* — Herbert K Roberts
*Assistant Examiner* — Anthony W Megna Fuentes
(74) *Attorney, Agent, or Firm* — Transformative Legal LLC; Len S. Smith

(57) ABSTRACT

Methods for determining the hardness and/or ductility of a material by compression of the material are provided as a first aspect of the invention. Typically, compression is performed on multiple sides of a geologic material sample in a contemporaneous manner. Devices and systems for performing such methods also are provided. These methods, devices, and systems can be combined with additional methods, devices, and systems of the invention that provide for the analysis of compounds contained in such samples, which can indicate the presence of valuable materials, such as petroleum-associated hydrocarbons. Alternatively, these additional methods, devices, and systems can also stand independently of the methods, devices, and systems for analyzing ductility and/or hardness of materials.

13 Claims, 23 Drawing Sheets

Related U.S. Application Data continuation of application No. 16/019,523, filed on Jun. 26, 2018, now Pat. No. 10,494,919, which is a continuation of application No. PCT/US2017/065921, filed on Dec. 12, 2017.

(60) Provisional application No. 62/434,399, filed on Dec. 14, 2016.

(51) Int. Cl.
    *G01N 1/28* (2006.01)
    *G01N 1/40* (2006.01)

(58) Field of Classification Search
    CPC ........... G01N 1/286; G01N 2001/4033; G01N 1/4022; G01N 33/24; G01N 3/12; G01N 3/40; G01N 1/24; G01N 2015/1043; G01N 33/6848; E21B 49/005; E21B 49/02; E21B 43/26; E21B 49/08; E21B 49/081; H01J 49/0422; H01J 49/26; H01J 49/0409; H01J 49/0468; H01J 49/00; B27K 5/0005; B29B 17/0408; G01M 3/202

See application file for complete search history.

(56) References Cited

U.S. PATENT DOCUMENTS

| | | |
|---|---|---|
| 4,797,906 A | 1/1989 | Smith |
| 4,960,567 A | 10/1990 | Smith |
| 5,241,859 A | 9/1993 | Smith |
| 5,286,651 A | 2/1994 | Smith |
| 5,328,849 A | 7/1994 | Smith |
| 5,341,859 A | 8/1994 | Howseman, Jr. |
| 5,411,707 A | 5/1995 | Hiatt |
| 5,416,024 A | 5/1995 | Smith |
| 5,447,556 A | 9/1995 | Pleil |
| 5,457,316 A | 10/1995 | Cohen |
| 5,767,399 A | 6/1998 | Smith |
| 6,541,272 B1 | 4/2003 | Mitra |
| 6,661,000 B2 | 12/2003 | Smith |
| 6,743,397 B1 | 6/2004 | Zesiger |
| 7,210,342 B1 | 5/2007 | Sterner |
| 7,395,691 B2 | 7/2008 | Sterner |
| 8,256,282 B2 | 9/2012 | Schlachter |
| 8,536,524 B2 | 9/2013 | Pomerantz |
| 2001/0015093 A1 | 8/2001 | Kempe |
| 2002/0194896 A1 | 12/2002 | Stolper |
| 2004/0099804 A1 | 5/2004 | Lui |
| 2005/0109207 A1 | 5/2005 | Olander |
| 2005/0194134 A1 | 9/2005 | McGregor |
| 2010/0277724 A1 | 11/2010 | Bounouar |
| 2011/0305309 A1 | 12/2011 | Brown |
| 2012/0167786 A1 | 7/2012 | Laugham, Jr. |
| 2012/0186331 A1 | 7/2012 | Tipler |
| 2014/0026638 A1 | 1/2014 | Bowers, II |
| 2014/0220700 A1 | 8/2014 | Alexander |
| 2014/0283580 A1 | 9/2014 | Rouchon |
| 2015/0123670 A1 | 5/2015 | Robbat, Jr. |
| 2015/0167052 A1 | 6/2015 | Griffin |
| 2015/0346179 A1 | 12/2015 | Pillot |
| 2016/0222781 A1 | 8/2016 | Lawson |

FOREIGN PATENT DOCUMENTS

| | | |
|---|---|---|
| CN | 104407089 | 3/2015 |
| EP | 0414564 | 2/1991 |
| WO | 2003050844 | 6/2003 |
| WO | 2015050832 | 4/2015 |
| WO | 2016086689 | 11/2016 |

OTHER PUBLICATIONS

International Search Report for PCT/US2017/065921 dated Apr. 6, 2018.

Non-Final Office Action for U.S. Appl. No. 15/908,760 dated May 17, 2018.

Russian Office Action for Application No. 201991461 dated Aug. 19, 2020 including translation.

Jorge, et al., "Analysis of Volatiles in Fluid Inclusions by Direct Online Crushing Mass Spectrometry", Journal of Brazilian Chemical Society 22.3, dated 2011: 43-455, p. 445, col. 1.

Mccarthy, et al., "Basic Petroleum Geochemistry for Source Rock Evaluation", Oilfield Review, 23.2, dated Jun. 2011.

International Search and Written Opinion for PCT/US2019/22362 dated Aug. 5, 2019.

Indian Examination Report dated May 16, 2021 for Application No. 201917021802.

Extended European International Search Report for EP 17880886 dated Jul. 30, 2020.

METHODS AND DEVICES FOR EVALUATING THE CONTENTS OF MATERIALS

PRIORITY AND REFERENCES TO RELATED APPLICATIONS

This application is a continuation of U.S. application Ser. No. 16/654,018, filed Oct. 16, 2019, now allowed, which is a continuation of U.S. application Ser. No. 16/019,523, filed Jun. 26, 2018, now patented (U.S. Pat. No. 10,494,919), which is a continuation of PCT/US2017/065921, filed Dec. 12, 2017, which claims the benefit of U.S. Provisional Application No. 62/434,399, filed Dec. 14, 2016, all of which patent applications and patents have the same title as this disclosure and are hereby incorporated by reference. U.S. application Ser. Nos. 15/908,760 and 16/019,529, which also independently claim the benefit of priority to PCT/US2017/065921 are also now patented (as U.S. Pat. Nos. 10,190,413 and 10,260,336, respectively).

FIELD OF THE INVENTION

This invention pertains to novel methods of evaluating the contents of materials, including, for example, volatile substances such as petroleum-related hydrocarbons in geological materials, as well as devices that can be used in the practice of the methods and other applications.

BACKGROUND OF THE INVENTION

Human evaluation of the content of materials has probably been practiced for longer than any written records. However, the ability to use information associated with a material to understand the properties of associated materials, such as surrounding geologic formations, has been largely developed in the last 100 years, beginning with the Schlumberger brothers' discovery that electric resistivity could be used to evaluate the structure and likely content of geologic structures, and thus provide a mechanism for finding subsurface materials, such as fossil fuel deposits. While a significant advance, resistivity has proven to be of limited utility, especially in modern times in which easy to find petroleum and natural gas deposits are increasingly more difficult to detect with such technology.

Prior technology involving the analysis of rock materials, such as to determine the presence of hydrocarbons in a geologic formation, have focused on the analysis of material in fluid inclusions. Fluid inclusions are often characterized as "bubbles" of fluid trapped within a host material, such as rock. These compartments within rock or other material are usually very small, from 1 to 20 microns across. Fluid inclusions are characterized by being completely sealed and isolated from the environment, typically over very long periods of time (on a geologic scale—e.g., over millions of years). The contents of fluid inclusions are believed to be the remnants of the exact fluid associated with the rock material at formation. As such, the content of inclusions can provide information about the fluid composition, temperature and pressure at which a material was formed and what it may contain.

In one type of typical fluid inclusion analyses, a rock sample, usually from a sedimentary rock, is crushed under strong vacuum and the trapped fluids that are released from the crushing are analyzed, such as with a mass spectrometer. Prior to my inventions described herein, the conditions under which mass spectrometers operate have dictated how the devices and methods for fluid inclusion analysis have been performed. Fluid inclusion materials have shown some usefulness in the discovery of hydrocarbon materials and today is a commonly practiced method performed on materials obtained from oil well drilling. However, fluid inclusion analysis also is of limited utility due to a number of issues, such as the content of the inclusion often not matching the present-day fluids in the geologic formation.

Specific patents describing my prior inventions, the inventions of my co-inventors, and other inventors include U.S. Pat. No. 4,960,567, which relates to a method for obtaining gasses from fluid inclusions for analysis through mass spectrometry and U.S. Pat. No. 5,241,859, which describes a method in which material from a collection of fluid inclusions are analyzed to identify collections that are rich in hydrocarbons, which can then be further analyzed, such as through mass spectrometry analysis. U.S. Pat. No. 5,328,849 describes methods for mapping subsurface formations by analyzing fluid inclusions in several samples through specialized devices I also invented.

U.S. Pat. No. 6,661,000 describes an invention made by me and my co-inventors wherein we invented a method for analyzing surface and pore liquids, as opposed to fluid inclusions, by a method in which cuttings or other samples are subjected directly to mass spectrometry analysis under high vacuum. However, one of the shortcomings with that method is the loss of gasses associated with the sample due to the need to apply such relatively high vacuum levels in order to make the devices we invented operate.

The invention provides methods and devices that not only address the limitations of these prior inventions but also greatly expand on them in terms of the applicability of methods to various materials and associated materials, extending well beyond simple analysis of potential hydrocarbon-associated rock samples. These and other advantages of the invention, as well as additional inventive features, will be apparent from the description of the invention provided herein.

SUMMARY OF THE INVENTION

In a first aspect, the invention provides new methods for determining the ability to subject a geologic material to fracking and similar processes in which the hardness and/or ductility of a material is determined by compression of one or more samples of the material, especially on multiple sides of the sample in a contemporaneous manner. The sample is typically associated with a drill operation and often is a cutting. The methods typically comprise analysis of many samples, such as 5, 10, 15, 20, 30, 40, 50, or more samples (e.g., 100, 250, 500, 750, 1,000, 1,250, 1,500, or more samples), usually from different locations with respect to most of the other analyzed samples (such as being separated by at least 0.75 vertical and/or horizontal feet). The invention further provides devices and systems for performing such methods of the first aspect.

These methods, devices, and systems can be combined with additional methods, devices, and systems of the invention that provide for the analysis of volatile substances contained in such samples, such as cuttings, which can indicate the presence of substances in the material associated with the sample, such as petroleum-associated hydrocarbons (oil and/or gas). Alternatively, such additional methods, devices, and systems can also stand independently of the methods, devices, and systems for analyzing ductility and/or hardness of materials of the first aspect of the invention, as a second, independent aspect of the invention. The method of the second aspect typically comprises exposing the samples to one or more forces that allow or promote the release of the volatile substances, capturing the volatile substances, and then analyzing the volatile substances, so as to identify the nature of the composition of the material. Such methods often comprise application of a gentle force, such as a gentle vacuum step (e.g., at about 10-about 100 millibars), which allows for capture of volatile fluids in the sample without significant loss of such materials in the analytical method.

DETAILED DESCRIPTION OF THE INVENTION

Figure 1:
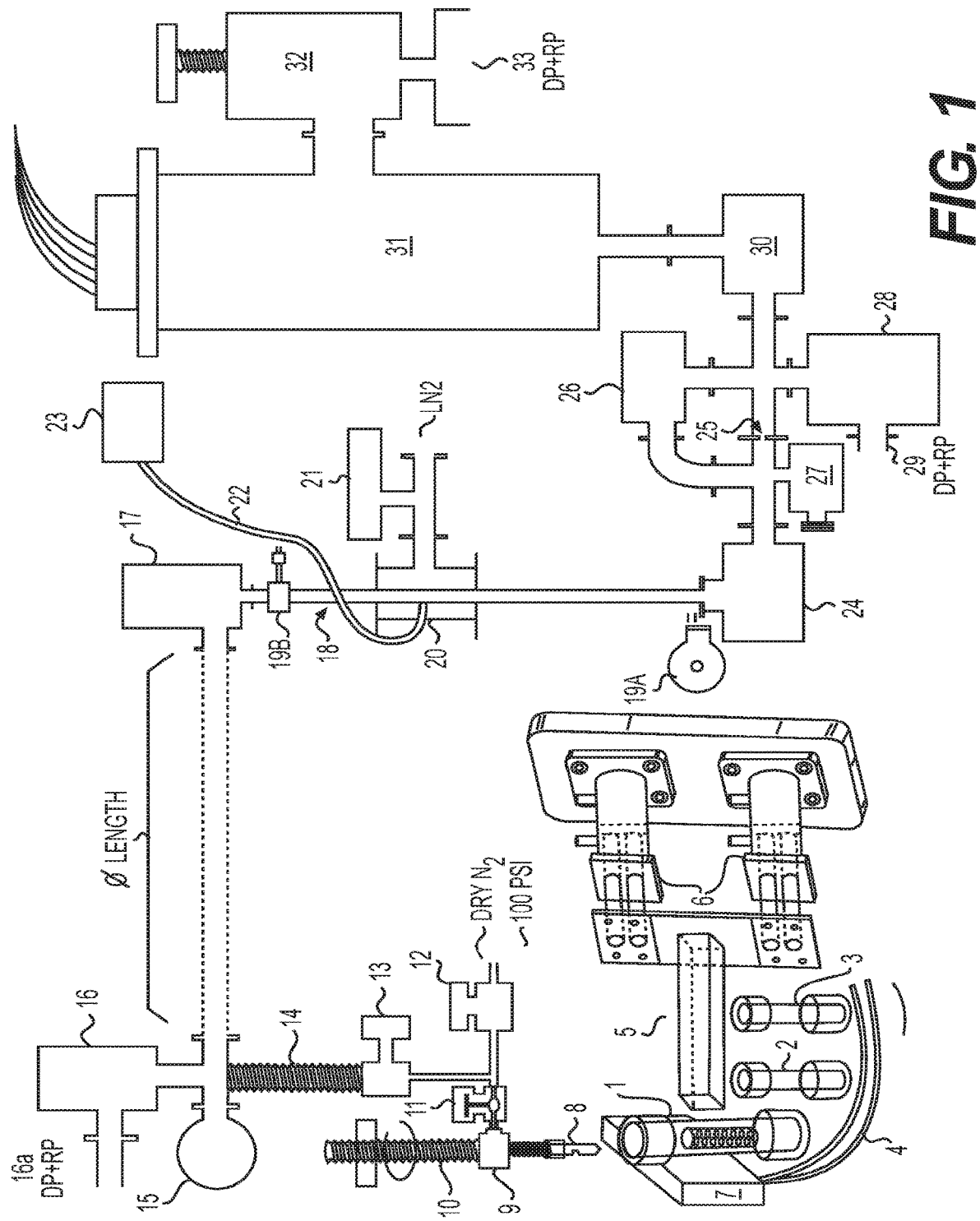
FIG. 1 is a representation of an illustrative device/system of the invention for analyzing both the compressibility of samples and the volatile substance content of such samples through a non-selective trap of condensable gasses, a separate trap of non-condensable gasses, and mass spectrometry analysis of such compounds.

The invention described herein provides various types of devices and methods for analyzing the contents of hard mineral-based materials, such as rock samples taken from geologic formations. One key use of these methods and devices is the analysis of the drill cuttings from petroleum wells for the contents of certain compounds in such cuttings or that can be obtained from such cuttings, which in turn provide information about the geologic material associated with the cuttings. However, the methods and devices of the invention are not limited to such applications and settings and can be applied to other settings, as will be discussed further herein.

In a primary aspect, the invention described herein provides a method for analyzing volatile substances in a material comprising the steps of (a) providing an analyzable sample of a material containing an analyzable amount of one or more volatile substances, (b) permitting the release of fluid (e.g., gas) containing the volatile substances from the material, (c) optionally subjecting the sample to one or more forces to aid in the release of the fluid, (e) optionally trapping the fluid by contact with a media, in an analyzable amount (an aliquot), (d) optionally isolating the fluid from the material, (e1) applying energy or one or more forces to the aliquot so as to cause volatile compounds in the aliquot, if present, to form other chemical substances (energy-treated gas(ses)) in a predictable manner and/or (e2) releasing volatile substances from the aliquot as trap-released fluids in a predictable sequence, and (f) analyzing the chemistry of one or more trap-released fluids and/or energy-treated fluids.

The inventive methods described herein can be practiced with any suitable material containing any suitable number and/or suitable number of any suitable type of volatile substances. Suitability in this respect means that the volatile substances are amenable to analysis by the methods and/or devices of the invention, which can be determined by the principles described here or through application of routine experimentation. A volatile substance in the context of the invention is a material that will take the form of a gas under the conditions in which the method is performed. Conditions relevant to whether a material is in the form of a gas at a particular time include the pressure the material is under at the time. In one aspect of the invention, at least one volatile substance is released from the material at atmospheric pressure. In another aspect, at least one volatile material analyzed by the method is released from the material under a vacuum (a pressure lower than atmospheric pressure—i.e., a pressure of less than about 760 Torr or $1.013 \times 10^5$ Pa) or significantly more of the material is released under a vacuum than at atmospheric pressure (such as at least about 2 times, at least about 3 times, at least about 5 times, at least about 10 times, at least about 20 times, at least about 30 times, at least about 50 times, or at least about 100 times atmospheric pressure).

In a particular aspect, the method includes analyzing at least one volatile substance that is released from the material under low vacuum conditions. Low vacuum conditions mean pressure conditions ranging from about 760 to about 25 Torr or $1 \times 10^5$ to $3 \times 10^3$ Pa (in this document each disclosure of a quantity modified by modifiers such as "about" is to be construed as simultaneously providing the corresponding exact disclosure and each disclosure of a range is to be construed as disclosing each unit of the same order of magnitude as the end points of the range, e.g., a disclosure of the range of 1-5 also is to be construed as disclosing the numbers 1, 2, 3, 4, and 5 individually). In another exemplary aspect, the method includes the step of analyzing at least one volatile substance that is released at under but close to 1000 millibars, such as about 40 millibars to about 950 millibars, e.g., about 50 millibars to about 900 millibars, about 100 millibars to about 800 millibars, such as about 150 millibars to about 750 millibars, or any combination of such low and high-end points.

In another context, the method also or alternatively includes analyzing at least one volatile substance that is released from the material under medium vacuum conditions. Medium vacuum conditions mean pressures of about 25 Torr to about $1 \times 10^{-3}$ Torr ($3 \times 10^3$ to $1 \times 10^{-1}$ Pa). In another aspect, the method includes analyzing at least one volatile substance that is released from the material under a pressure of about 50 millibars (e.g., applying one more pressures of about 20-80 millibars, such as about 30-70 millibars) and still another aspect the method comprises performing an analysis on an aliquot obtained by extraction at one or more pressures in the range of about 30 millibars to about 10 millibars, such as about 25 millibars to about 12 millibars, e.g., about 20 millibars to about 15 millibars, or any other combination of such low and high end points.

In another aspect, the invention also includes analyzing at least one volatile substance that is released from the material under high vacuum conditions. High vacuum conditions mean about $1 \times 10^{-3}$ to about $1 \times 10^{-9}$ Torr ($1 \times 10^{-1}$ to $1 \times 10^{-7}$ Pa). In another respect, the invention includes analyzing at least one volatile substance released under vacuum pressures of less than about 5 millibars, such as less than about 2 millibars, such as less than 1 millibar. For example, in another aspect, the invention comprises analyzing at least one volatile substance released under vacuum pressures of about $1 \times 10^{-2}$ millibars or less, such as about $1 \times 10^{-3}$ to about $1 \times 10^{-9}$ millibars.

In still other aspects of the invention, the method does not comprise application of high vacuum (such as those described above), which in one respect distinguishes such aspects of this invention from prior art methods which include or are dependent upon the application of high vacuum to perform analysis of materials. In still other aspects, the practice of the method of the invention lacks application of either any high vacuum or any medium vacuum in the release of volatile compounds. This distinguishes these aspects, among other things, from prior art methods, such as many forms of fluid inclusion analysis, which typically require application of high vacuum and/or medium vacuum.

The material also can be any material which can be suitably subjected to the methods of the invention. In one typical context the material is a geologic material, such as rock material, a mud, or a soil, or a drilling byproduct, especially drilling mud or a drill cutting. In the context of this invention terms such as "cuttings" and "drill cuttings' means rock fragments that are brought to the surface in a drilling operation (such terms are generally understood in the art). Typically, drill cuttings are rocks that are maintained separated from drill muds in a shaker table operation or similar separation process. Drill cuttings can have any suitable size. The size of cuttings produced at a well will depend on several factors including the geologic material being drilled through and the drill bit used, with more modern drill bits often forming smaller cuttings. Particle sizes of cuttings can be, for example, as small as about 5 microns (e.g., about 10 microns or larger, about 20 microns or larger, about 25 microns or larger, about 50 microns or larger, etc.), but typically the cuttings will have particle sizes of at least about 100 microns, such as at least about 150 microns, or at least about 200 microns (e.g., about 250 microns or greater), and may be significantly larger, such as up to about 7.5 mm (e.g., about 6.5 mm or less, about 6 mm or less, or about 5 mm or less). Commonly, cuttings that typically have a particle size of between about 0.5 mm to about 1 mm and about 5 mm to about 6 mm are used in methods of the invention. However, in a particularly unexpected aspect of the invention (as exemplified elsewhere herein) the method has been performed using very small cuttings that were produced in a coring process, which are significantly smaller in size than typical cuttings obtained in oil production or exploration. Thus, for example, the method can be performed with cuttings of about 100 microns to about 5 mm, about 50 microns to about 10 mm, about 25 microns to about 7 mm, about 25 microns to about 12.5 mm, about 50 microns to about 6.5 mm, about 0.2 mm to about 6 mm, about 0.25 mm to about 5 mm, or about 0.5 mm to about 5 mm. These are exemplary ranges, and these end-points of any one of these ranges can be interchanged with end points of any other range to create other suitable ranges in which to focus other exemplary methods of the invention.

"Drilling mud", "muds", or "drilling fluid" in the context of this invention refers to a material that is distinguished from cuttings. Drilling mud is material that is at least initially introduced to a well site and used by the operator of a drilling operation to perform one or more functions including providing hydrostatic pressure to prevent formation fluids from entering into the well bore, maintaining the temperature and/or "cleanliness" of the drill bit (or at least preventing overheating and/or obstruction), maintaining the structural integrity of the bore hole, and/or aiding in the carrying out of drill cuttings. Drilling muds commonly will contain materials such as bentonite, barite, or hematite and can be water-based or oil-based. Muds often are dense materials and thixotropic, meaning that they become more fluid with application of agitation. The nature of drilling muds and the differences between drilling muds and cuttings will be understood by those skilled in the art.

In a specific context, the material is rock or mud material that is associated with either exploratory drilling or production drilling for petroleum, natural gas, or related materials, however materials obtained from other activities such as exploratory and production drilling for economic mineral deposits and geothermal energy also or alternatively could be used in practicing the methods of the invention. The material also or alternatively can be from other sources than from natural geologic formations or other non-petroleum-related geologic samples, or even biological samples such as teeth, bones, and the like (e.g., food or biomass from any type of living organism whether viable or non-viable). In this respect, the methods of the invention may have application in various forensic and/or intelligence applications, for determining the impact of processes on materials, the historical source or modulation of materials, and/or, for example, the origin of materials or other information about the nature of such materials. For example, in another context the material is construction material, such as material used in building of commercial buildings, bridges, roads, construction sites, antiquities, and the like. The methods also can be applied to other man-made materials such as ceramics and other types of materials used in the manufacture or construction of other devices and structures, such as semiconductors.

In one aspect of the invention, the samples selected for analysis in the performance of the method comprise, are substantially comprised of (i.e., more than about 20% of the samples are), are primarily comprised of (i.e., more than 51% of the samples are), consist essentially of (are comprised of to a level that the amount of non-conforming material does not impact the nature of the total sample or sample set), or consist entirely of, material that substantially lack relevant fluid inclusions ("RFIs"). "Relevant fluid inclusions" or "RFIs" in the context of this invention refers to fluid inclusions that (1) contain one or more materials that are indicative of the presence of a substance in the material (at least in the inclusions), such as petroleum or petroleum-related substances (e.g., organic acids, hydrocarbons, and the like, such as acetic acid) and (2) the presence of such materials reflect the present condition of the material (in terms of the presence of the target substance). Samples may lack relevant fluid inclusions for a number of reasons, such as relevant fluid inclusions may have never formed in the material (e.g., shallow, unconsolidated, young sandstone oil reservoirs in the Gulf of Mexico) or the relevant fluid inclusions may have been destroyed by natural and/or human processes (e.g., meteorite impact or drilling with polycrystalline diamond compact ("PDC") drill bits). As indicated elsewhere, often fluid inclusions will contain ancient fluids that often do not reflect the present fluid content of the material. In certain cases, relatively "young" fluid inclusions can form in a material or older fluid inclusions may be filled by relatively "young" material that is present in a material. Such fluid inclusions can be classified as RFIs. Non-relevant fluid inclusions ("NFIs") may still provide relevant information to understanding the material, but they are less probative with respect to the fluid content of the material than RFIs. Substantially lacking RFIs means that less than 0.000005% of the volume of the sample is made up of target substance (e.g., petroleum) or target substance-related fluid inclusions (e.g., only about 0.05 ppm or less of the sample volume is made up of oil or an oil-relevant substance). In some cases the invention is practiced wherein the amount of RFIs is even less, such as 0.025 ppm or less, about 0.02 ppm or less, or even about 0.01 ppm or less of the volume of the sample is made up of target substance-containing or target substance-relevant fluids (in even further aspects the amount of RFIs in the sample is even less such as about 20 parts per trillion of the volume of the sample or less, about 10 parts per trillion of the volume of the sample or less, about 5 parts per trillion of the volume of the sample or less, or even about 1 parts per trillion of the volume of the sample or less. In still other aspects, the sample or some of the sample(s) analyzed contain no detectable amount of RFI. In some cases, the sample may contain more volume of fluid inclusions, however the fluid inclusions will be known to not be relevant in the sense that there is information that informs the artisan that material in the fluid inclusion is not indicative of the fluid content of the material (e.g., the inclusion is indicative of the presence of oil, but it is known from drilling that the content of the material reflects little to no oil being present in the material). In certain aspects, the material and/or the sample is or comprises a material that lacks materials that will form a sufficient amount, size, or type of inclusion to be relevant, such as many shales or unconsolidated/young sands, which commonly lack material that is hard enough to sufficiently form inclusions that can provide detectable levels of RFIs even if the target substance is present in the material. It is important to understand that the term "target" in this and other contexts of describing aspects of the invention can mean, but does not always mean, a specific substance that is expected to be present or that is sought by the analytical methods of the invention. Thus, for example, the "target" can be one or more unknown materials that are in a material, such as one or more unknown substances that are included in drill cuttings or other geologic material but that have no known composition prior to the analysis.

In another aspect of the invention, the samples analyzed and/or the material comprise a low number of RFIs. For example, in a particular facet of the invention the sample is a collection of cuttings in which less than about 20%, less than about 15%, or about 10% or less, such as about 5% or less of the cuttings comprise RFIs.

In other aspects, materials or samples with fluid inclusions can be included intentionally and will be included commonly in the sample and/or material, and, in such cases, the method optionally can additionally comprise, as discussed below, performance of other methods on materials containing fluid inclusions taken from site and/or included in the samples.

The material and/or samples typically will include fissures, fractures, pockets, cracks, etc., which contain target materials of interest, such as volatile hydrocarbons. Such fissures, fractures, etc. (referred collectively herein as "target substance pores" or "TSPs"), will often desirably contain target substance or target substance-relevant material (e.g., such as organic acids and/or hydrocarbons that are indicative of the presence of petroleum) that also in some cases are (1) present in relevant amounts in the material (either in fluid form or are absorbed or adsorbed in the material), rather than material that are artifacts of prior existing conditions, as is the case with many NFIs, (2) are exposed to the surrounding environment in some amount (such as by being contained in a pore in the material that is exposed to the surrounding environment) (in other words are not completely sealed off from the environment as is the case with fluid inclusions), or (3) can be characterized in satisfying both (1) and (2). A "pore fluid" in the context of this invention means a substance that is ordinarily liquid or gas in association with the material, contains one or more volatiles, and is found in a TSP and satisfies conditions (1), (2), or (3) of the preceding sentence. In some aspects, the invention is characterized by analyzing one or more samples containing an analyzable amount of pore fluid(s) and/or by analyzing one or more samples containing an analyzable amount of a pore fluid-related substance.

In a set of particular aspects, the material consists of, comprises, or is substantially comprised of a geologic material that has not experienced significant enough burial diagenesis to have formed fluid inclusions. "Substantially comprised of" in the context of this invention means that a substantially majority, such as at least 65%, more often at least 75%, such as at least 80%, at least 85%, at least 90%, or even at least 95% of the referenced material or composition is comprised of the component at issue. In particular aspects, the material consists of, is comprised of, or is substantially comprised of "young sands." In the context of this invention a "young sand" means recent, Pliocene, and Miocene-age sediments (e.g., 0-5 million years of age). For such sands that are buried about 10,000 feet below surface level or less in a tectonically quiet area (an area with relatively few earthquakes), RFIs will typically not be present or will be substantially lacking, as described elsewhere herein.

In yet another aspect, the sample and material comprise a "tight carbonate" material. A "tight carbonate" in the context of the inventive methods means a material that comprises a substantial carbonate portion (e.g., at least about 90% of the material is comprised of one or more carbonates), which exhibit low permeability (e.g., about 15 millidarcies or less, about 10 millidarcies or less, or about 5 millidarcies or less). In one aspect, the material is a material that is not suitable for traditional $S_W$ analysis, because electricity cannot sufficiently flow through the material to give proper signals required for traditional resistivity-based $S_W$ analysis. The methods of the invention also or alternatively can be applied to similar types of materials from other settings that have similar types of resistivity, permeability, and/or conductivity issues.

The material typically is obtained in an analyzable sample or presented in an analyzable sample. In a general sense, an analyzable sample can be any sample that has the necessary characteristics that allow it to be analyzed using the specific conditions of the inventive method to be practiced with the material. Skilled persons practicing this invention will be able to select such materials based on the other conditions of the method, the teachings provided here, especially in view of routine experimentation and other known principles. For example, the size of the sample must be of sufficient size to provide enough material to be analyzed. Additionally, the sample typically is handled in a way so as to preserve material in the sample to allow volatile substances to be released therefrom upon application of the force(s) to be applied in performing the method of the invention. Other conditions and features of collection, storage, and/or handling of the sample may be selected so as to maintain the structural and/or chemical stability of the sample and volatile compounds contained therein. The sample also typically should be sufficiently free of materials that might interfere with the analysis. For example, the sample typically is collected and maintained in a manner such that it is substantially free of material from other sources that might "contaminate" the sample by causing it to provide false information about the location it is taken from and its contents.

In still another aspect of the invention, the sample is obtained from a process that comprises the use of an oil-based mud. In general, drilling muds may be water-based or oil-based. Oil-based muds often can create difficulties for analytical methods such as fluid inclusion analysis methods known in the prior art. Those methods typically require application of high heat and/or vacuum, such as, e.g., in a vacuum oven, applied over a long period in order to deal with samples obtained with oil-based mud drilling processes or risk interference from the oil base of the mud and/or the oil material used for washing the samples. Such problems also exist with respect to non-fluid inclusion analysis methods, such as my other prior inventions. Methods in which high temperature and/or vacuum is/are applied to remove oil-based muds can suffer from the problem of also removing any endogenous hydrocarbons, organic acids, and/or oil. The ability to analyze such samples with the methods of the invention is yet another advantageous aspect of the inventive methods described herein. Samples also or alternatively can be obtained from water-based mud drilling operations, and in some instances (as exemplified herein) samples can be obtained for a site that was subject to both oil-based mud drilling and water-based mud drilling.

As discussed elsewhere herein, samples may be sealed at or soon following collection. In such aspects, about 0.5% to about 5% of the volume of the sample may be made up of the target substance or target-related substance. For example, about 0.75%-about 3.5%, such as about 0.8% to about 3%, about 0.9% to about 2.75%, or about 1% to about 2.5% of the volume of the sample may be made up of the target substance(s) (e.g., C5-C10 petroleum hydrocarbons) and/or target substance-related materials. These amounts of target-related substances are typically higher than the amount than would be found in in materials only having such target substances or target substance-related materials in fluid inclusions.

The amount of material collected or provided may be in excess of the amount that can be the subject of analysis at any time so as to provide assurance that there will be enough of the sample material to perform repeated runs of the method, etc. Any suitable amount of material can be used. A typical sample may be on the order of about 100 mg, but may be as low as about 1 mg, about 10 mg, about 25 mg, about 50 mg, or about 75 mg. The maximum size of the sample often is determined by either the sample container size and/or the capacity of the mass spectrometry analytical component of the device used in the method, if present. However, under the right conditions and using the right type of device samples as large as 1 g, 5 g, 10 g or even larger may be suitable for analysis.

Typically, the sample will be collected from a material having a relatively known location. The location usually will include approximate depth information in addition to longitude and latitude coordinates. Often the location may be a site of interest in petroleum or mineral exploration, such as an expected or known oil well, an oil well that has been previously deemed non-productive, or a mineral mine, such as a gold mine.

In another aspect of the invention the sample is a fragment of a core sample. Core samples are commonly generated in oil exploration and related processes and are well understood in the art. Analysis of core samples is considered important because of the preservation of oil or other target substances in the material. However, the process of analyzing core samples is often very time intensive. Advantageously, methods of the invention can be used to, e.g., to analyze fragments of core samples much more rapidly by, for example, evaluating the hydrocarbon content of such core sample fragments.

In most aspects of the invention, the sample is collected, stored, and provided in a container. Such a "sample container" can be any suitable type of container for maintaining samples in the context of the method to be performed. In some aspects of the invention the sample is either directly analyzed from the sample container or is placed into a different analysis container prior to analysis. Sample containers can include or possess certain features that are advantageous in the performance of some of the techniques described herein. Typically, the sample container is enclosed and usually at least partially isolated from the environment (and preferably substantially if not completely or essentially completely isolated from the environment), so as to maintain some portion of the volatile compounds in the sample over time, allowing for the other steps of the method to be performed a period of time after collection (and storage). In specific aspects, the sample container is capable of preserving a majority of the volatile substances in the sample at the time of insertion into the sample container (and in some cases more than a majority such as about 65% or more, about 70% or more, about 75% or more, about 80% or more, about 85% or more, about 90% or more, about 95% or more, or even about 99% or more (e.g., 99.5%, 99.9%, or more) of the original volatiles are maintained) for a desired period of time (which may be, e.g., 1 week, 2 weeks, one month, three months, six months, or even a year or longer). The maintenance of volatiles in such instances can be under typical, limited, or special conditions (e.g., refrigeration or freezing may be required or desirable in some cases, but in many cases samples can be maintained under a wide variety of temperature conditions without much additional care). In other aspects, the sample container need only be able to maintain a sufficient level of volatiles to be able to be tested in the method, which may be less than 50% of the volatiles in the sample when the sample was loaded into the sample container. In some cases, the amount of volatiles is more than about 65%, such as about 75% or more, about 80% or more, about 85% or more, about 90% or more, about 95% or more, about 97.5% or more, about 99% or more, or even about 99.5% or more (such as about 99.9% or more) of the volatiles present in the sample when placed in the sample container are maintained. In some aspects samples may be maintained in the container with one or more substances that reduce the likelihood of biological activity that might reduce the probative value of the sample.

In one aspect, the sample container comprises a feature such as a seal, wall, cap, or the like (hereinafter simply referred to as a "seal", unless context requires otherwise or unless otherwise explicitly stated), which is selectively penetrable by a flow channel device, such as a needle, such that volatile substances in the container can be released when the sample container is penetrated without significant loss of such volatiles. Thus, the seal is typically of a material and construction such that it will not release volatiles upon puncture or other formation of passage through it to provide means for releasing the volatiles to the other components of the system used to perform the method. Methods for determining the integrity of the seal can be used optionally in the method, as described below with respect to collapsible portions of the container. Loss from or contamination into the container from the puncture or other type of opening of or passage through the seal will typically be non-detectable or will be of very small amounts (e.g., less than about 1%, less than about 0.25%, less than about 0.1%, or even lower amounts).

In another aspect, the methods, systems, and devices can be practiced with containers that comprise a puncture-free method/step and/or puncture-less component/system or device for providing access to sealed volatile substances inside a sealed sample container. For example, in one facet the invention provides a system and method in which a sample container, such as a sample tube, is able to be selectively open to the system, such as facets wherein the sample containers are sample tubes within an enclosed autosampler and the remaining portion of the system comes into fluid communication with the container/sample upon positioning of the sample tube into a position in which the open end of the sample tube/container is allowed to interface with an entryway to the remainder of the device/system, typically, for example by means of an automates vacuum sealing connector, which may, e.g., cause an O-ring to be tightened between the system and the open sample tube, thus sealing the tube to the system without any puncturing or any needle passageway. In this kind of facet, the system/device does not permit significant loss of contents from the sample tube in the system, as described elsewhere herein with respect to other sample containers (e.g., less than about 5%, less than about 3%, less than about 1%, less than about 0.5%, or even less than about 0.2% of the contents are lost after placement into the sample container, in this case in the system/device).

In another aspect, the sample container also or alternatively comprises sufficient space beyond that which is occupied by the sample itself, such that some portion of the container can be filled with released volatiles. Accessible space also often is provided for the needle or other channel forming member or device to allow access into the sample container, in aspects where a sealed container is provided. Thus, about typically about 2-20%, such as about 3-15%, e.g., about 4-10% of the container, when sealed, is left as open space providing space for gas and also for flow channel device entry. The container may have more open space before sealing to also provide room for the seal (e.g., about 5-25% of the container may be designed to be open before the sealing).

In still another aspect, the sample container also or alternatively comprises a portion that is designed to be modifiable under certain conditions, such as being collapsible under mechanical pressure, such that the force of any sufficient mechanical pressure applied to the sample container can be transferred to the sample and thereby cause or increase the release of volatile substances, preferably without disrupting the structural integrity of the sample container in any manner that would cause release of any amount or any significant amount of volatiles that are released in the container (e.g., less than about 1%, less than about 0.25%, less than about 0.1%, or less than any detectable amount of volatiles are released from the application of force on the collapsible portion of the sample container) and/or causing the contamination of the container space (and volatiles contained therein) with substances from the surrounding atmospheric environment (such as air in the laboratory). The method can comprise monitoring pressure in the container or pressure in the container as connected to the analytical device, as one measure to make sure that no loss and/or contamination is occurring due to leaks. Other methods also or alternatively could be performed to ensure that such leaks of the container are not occurring, such as analyzing compounds in the environment around the container using conventional methods. As noted above, such techniques also can be applied to ensuring the integrity of other aspects of the sample container or other elements of the system that are used in the practice of the methods.

In typical and preferred aspects, the sample container is specifically adapted for use in one of the inventive devices described elsewhere herein for performing the various methods of the invention. Features that the sample container typically will comprise in order to be suitable for use in such devices include (1) a penetrable seal which is comprised of a seal material that is both (a) inert with respect to and (b) is at least substantially if not entirely impervious to the sample material and volatile materials contained therein (by "inert" it is meant that the material will not chemically react with the volatile materials and the sample materials, and does not give off volatiles under the conditions in which the method is performed, thereby modulating the analysis), and (c) is adapted in shape and size to seal the body of the container with respect to transmission of gasses and other materials that might partially or entirely interfere with, corrupt, or diminish the effectiveness of the analysis, and, preferably, and (2) a body comprised of a material that can be subjected to forces to be used in the method for drawing out of volatile materials, which in preferred aspects includes crushing of the sample container (and materials within the container) (e.g., the sample container body comprises or is composed of a material that is crushable under the force used by the device, allowing the sample of the material to also be crushed while releasing volatile materials from the sample into the container, the sample container being constructed in such a manner and of such materials so as to not be compromised, and so as to not lose its sealing properties on being crushed as discussed elsewhere). The principle of inert material discussed in this paragraph also typically applies to all elements of the sample container and other elements of the system used in the practice of the method. Thus, for example, tubing, trapping devices, and analytical devices incorporated into the system will similarly be selected based on being inert with respect to the sample and volatiles expected to be present and subjected to analysis.

In certain aspects, the method comprises multiple rounds of crushing, such as crushing the sample container by application of crushing and/or squeezing or compression forces, typically from different directions. In still a further step, the method comprises restoring the container, at least partially, to its original shape after application of a crushing step or multiple crushing steps. The step of crushing or compressing samples can be performed at any suitable time. In one aspect, the step of crushing is performed after the application of other forces that promote the release of one or more volatile substances from the sample. In another aspect, the step of crushing or compressing the sample is performed prior to the application of other forces on the sample to promote the release of volatiles, such as the application of pressure to the sample. In still other aspects, as described elsewhere herein, the step of compressing the sample can be performed independently of extracting or releasing volatile compounds (and vice versa).

The preferred sample container is at least partially or relatively flexible in design to allow for capturing a variety of sample types under a variety of conditions. Methods of the invention can vary considerably in terms of pressure, temperature, gas content, and other relevant factors. The sample container and other elements of the system typically are selected to be able to operate under a wide variety of such conditions. Pressure conditions are provided elsewhere herein that can help characterize such suitability. Temperatures used in practicing methods of the invention can also vary considerably, especially where high temperatures are used to remove material and freezing is used as a trapping method. In this respect, the overall system, including the sample container, may see temperature ranges from about −273/−270 degrees C. ("degrees C." herein means degrees Centigrade) to about 500 degrees C., such as about −195 degrees C. to about 200 degrees C. In many aspects, the temperature in the system will not exceed or even possibly not reach 100 degrees C. In other aspects, the temperature in the system will not exceed or possibly not reach 50 degrees C., particularly in the sample container. By remaining at such temperatures more affordable materials can be used in the practice of the method. Also, these extreme temperatures may not be reached in all parts of the device. For example, heat may be applied to the sample container, but freezing temperatures may only be applied to the trap device.

The flow channel or needle is used to penetrate or otherwise form a passage for the flow of gasses from the sample container (or more particularly in typical embodiments a needle is used to penetrate a seal component of or associated with the sample container). In embodiments comprising the use of a needle, the size of the needle typically is selected such that it provides sufficient flow of volatiles from the sample container to the rest of the system but is not so large as to cause puncturing of the seal and release of seal material (or other portion of the container) into the interior of the sample container. A needle used in the methods herein can have any suitable configuration of inlets (holes) to receive the gas. A single hole, placed in the side, or two holes, placed on each side, of the needle, is typical. Side placement of the needle can help ensure that the needle inlet does not become clogged after passage through a seal or sidewall of the container. A type 5 needle (by Hamilton), for example, provides such a balance with respect to exemplary devices described herein.

As noted above, sealed samples can be stored for significant periods of time and still be successfully analyzed using the methods of the invention. Some volatiles can be trapped in hermetically sealed voids in solids, such as fluid inclusions in rocks. In some embodiments, such volatiles can be analyzed years or decades after the sample is collected. The volatiles hermetically sealed in the solid can be released by crushing the solid, or by thermally heating the solid until the volatile filled voids decrepitate.

Other volatiles can readily escape from their solid, liquid or gaseous host. Such volatiles include oil, water, and gas in pores in drill cuttings or core, or within the drilling mud used by the well. It will typically be desirable that such solid and liquid samples are sealed as quickly as practically possible to permit the most representative analyses of the oil, water, and gas in the Earth's interior. As demonstrated and discussed elsewhere herein, the methods of the invention can be practiced with old, exposed materials, in which some or even significant loss has occurred, but better results are often obtained with samples that are sealed within a short period of time from the sample reaching the surface or being exposed to changed atmospheric conditions that would allow for release of relevant substances.

In one aspect the inventive methods are practiced without application of a significant vacuum or pressure on the sample prior to performance of the method. My prior inventions and other prior art methods often will apply significant vacuum or pressure and/or significant temperature to samples prior to analysis of the materials. The lack of such a step in certain aspects of this invention is yet another way in which such aspects are significantly distinguishable from the prior art.

While sample containers that can be crushable or otherwise compressible are often preferred, a large variety of sample containers may be adequate for samples that do not require mechanical disruption (e.g., glass vials, graphite tubes, or other containers that are impermeable and inert) in the practice of certain aspects of the inventive methods. Thus, for example, if there is to be no mechanical disruption either glass vials or sealed metal tubes can be used as sample containers. Various hoses made of rubber or other polymers might also or alternatively suffice if they can be hermetically sealed. Even Mylar or plastic bags may suffice for some applications. In some aspects of the invention containers also can be comprise or primarily, nearly entirely, or entirely be made from carbon fibers. Indeed, any container that can be hermetically sealed might be sufficient, depending on the nature of the bulk material being captured.

Commonly, the sample container comprises a septum or a cap (e.g., a synthetic rubber or nitrile cap) that is inert and through which a suitable flow channel device such as a needle can be readily passed while maintaining the seal's integrity. In such aspects, the volatiles purged from the sample will enter the inlet lines through the needle. Such elements of the sample container are optional. In another exemplary embodiment, the sample container is sealed using a compression fitting that can be automatically applied, with subsequent rupture of the sample container to release the volatiles into the system's inlet. Another approach that may be more appropriate in some instances would be to insert the entire sample container into a hermetically sealed chamber that is attached to the inlet system, followed by subsequent rupture of the sample container to release the volatiles. The sealed sample container could be introduced automatically one at a time through an appropriate port, or an individual sample or multiple samples could be preloaded and sealed into part of the inlet system.

If the sample is to be crushed and is on the exterior of the inlet system connected by a needle through a septum, cap, or some other means, such as a remotely controlled compression fitting, it can be desirable that the container can be crushed without leaking, and that any motion of the sample during crushing does not break the seal between the sample container and the inlet system. The selection of parameters for sample containers, seals, other elements of device, and compression/crushing methods in general will be selected such that a seal is maintained and there is no undesirable loss of volatiles or material or contamination thereof. A brass cylinder sealed on the bottom with a neoprene plug and sealed on the top with a nitrile cap, for example, can be a suitable sample container. However, other metals and other sealing methods may be employed in the sample container or systems/methods of the invention. For instance, a brass rod could be partly drilled out to make a vessel sealed on the bottom, thereby eliminating the need for the neoprene plug. Similarly, the cap could be made of a variety of compounds, however Nitrile has very good sealing properties for hydrocarbons and most other volatiles.

It is typically important that if a cap is used to seal the sample container that it can be hermetically sealed to the body of the sample container. This can sometimes be achieved by simply having the cap's resting diameter be sufficiently smaller than the tubes diameter so that the cap needs to be stretched over the tube or fit into the tube that forms the body of the sample container. Stretching in this manner might by itself typically result in a sufficient seal. If not, then additional methods must be employed to affect a hermetic seal between the cap and the tube, such as applying a compression device such as a hose clamp or zip tie or a metal ring having a diameter greater than the tube but less than the diameter of the cap when covering the tube, around the outside of the cap. Other methods of sealing the cap to the tube can include applying glue, or epoxy, or wax, or grease, or some other sealing substance between the cap and the tube. It is also possible instead of a cap to use a septum crimped to the top or some other part of the sample container for a needle to pass through, or even a polymer plug, such as a neoprene plug used to seal the bottom of sample containers. For a sample container that is secured to the inlet system by an outer compression fitting, or some other means such as a screw fitting as on a hose (or a threaded cap), that is a larger than a needle can form a channel or flow path between the sample container and the inlet system. Such a sample container adapted to be in direct material communication with a wider diameter inlet system can be sealed using a wide variety of sealing material including metals, polymers, glass, even such exotic means as a salt or sugar plug, glue, or other adhesive or sealing material. The sealing material typically will make a hermetic seal after the sample is captured up to the time it is ruptured and must be amenable to rupture after attachment to the inlet system. Similarly, sample containers that are loaded entirely into the inlet system generally will be hermetically sealed following loading of the sample, and usually will maintain that hermetic seal until somehow ruptured or made permeable to the substance(s) of interest at the appropriate time inside the inlet system.

As exemplified by the foregoing passages, it can in some aspects be advantageous and/or important that the overall system (sample container, inlet, or other elements of the system) are configured and constructed such that the overall system maintains its integrity, particularly with respect to the sample and volatiles released therefrom, upon the application of any forces applied in the method, such as any crushing force. An example of such an approach is the use of a needle-associated slug, as exemplified elsewhere herein.

In aspects where application of a crushing force causes parts of the sample container to move, become deformed, or otherwise become displaced, such movement may permit the hole that the needle passed through to become enlarged, which might, if not addressed, allow undesirable release of materials from and/or contamination of the system/sample container. A slug associated with the needle, such as by use of a compression spring placed around the needle, forcing intimate contact between the slug and the cap or seal, can assure the user that any such expanded hole formed in the cap or seal will still not permit such release or contamination. However, other approaches can similarly be used to ensure that the entire sample container/device system maintains the integrity of the material, depending on the configuration of the device and sample container (and steps of the method) and any released volatiles and the invention is not limited to this slug/spring approach. For example, if high temperature is applied to the sample container, the sample container and inlet may be configured and composed such that the application of such high temperature does not allow the formation of any cracks or openings that would similarly allow for undesirable contamination or release.

In one aspect, the crushing of a sample container and sample contained therein is used to assess the ductility (and/or porosity) of the sample and, correspondingly, the material. In a method in which a material of relative standard strength (in terms of crushability under a relatively fixed amount of crushing force) (such as by using the same quality of material in the same thickness, etc., within very small variations (e.g., about 10% variation or less, such as about 5% variation or less, such as about 1% variation or less in thickness and other relevant characteristics), is employed with a standard measure of sample (again, given the ability to have similar variability in the amount), the amount of collapse of the container, reflecting also the crushability of the sample, can be correlated to either the strength of the material and/or the ductility of the material (and/or porosity of the material). Such methods can be advantageous where the method is performed in connection with oil fracking or similar methods in which ductility of the material is a very important feature of the material.

Mapping the ductility of samples versus measured drilling depth in vertical well, or in a horizontal well, can provide information as to which sections of rock are most likely to have low risk of fracking failure. Fracking failure occurs when the rocks that have been hydraulically fracked do not have sufficient mechanical strength to maintain the induced fractures open following the injection of a proppant, usually sand. This aspect of this invention therefore is termed "frackability", as an advantage of this aspect of the invention is permitting practitioners of the method to map those sections of rock drilled by a petroleum well that will maintain open fractures following fracking and proppant injection. This can be especially critical nearest to the borehole, since if the fractures near the borehole do not remain open, no or only a very diminished amount of oil and/or gas can be produced.

One realization of this aspect of the invention is to measure a container, such as a sample tube as described herein loaded with cuttings, after squeezing with a known force, with a micrometer or other appropriate measuring device. Such a method can be performed manually after the sample has been squeezed, or can be done automatically as part of the analytical process using a device such as a linear translator that mechanically monitors how far the pneumatic pistons are extended after squeezing the sample is completed, or a device such as a laser ranging instrument, also to measure the total extension of the air piston, or other squeezing means, after the sample is totally squeezed to its final thickness.

Real time measurement of the squeezing process by an appropriate measurement means allows additional information to be collected that provides useful and necessary information for the design of a optimally successful fracking job. This includes measuring how the air piston or other squeezing means deforms the sample as a function of time and/or the amount of pressure applied. The sample deformation may be relatively rapid, or relatively slow. The deformation may be a smooth continuous process, or may be a series of discontinuous forward lurches. Also, of interest is how far the piston is pushed back by the sample after the pressure is released from the air piston, that is how much does the sample recover. The collection of these data during the squeezing process will allow for the calculation of various parameters vital to a successful fracking job, including Poisson's Ratio and Young's modulus.

Analyses of these parameters using the current state of art in the industry usually requires the expensive acquisition of a conventional core, or rotary sidewall cores, followed by expensive and time-consuming measurements at a laboratory usually some significant distance from the well. Often it is months after the well is drilled before the results of these other measurements are known.

Frackability from petroleum drilling cuttings can be rapidly determined either in the lab or on the well site. Turnaround time for transport of samples to the lab followed by analyses can be less than 24 hours. This is fast enough for the data to be used in deciding the final manner in which the well will be completed, such as what zones will be perforated, or where a horizontal lateral will be landed following the drilling of a vertical pilot hole.

Even more timely results can be had by measuring frackability of the well site while the well is drilling. This can be done by manually collecting samples and then loading in an instrument at the well site for analyses. In another aspect of the invention, frackability can be determined at the well site using an automatized instrument that collects a sample of drill cuttings and squeezes them and monitors the deformation. Such an automated apparatus would not require loading the cuttings samples into a container. The cuttings can fill a collapsible compartment in the well site frackability apparatus. Following filling of said compartment with cuttings the squeezing mechanism of the apparatus squeezes the cuttings while the amount and systematic of the deformation of the sample is recorded using a linear translation or other type of measuring meter. The data thus collected would then be stored on a computer, and can be instantly integrated with other drilling parameters generated by other instruments on the well, including logging while drilling tools, such as gamma ray logging while drilling, rate of penetration, weight on bit, mud log shows, etc.

Real time frackability data can be combined with other real-time data to determine the optimum way to drill the well. The data can be used to help steer lateral horizontal wells to stay in the optimum formation.

In one aspect, the invention provides a method for analyzing the frackability (ductility or hardness) of a material, such as a geologic formation, which comprises the steps of (a) providing one or more analyzable samples of the material, (b) subjecting the sample to one or more forces that are capable of compressing material of a given hardness or ductility, and (c) determining the amount of compression of the sample caused by the one or more forces. The analyzable sample typically, but not necessarily, will be from or associated with a petroleum well or petroleum exploration. The most basic form of the frackability method is distinct from prior approaches used to assess hardness of a geologic material, which either depend on scratching (e.g., the classic Mohs scale testing) or penetration of a point of the material or point contact with a surface of the material (such as by using the Schmidt rebound hammer), although such methods can be combined with the basic frackability method. In one aspect, the compression force is applied to at least an entire side of the sample. More typically, the compression force will be applied to multiple sides of the sample contemporaneously (within 2 minutes, within 1 minute, within 10 seconds, within 5 seconds, within 3 seconds, or within 1 second of each other), and, most often, simultaneously. Frequently, the compression force(s) will be applied isotopically, that is to say that it/they will be applied to all sides of the sample contemporaneously or simultaneously. Where advantageously combined with other methods of the invention, the compression study will be conducted in a compressible container, as exemplified elsewhere herein. The sample often is either a cutting or taken from a core sample associated with a petroleum well or petroleum exploration. Thus, in many aspects the size of the sample will be the size of a cutting, as explained elsewhere herein. In one aspect, the method is performed on cuttings that are associated with petroleum-associated mud. In other aspects, the method comprises washing the sample prior to crushing.

A further distinction in the typical application of the frackability method and methods of assessing hardness of geologic materials in the prior art is that the frackability method, especially when applied to cuttings, is applied to a large number of materials (at least 10, typically at least 20, and often more, such as at least 25, at least 30, at least 40, at least 50, or more) that are obtained from different depths and/or different locations within a relative zone of depth, and frequently such materials are brought to the surface within the relatively short amount of time that is required for petroleum drilling (e.g., about 1 day to about 12 months, such as about 1-300 days, about 1-250 days, about 1-240 days, about 1-200 days, about 1-180 days), such that the samples comprise a number of samples obtained during this period (e.g., a majority of the samples are obtained within 200 days of each other or at least 20, at least 30, at least 35, at least 40, at least 50, or more, of the samples in the analysis are obtained within at least 240, at least 180, at least 120, at least 90, or at least 60 days of each other). Currently, assessments for fracking suitability have typically made using either (1) minerology assessments, which determine the mineral structures present in the drilling area or potential drilling area through sampling, (2) x-ray diffraction methods to similarly assess the geologic content of the area (within the detection limits of that method), and (3) assessing the total organic content of the exposed area of the material. These practices can be combined with the compression frackability methods provided by this invention, in certain aspects, to provide additional information about the material. However, in another aspect, compression frackability can be performed as an assessment method without employing any of these methods.

A collection of samples evaluated in the frackability, such as cuttings, can consist entirely of samples obtained from locations in the material that are at least about 0.5 feet apart, and typically (but not necessarily) up to about 100 feet apart from one another (e.g., they can be from depths of a well that are at least 0.5 feet apart, at least 0.75 feet apart, at least 1 foot apart, or even further apart, such as at least 18 inches apart or at least 24 inches apart), or the set of samples can substantially consist of (e.g., at least 85%, at least 90%, at least 95%, at least 97%, or at least 99%) samples obtained from locations characterized by such differences, or the set of samples can be characterized in that a majority of the samples were obtained from locations having such differences in space, or at least a large proportion (such as at least about 10%, at least about 20%, at least about 25%, at least about 33%) of the samples were obtained from locations that have such relative spatial separation. In view of the possibility of lateral drilling the separation between the samples also or alternatively could be in the same relative zone of depth (e.g., within the same 500 ft, 400 ft, 350 ft, 300 ft, 250 ft, 200 ft, 150 ft, 100 ft, 50 ft, 30 ft, or 25 ft vertical zone). In some aspects, multiple samples from approximately the same location are tested, but the set comprises a number of samples from different locations (e.g., at least 10, at least 20, at least 30, at least 50, at least 100, at least 150, at least 200, at least 250, at least 300, at least 400, at least 500, at least 750, at least 1,000, or more samples, from locations in the material that are at least about 0.75 ft separated from each other). The number of total samples used in such a method will typically be greater than about 10, such as greater than about 20, and often can be significantly more samples, such as at least 50, at least 100, and can range from 10-5,000, 10-3,000, 10-2,500, 15-3,000, 15-2,500, 20-3,000, 20-2,500, 25-3,000, 25-2,5000, 25-2,000, 20-2,000, 10-2,000, 20-1,500, 25-1,500, or 10-1,500 samples, The total area of assessment can be significant, such as at least about 0.25 miles, 0.33 miles, 0.5 miles, 0.75 miles, 1 mile, 1.25 miles, 1.5 miles, 1.75 miles, 2 miles, or more, in depth and/or in horizontal area, reflecting lengths of modern petroleum wells. Thus, the frackability methods of the invention can provide a relatively fast map of the suitability of fracking a well site. In some respects, the entire analysis is conducted near the well site (such as within 200 feet of the well site). This can be achieved by using devices of the invention that compress material near the point of separation of cuttings and muds, for example, in petroleum drilling.

In some aspects, the compression frackability methods of the invention are combined with the other methods described herein for assessing hydrocarbon content of a material through release of volatile compounds, such as organic acids, which may be released using the methods described herein (e.g., application of gentle vacuum, trapping, and optionally analysis by sensitive methods such as mass spectrometry analysis). In other aspects, the frackability methods of the invention and the volatile compound analysis methods of the invention are practiced separately. Similarly, for the devices of this invention, such devices can comprise combined frackability and volatile compound analysis components/systems, but the invention also provides devices that comprise these functions as individual features.

Some aspects of the invention, particularly those in which released volatile compound analysis will be performed as a part of the inventive method, are characterized by comprising a step in which sample material is stored quickly, and typically in a sealed manner, after arriving at the surface or otherwise being exposed to normal atmospheric conditions. For example, at an oil well site such a method can comprise collecting cuttings in a sealed container within a short amount of time after such cuttings reach the surface. The time for collection can vary with the nature of the sample, the method to be applied, and the target material(s) that are sought to be identified by the method. In an exemplary aspect of the invention, the samples are sealed in a sealable container in about 5 minutes or less, but more typically the time will be about 3 minutes or less, about 2.5 minutes or less, about 2 minutes or less, or even about 1.5 minutes or less, such as about 1 minute or less. Samples can be subject to washing immediately before sealing in a sealable sample container. Sample washing can be carried out by any suitable method. More generally, but not necessarily, cuttings or other materials typically are stored such that volatile compounds contained therein are not lost below limits detectable by the method. Volatile gasses and chemicals that rapidly expand under atmospheric pressure and non-constrained conditions, such as petroleum-related hydrocarbons, can be readily released from such materials once they reach the surface. Accordingly, it is advantageous to store materials to be analyzed such as cuttings within one or more containers that will ensure no release or little release of such substances during the time the material is to be stored and/or transported. In a preferred aspect, the materials are stored in one of the devices described elsewhere herein, and most preferably such a device is configured to fit securely within one of the analytical devices of the invention described further elsewhere herein, such as by mating with an inlet or by using a flow channel device, such as one of the needle devices discussed herein.

A filter material also can be added to the sample container. Any type of suitable filter material can be used. Suitability in this respect generally means that substantially all (e.g., at least about 95%, such as at least about 99%, or at least about 99.9%) of the material (excluding the volatiles released from the material) is maintained in the interior of the sample container and does not enter or come into contact with the flow channel or inlet. Simple filter materials such as cloth materials and cotton pellets have been demonstrated to be suitable for this purpose. These materials, as with other materials used in the sample container and throughout the system must be inert with respect to reacting with volatile chemicals and emitting materials that would interfere with the analytical aspects of the inventive methods.

In one aspect of the invention, the sample(s) that is/are analyzed in the method is or comprises a drilling mud. Muds have been discussed elsewhere herein. The mud can be an oil-based mud or a water-based mud. The analysis of muds typically means that more than one mud samples are taken. This is because material can be maintained in a mud over several re-uses of the mud (or passages of the mud to the drill bit point and the surface where a sample might be taken). Accordingly, samples may be taken at points that correspond with an "up mud" (mud arriving at the surface) and a "down mud" mud going back into the well, which will help to identify changes in the mud over time, aiding in the analysis of the material through studying the mud. In one aspect, the method comprises the analysis of mud materials and cuttings. In still another aspect the method comprises the analysis of mud materials, cuttings, and/or fragments of core samples, such as samples of each of these categories taken from a petroleum well or petroleum exploration site.

The material and sample are typically a solid (as in the case of a cutting), but in other aspects of the invention the sample and/or material is a liquid or a gas, and in still other aspects the sample and/or material is a mix of two or more of a solid, liquid, or a gas, or a combination of all three forms of material. For example, in an industrial setting, samples can be taken of the air to ensure that the amount(s) of certain compounds (e.g., benzene) are within certain levels. In still another embodiment the method is applied to look for seeping, such as gasses seeping into and/or out of a geological formation. Geothermal activity also can be assessed by the method. In another aspect, the method can be practiced with a liquid, such as water, to assess the level of certain substances in the liquid (such as contaminants in water samples). As noted elsewhere the material can be of natural, synthetic, or semi-synthetic origin, and may be generated from a variety of origins and/or settings, such as industrial solids, soft materials, liquids, and air, or other gases.

In preferred aspects, the method is applied to analyze the volatile compound content of the material. Volatiles in rocks typically contain important information used for petroleum, geothermal energy, and mineral exploration and production. Volatiles in rocks can also be used to determine the suitability of quarried stone for road and building construction. Volatiles in rocks and soils may also provide information beneficial to ecological and environmental studies. Volatiles in solids that form as a byproduct of various industrial or civil processes, such as scales that can form in the casing of oil, gas, and water wells, can provide information that may help design processes to inhibit the formation of such unwanted solids. Volatiles in man-made solids such as bricks, concrete, ceramics, glass, and plastics can be used to ascertain problems in their manufacturing process, or to evaluate their utility for various applications. Volatiles that occur in solids that form in natural biological systems, such as bone, teeth, kidney stones, finger and toe nails, may provide insights that could help to maintain or improve the health of the individual or community from which these solids originated. Volatiles in softer tissues from plants and animals, including humans, may also offer diagnostic information that may be useful to the health of the source organism. Such methods may have application in testing in food safety testing, food viability, food storage, and/or shelf-life, or the like. Volatiles in industrial and natural liquids also contain a wealth of information that can impact the success and profitability of petroleum, geothermal energy, and minerals exploration and production; the efficiency and profitability. of manufacturing and other industrial processes; and the health and well-being of the environment, organisms and communities. Various explosive products may also have distinct volatile signatures that could be detected with the device described herein, thus volatile monitoring of air or solids may have benefits in keeping people, communities, the military, and law enforcement secure.

In one aspect of the invention the sample is taken from an outcrop and the material comprises an outcrop. Outcrops are geologically important formations. In one aspect, outcrops (outcroppings) are used as a comparator to subterranean materials, such as materials obtained from a mine or drilling site. Such materials may also contain evidence of materials seeping to the surface.

The material typically is dry, but in some aspects of the invention is moist or even wet (e.g., in the case of a liquid or a mud). In some aspects of the invention it can be important to ensure that the amount of a liquid, such as water, in the material, is not too high so as to overcome the capacity of the mass spectrometry device. However, in general, this is not a limiting factor, and the skilled artisan will be able to assess if any such situation arises. As already noted herein, the material, and thus the sample, will typically contain one or more volatile substances that will either passively release or be released upon the application of one or more forces on the sample. In either case, a gas will be released from the sample that contains one or more volatile substances, although, as discussed elsewhere herein, the sample can also contain non-volatile substances, which may also or alternatively be collected, and considered, as part of the analytical aspect of the inventive method. The nature of the volatile substances contained in the sample can vary considerably and the inventive methods can be practiced with various types of volatile compounds. In specific aspects, however, the sample and material contain a significant amount of one or more specific target substances. For example, in the case of drill cuttings, taken from petroleum production of exploration sites, the sample will contain detectable amounts of one or more species of C1-C20 hydrocarbons and related compounds that contain oxygen, nitrogen, sulfur or other heteroatoms; organic acids (e.g., C1-C5 organic acids, particularly C1-C3 organic acids, and most commonly acetic acid, carbonic acid, and/or formic acid); and/or one or more inorganic gasses, such as hydrogen, helium, carbon dioxide, carbon monoxide, water, nitrogen, argon, oxygen, hydrogen sulfide, carbonyl sulfide, carbon disulfide, and/or sulfur dioxide. In one embodiment, the sample comprises C1-C15 hydrocarbons, such as C1-C14 or C1-C12 hydrocarbons and the method comprises analyzing one or more of such hydrocarbons. In still another aspect, the sample comprises C1-10 hydrocarbons and the method comprises analyzing one or more of such hydrocarbons. In aspects that are often preferred the invention also or alternatively is characterized by the detection of acetic acid, carbonic acid, and/or formic acid contained in the sample or formed from application of one or more forces on the sample in the practice of the inventive method. In this respect, the sample can be characterized as comprising one or more compounds that form such compounds, or by having material that can form carbon dioxide, carbon monoxide, methane, and/or water.

In another facet, the inventive methods provided herein can be characterized in that such method comprises conducting an analysis of the sample for one or more substances containing a carbon chain of five or more, such as six or more, or seven or more carbon atoms. In some cases, the method comprises heating the sample or gasses to assist with the analysis of longer chain hydrocarbons or other carbon chain-comprising compounds, such as hydrocarbons having a backbone of more than 10 carbon atoms. For example, the method can comprise heating the sample or gas (or the device containing either or both) to about 130° C. or more, about 140° C. or more, or about 150° C. or more, to assist with the analysis of such longer-chain hydrocarbons. In this and other respects, the method can comprise controlling the temperature during which some or all of the process is performed, such as the temperature at which gasses are released and/or analyzed by the analytical processes of the method. Such methods typically can comprise heating the entirety of the system from the inlet, through to the trap, to the mass spectrometer, and through to the exit. In other aspects, it is preferred that the method is generally performed at room temperature, although in such aspects it may also comprise using freezing as a means for trapping volatiles and/or applying heat to release compounds from a freezing trap mechanism or media.

In some aspects, the invention is characterized by not creating new volatile compounds in the sample, such as forming volatiles from hydrated minerals (where water is a part of the crystal structure, such as silicate clay minerals; hydrated oxides, such as brucite (MgOH2) and goethite (FeOOH); and other water-bearing mineral substances such as hydroxyl apatite; etc.) or where, e.g., carbon dioxide is part of the crystal structure (such as calcite ($CaCO_3$), dolomite ($CaMg(CO_3)_2$), and siderite ($FeCO_3$)); and solid and liquid hydrocarbons not volatile as a gas under the analytical conditions in which the methods of the invention are performed, such as C20 alkanes or various bitumins or kerogens; or any other substance that is normally not a gas or normally emits a gas under such conditions.

In practicing methods of the invention one or more gasses is/are typically released or extracted from the sample of the material. In some contexts, the gas can be released passively (without application of force or without application of a significant force); e.g., by exposing the sample or the container comprising the sample to a release channel or release passage, such as a needle or similar device which penetrates the container containing the sample. In other contexts, as noted elsewhere herein, the methods also or alternatively can comprise applying energy to the sample, such as by mechanical force, e.g., crushing of the sample or crushing of a container that has a crushable portion and that contains a crushable sample. In either case, the gas or gasses are released from the sample of material and then are allowed to flow such that one of the further steps of the method can be performed on such gas. The amount of time required for the gas to be release can vary with the conditions of the method, including the material, whether or not forces are applied to the sample, the time in which gasses are permitted to be released from the sample, and the sensitivity of the analytical methods performed on the gasses. Using the guidance provided herein skilled artisans will be able to determine these conditions. For samples that are analyzed at atmospheric pressure without the application of force a time of about 1 second may be sufficient, for example. Longer or shorter periods of time may be suitable, but such a relatively short period may be desirable. Longer periods may cause the sample to be under lower pressure conditions because of the relatively lower pressure condition of the device.

In many aspects of the invention volatile substances are extracted from a sample by subjecting the sample to various levels of vacuum. For some samples, important additional information is obtained by subjecting the sample to a range of increasingly lower pressures, in other words to increasingly higher levels of vacuum, and analyzing the chemistry of each individual aliquot extracted at each individual extraction pressure. This has proven to be especially useful for solids, particularly for various rock samples including outcrop, core, and cuttings samples as applied to the exploration for and production of oil and gas. Depending on the sample and the problem being addressed various other processes may be applied to the sample prior to any vacuum extraction, in between vacuum extraction steps, or even during a vacuum extraction step, as will be discussed further herein. In one example, another process that can be applied, and which is described elsewhere herein, is crushing or squeezing the sample or applying any process that mechanically disrupts the solid sample. Other processes that might disrupt the sample include sawing, or tumbling, or exposing to vibrational energy at any number of frequencies. Another process that could be employed is heating the sample; one effect of which can be disruption of the sample by thermal decrepitation of fluid inclusions and/or other structures in the sample. Chemical processes and/or application of energy also or alternatively may be applied to the sample in the performance of the method, such as, for example, applying an acid to the sample so as to dissolve certain substances. It is also possible that in some instances a combination of two or more of these or other disruptive processes may be usefully applied in the practice of the inventive methods.

The method also may include one or more steps performed before release of gasses, or between release of gasses (in methods in which there are multiple release steps or multiple samples analyzed). In one aspect, the method comprises purging some amount of air from the sample, e.g., by application of vacuum. In such embodiments the time the vacuum purge is applied will generally be such that the amount(s) of volatiles that are purged with the air is sufficiently small to justify the purging step. This may comprise, for example, only 1 or 2 second application of vacuum pressure, so as to lower the pressure from about 1000 millibars to about 50 millibars (but these are only exemplary figures). However, such a purging step can be important where the presence of air as a contaminant will interfere with the analysis. This may be important with respect to analysis of older samples contained in open environments.

In a further specific aspect, the inventive methods can comprise purging the sample, which may be a sealed sample, and replacing the purged air with another gas, such as argon, nitrogen, or helium, or any other suitable gas as determined by the specific advantage gained for the specific problem being addressed and the specific host solid and specific volatiles being analyzed. argon is typically preferred as nitrogen and helium may be relevant in the analysis of the sample.

These steps of purging (and optionally replacing) air or other surrounding gas provides a mean of removing potentially interfering substances in the air or other gas in which the sample is contained, which might provide false signals in the analysis (e.g., confusing methane with oxygen or nitrogen species found in air). Other methods of accomplishing the same goal may be available in the art and likewise suitable, but this method is preferred in many aspects of the invention. For example, in one alternative, the air or gas in an inner sample container is displaced with a liquid, such as a diffusion pump oil, and the inner sample container placed in a surrounding, outer container. The inner sample container comprises or typically is entirely made of a material that can be crushed or compressed by application of a force. A vacuum is applied to remove any air from the surrounding container, creating a vacuum condition in the space formed by the surrounding container, and the entire sample container sealed. A force that compresses or crushes the sample in the inner container is applied, breaching the inner container and releasing volatiles into the now exposed outer container. Such materials can then be subjected to further analysis in accordance with the inventive methods described herein with little risk of interference from substances in air, etc.

The rapid purging of air from the sample, and rapid replacement with argon or other gas prior to crushing the sample can be particularly relevant in analyzing samples relevant to oil and/or gas exploration. Generally, these methods are applied to older samples maintained under open conditions, as there is a trade-off in terms of loss of volatile substances in applying the purging methods. Thus, for sealed samples, such methods may not be practiced.

Purging (and purging and replacing processes) can facilitate the mass spectrometer analyses of very small amounts of certain substances, such as methane, using mass 15 for the $CH_3^+$ ion, by removing nitrogen and oxygen. The lower resolution of many quadrupole mass spectrometers makes it difficult to analyze trace methane using mass 15 in the presence of major amounts of nitrogen with a major peak on mass 14 and oxygen with a major peak on mass 16. Purging and replacement of air with other gases may have other benefits. Replacement of air with krypton, having mass 86, would solve the methane interference issue as does argon, but could also aid in the extraction of some recalcitrant volatiles in the solid by imparting a much greater amount of energy in collision with the lighter gases present as the sample's voids are evacuated.

Most purging steps are completed quickly, especially when the step comprises the removal of air in the system by means of quick vacuum (versus flowing of an inert gas or a combination of both types of steps). For example, in one aspect the purging process is complete in about 10 seconds or less, such as about 5 seconds or less, about 3 seconds or less, or even about 2 seconds or less. In the case of a quick vacuum purge, application of such a step for less than about 3 seconds, such as less than about 2 seconds, less than about 1.5 seconds, or even 1 second or less can be advantageous. Another way to characterize such a step in some aspects is that the vacuum purge step results in a loss of less than about 5%, less than about 2%, less than about 1%, or even lower losses (e.g., less than about 0.5%) of the oil and with respect to gasses the losses are less than about 10%, less than about 7.5%, less than about 5%, less than about 3%, or less than about 1% of the gas present at the time the sample is introduced to the system. Purging is typically performed prior to crushing or squeezing of materials, or other application of forces to the sample. At the well site, samples may not be purged as nearly all information can be converted into data, especially with the use of control sampling devices/systems that are used to calibrate the system (with respect to gasses that are at the site and not associated with the samples). For sealed samples, the method also may lack purging, as this may result in data loss. As such, purging steps are often optional, but can be useful when there is a determination that there could be a risk of an interfering signal.

Depending on the problem being addressed by the analytical method, it also or alternatively may be advantageous to heat or cool the sample prior to volatile extraction. Heating or cooling of the sample can be performed alone or with crushing and/or purging (or purging and replacing the air or other surrounding gas). For instance, if volatiles in water ice were to be analyzed, the sample would need to be held at a cold enough temperature to keep the ice frozen during volatile extraction and any purging and gas exchange for air preceding crushing. A temperature of about minus 50 degrees Centigrade might be needed in this example to keep the ice from sublimating in response to the applied vacuum. A similar process could be advantageous in the analysis of gas hydrates, otherwise known as clathrates.

Centrifuging also or alternatively can sometimes be an aid to volatile extraction. Centrifuging an upright sample prior to volatile extraction, for example, can cause the vertical stratification of volatiles in the container, gases would migrate to the top, and oil would in general form a layer on top of water. This can be particularly useful in the analyses of volatiles in drilling muds from oil and gas exploration and production wells. Centrifuging following crushing can sometimes also have similar advantageous effects.

After all preparatory processes, if any, are complete the volatiles typically are extracted from the sample by reducing pressure on the sample by exposing the sample container to an inlet system that is under static vacuum and is not being actively pumped. The inlet system typically is sealed off to vacuum pumps at this point in the process, having been previously evacuated by vacuum pumps. Pressure is reduced on the sample by opening a valve between the sample container and the inlet system allowing gas to pass from the sample through the needle or other flow channel device into the inlet system. During a multi-stage extraction, at increasing levels of vacuum for each extraction, the first extraction results in a resulting pressure on the sample and in the inlet system that is determined by the gas pressure in the sample and the sample container, the void volume in the sample container, and the volume of the static inlet system. Each collection of extracted gas(ses) obtained by such a method is referred to as an "aliquot" herein. Thus, for example, the first extraction of a gas at atmospheric pressure or a different pressure may be referred to as Aliquot 1, with subsequent aliquot numbers each increasing by one, so that a three stage analyses will have Aliquot 1, Aliquot 2, and Aliquot 3. In typical practice, Aliquot 1 is extracted at a pressure of about 50 millibars. A typical Aliquot 2 is extracted at an initial pressure of about 5 millibars, and this pressure for a typical Aliquot 2 is decreased by a period of active pumping following initial trapping of the more volatile gases to about 0.001 millibars or less (e.g., as low as 0.0001 millibars or lower, or any range between about 0.001 millibars and 0.0001 millibars, such as 0.005-0.0005, 0.00075-0.00025, or 0.0009-0.0002 millibars). The step of causing this significant type of pressure drop in the system, device, or method of the invention is advantageous in methods in which a mass spectrometry analysis is performed on the samples, as mass spectrometry conditions typically require lower pressures than those in which aliquot extraction methods are performed in order to appropriately operate. Such pressure conditions will be known in the art (or provided by the mass spectrometry manufacturer) and the achievement of such levels of pressure can be achieved through any suitable means, with many such methods and devices being available.

As mentioned elsewhere, the methods of the invention can, in certain instances, include one or more steps in which potentially interfering gasses are removed from the released gas or the environment in which the gas is released. For example, in one aspect the invention can include the step of flooding the device in which the method is performed with an inert gas such as argon, so as to remove gasses from the device, which might provide false signals or results. Normal atmospheric gasses such as oxygen, nitrogen, and/or both, for example, can be substantially removed, or nearly completely removed, or even entirely removed (to detectable levels) by administering ("flooding") to the device or a portion of the device in which the method is carried out with such an inert gas. Such a method also can be used as a method for refreshing the device between samples. Where an inert gas is used in such aspects, the inert gas can be any suitable gas that does not chemically react with the sample and does not cause any interferences with the chemical analyses of the samples' volatiles. In other aspects, a non-gaseous material, such as a liquid can be similarly used. The atmospheric or other interfering gas can be purged from the device, component, or environment in which the sample is being analyzed by, e.g., rapid vacuum extraction (e.g., applying a vacuum that is sufficiently strong to substantially or nearly entirely remove the purging inert gas for a duration of about 1 second or less). In another aspect, the method can comprise flowing an inert gas through the sample container or area to displace the potentially interfering gas. Such methods are not included in every application of the inventive methods. For example, where the method is performed on samples sealed at a collection site, such as a well site, such a step is typically not performed. However, such purging steps can be useful for analyzing the presence of target substances where such substances are or are suspected to be present only in very small amounts, such as with respect to methane and/or helium in samples that are associated with petroleum production or exploration sites.

Materials or methods also or alternatively can be used for removing other potentially interfering substances such as water vapor, for example, which is relevant to certain aspects of the invention in which water is formed and analyzed as a method for analyzing hydrocarbon content in samples. In one aspect, the invention is performed in the presence of a material that can capture essentially all, substantially all, or a relevant portion of the water vapor present around the sample that might be captured by either the trap or other tools for capturing substances used in the analytical method. For example, the system that is used for performing the method can comprise passages between system elements that are made of stainless steel, which promotes the absorption of water and thus removes water vapor contained in the gas content flowing through the system from reaching the next stage of the system.

The amount of volatile substances released from the sample, trapped on the trap, or analyzed by the analytical method of the inventive methods described herein can constitute any suitable proportion of the volatiles present in the sample, and the amount contained at each such stage in each of the aliquots obtained in multi-aliquot methods of the invention also can be any suitable amounts. Typically, most of the volatiles are captured by the method, such that at least about 90%, at least about 95%, at least about 97%, at least about 99% of the volatiles (excluding water, and particularly with respect to C1-C10 hydrocarbons and similarly structured organic compounds) are extracted from the sample, by the practice of the methods of the invention. The efficiency of the system typically also is high with respect to trapping of gasses that are condensable on the trap. Typically, condensable gasses that can be captured by the trap are not retained in the system in detectable levels. However, as discussed elsewhere herein certain gasses will not condense on the trap or otherwise be trapped by the trap and must be subject to handling by other means to be captured and analyzed by the method.

To exemplify (and clarify), methods of the invention can comprise analysis of a single aliquot, for example a single aliquot obtained under gentle/low vacuum conditions, or in other aspects the method can comprise obtaining and analyzing a plurality of aliquots from one or more samples and/or that are obtained under different conditions. For example, one method comprises obtaining two aliquots per sample, wherein the first aliquot is obtained by application of about 50 millibars (e.g., 10-100 millibars, such as 15-95 millibars, 20-90 millibars, 30-80 millibars, or 40-70 millibars) for about 3 minutes (e.g., 1-10 minutes, such as 1.5-8 minutes, 2-7.5 minutes, 2.5-5 minutes, or the like, in some cases it may be advantageous to perform the first aliquot extraction for shorter times in this or other contexts, such as 0.25-4 minutes, 0.33-3.5 minutes, 0.5-3 minutes, 0.5-4 minutes, 0.5-5 minutes, 0.5-2.5 minutes, 0.5-2 minutes, 0.75-3 minutes, 0.75-2.5 minutes, 0.75-2 minutes, or another similar time interval) and a obtaining a second aliquot by putting the sample under pressure conditions of about 5 millibars (e.g., about 1-10 millibars, about 2-8 millibars, about 3-7 millibars, or the like) for a period of about 10 minutes (such as 5-15 minutes, e.g., 6-12 minutes, 6-10 minutes, 5-9 minutes, 6-9 minutes, 7-9 minutes, 7-10 minutes, or about 7 minutes, about 8 minutes, or about 9 minutes), with the method optionally including a step of crushing/squeezing the sample during one or both aliquots, such as crushing the sample at the start of the first aliquot extraction, as described elsewhere herein. In some aspects, shorter extraction times (e.g., less than about 5 minutes, less than about 4.5 minutes, less than about 4 minutes, less than about 3 minutes, less than about 2.5 minutes, less than about 2 minutes, less than about 1.5 minutes, less than about 1 minute, or even shorter periods. In such aspects the parameters of the system and the method can be adjusted to facilitate shorter extraction time, such as, for example, using a relatively larger diameter needle system for the passage of volatiles out of a punctured sample container (e.g., use of a needle of about ⅛th or about 1/16th of an inch internal diameter as compared to about a 32nd of an inch diameter needle). In another approach, extraction time and/or purging time of the system can be reduced by to passing a non-condensable purge gas through the sample.

In some contexts, it may be useful that the method of the invention is performed and/or the device of the invention is provided with a plurality of trapping devices, which may be of the same or different nature. Thus, for example, in one aspect, the invention includes a plurality of non-selective traps, such as a plurality of liquid nitrogen traps. This kind of system/device can be particularly advantageous with multiple aliquot methods. In such methods it can be possible that each aliquot or at least a subset of the total number of aliquots are associated with each trap. This can, among other things, speed up the process of performing multiple aliquot analyses, for example by exposing the aliquots to the traps separately or operating traps at different times, such that there is little downtime in the system in the event a trap needs to be cleaned, set, or re-set in between uses. Where traps with different functional properties are provided, using different traps can enhance the information obtained from the method, by providing different dimensions to the analysis (e.g., by combining one or more non-selective traps with one or more selective traps, such as GC traps).

As already noted, gasses released from the sample are released to a system or device in which the remaining steps of the method are performed. Typically, the gasses pass into the system or device through an inlet, which may be a portion of the system or device associated with a needle or flow channel as discussed elsewhere herein or can be any other suitable type of inlet. Thus, processes employed before and during vacuum extraction can include attaching the sample container to the inlet system before initiation of vacuum extraction and any ancillary processes. A number of processes can be used to attach the sample container to the inlet system. These are described in the section on the various possible configurations of the sample container. Our preferred sample container is a sealed brass tube with a hermetically attached nitrile cap on the top and a neoprene plug in the bottom. Using the typically preferred sample container, the sample container is attached to the inlet system prior to initiation of vacuum extraction by passing a needle through the nitrile cap. Other types of sample containers must be sealed by other appropriate means to the inlet system prior to initiation of vacuum extraction.

Another step of the inventive methods also or alternatively can include applying energy to either the gasses generated in the practice of the inventive methods, which can include either gasses directly released from the sample or gasses that are released from the trapping device or media of the invention (the "trap", as further described elsewhere herein). The amount of energy and type of energy applied to gasses in such aspects can be in any suitable amount and form so as to generate one or more other target substances that, for example, are more convenient for detection and/or analysis than substances that were in the gasses prior to application of the energy. For example, the methods of the invention can comprise a step of applying an energy source such as a source of light energy to a gas, thereby forming compounds from organic acids, such as carbon monoxide, water, carbon dioxide, methane, and the like, in amounts that are suitable for detection by the analytical aspects of the inventive methods. Carbon monoxide often is preferred as a molecule for detection in that it typically lacks potential competing signals which may sometimes pose issues for analyzing water or carbon dioxide. Carbon monoxide is generated by the breakdown of formic acid (HCOOH) to water (H2O) and carbon monoxide (CO). This reaction even occurs at about 1 atmosphere pressures, so much so that some large bottles of formic acid are provided with a vent that allows carbon monoxide to escape and thus avoid unwanted pressure build up in the bottle. In contrast, acetic acid (CH3COOH) breaks down to water (H2O) plus methane (CH4), and carbonic acid (H2CO3) breaks down to water (H2O) plus carbon dioxide (CO2). Carbonic acid is only stable in solution, and has no stable gaseous phase.

The amounts of organic acids released from materials, such as cuttings, may be very small, and their respective indicator break down compounds may be masked by larger amounts of these compounds being released as compounds existing as those compounds in the sample. In geologic samples this is especially true for water, carbon dioxide, and methane. This is not a usual problem for carbon monoxide as its natural occurrence in samples from oil and gas wells is minimal at best. However, carbon monoxide can be generated as a by-product of oil and gas drilling by the process known as "bit burn" or "drill bit metamorphism". In a lab apparatus aspect of the invention, and related methods of use, some of the compounds derived from organic acids that are also present as naturally occurring interfering compounds, such as water and carbon dioxide, are frozen to a liquid nitrogen (LN2) trap. Carbon monoxide and methane do not freeze to the LN2 trap. However, methane as a naturally occurring substance is common in rocks from oil and gas wells. Therefore, the presence and amount of methane in rocks from oil and gas wells is not an adequate indicator of precursor organic acids. Carbon monoxide is not at all common as a natural component of rocks from oil and gas wells. Therefore, the presence of carbon monoxide typically is a good indicator of organic acids. Thus, for example, in one set of aspects the inventive methods comprise detection of carbon monoxide, but not methane or at least do not comprise relating methane levels to overall levels of organic acids in the material associated with the sample/cuttings.

In certain aspects, carbon monoxide is monitored using the AMU12 fragment formed by mass spectrometry analysis of carbon monoxide. In a more particular aspect, the method comprises performing a method in which carbon monoxide is a primary indicator of organic acids in the material, and is analyzed by evaluating the presence and amount of the AMU12 fragment formed by mass spectrometry performed on carbon monoxide, and the method is performed either free of any detectable amount of carbon dioxide or in the presence of an amount of carbon monoxide that does not result in a distortion of the carbon monoxide-associated AMU12 signal or the degree of the AMU12 signal that is associated with carbon monoxide. In some aspects, the amount of interference with the AMU12 signal from the presence of carbon dioxide in such a method is less than 25%, less than 20%, less than 15%, less than 10%, less than 5%, less than 2%, or less than 1%. In settings where carbon dioxide is present, the method can comprise either manually or automatically correcting the AMU12 signal data for the presence of carbon dioxide to obtain a carbon monoxide-associated AMU12 signal. In some aspects, the step of isolating carbon dioxide is handled by use of a trap that collects carbon dioxide, such as a liquid nitrogen trap, in a manner such that carbon monoxide and carbon dioxide are not in associated aliquots (for example, carbon monoxide in a lab device of the invention may be collected in a non-condensable gas state, whereas carbon dioxide is fixed to the liquid nitrogen trap). In other aspects the method of analyzing carbon monoxide level also or alternatively comprises analyzing the signal from AMU13 and/or AMU 16 and/or 28. In aspects where carbon dioxide is initially present but removed or substantially removed (e.g., by removal of at least 85%, at least 90%, at least 95%, at least 97%, at least 99%, or more, of the initial concentration) as a part of the inventive method, a CO2 absorber, such as Decarbite™, also or alternatively can be used to reduce or eliminate any detectable levels of carbon monoxide in the gas or aliquot to be analyzed, Also or alternatively, a mass spectrometer based machine designed to detect trace amounts of carbon monoxide in cuttings can be designed to use any of the CO2 eliminating/reduction techniques described herein and their known equivalents in the art.

In another aspect, the method is performed under conditions in which the application of the energy also or alternative changes the pressure of gas associated with the sample or generated from the sample in a manner or amount that is indicative of a chemical change that identifies the presence of a target substance or a target-related substance (such as carbon monoxide).

It is important to note that while in many aspects of the inventive methods mass spectrometry analysis is an important component of the inventive method, such a step is not always included (and often is not included) in these methods. Rather, other analytical steps can be performed to identify the presence of the target substance or target-related substance. For example, a carbon monoxide meter or measuring device can be used to directly measure the formation of carbon monoxide in a petroleum-related sample, thereby indicating the presence of organic acids prior to application of the energy, and thereby further indicating the presence of oil-related substances in the sample (and material). Also or alternatively, simply measuring the pressure in the gas related to the sample can be indicative of a relevant change, such that a pressure gauge, meter, or device can be used in the method, alone or in combination with mass spectrometry analysis (carbon monoxide monitoring also can be combined with mass spectrometry analysis or all three methods can be combined in the analytical method).

Such methods of the invention also can often be desirably performed in the field, such as directly at a well or exploration site. Accordingly, whereas many aspects of the invention comprise the use of small samples, in these and other methods larger amounts of materials may be used, such as cup sized containers, pint size containers, quart size containers, gallon size containers, or containers that have volumes of about 5 liters or more, about 10 liters or more, about 20 liters or more, or even about 30, 40, or 50 liters or more (e.g., a large bucket of sample material). For example, a large container of cuttings can be collected from where cuttings are deposited near a well site (e.g., in association with a well site shaker table) and then directly used for analysis with such methods.

In addition to or alternatively to light energy, other suitable types of energy can be applied to the sample in order to modify the gas content for direct evaluation or to see if pressure increases, indicating a change in content that is indicative of the presence of the target substance in the material. Examples of other types of suitable energy include heating methods, vacuum, other forms of radiation (e.g., UV light), and the like. In another aspect, the method also or alternatively can comprise performing a chemical reaction to form such compounds that are indicative of the presence of the target substance in the material. The amount of energy applied in practice of the method can be any suitable amount to achieve the desired change. In one exemplary aspect, the sample is heated to about 400 degrees C. or greater for a period sufficient to generate indicative target compounds (e.g., carbon monoxide) from organic acids present in the samples.

Methods of the invention can and often do include the step of subjecting a sample of the material, such as one or more cuttings associated with one or more geologic formations, to one or more forces to cause the release of a first gas containing an analyzable amount of one or more volatile substances. The force that can be applied to the sample can include a pressure force, such as a high pressure (positive pressure) or a vacuum; temperature; chemical reaction; application of radiation (such as microwave, which might be used to remove water from material); and/or physical forces, such as crushing or vibration (e.g., ultrasonic vibration). Other forces that can be applied include dehydrating the sample by heat or chemical means, applying temperature to the sample, applying mechanical pressure on the sample, mechanically rupturing some or all the sample, subjecting the sample to a chemical reaction, or a combination of any or all thereof, optionally in addition to applying one or more levels of vacuum and/or pressure to the sample.

In one aspect, the force is a vacuum pressure, such as the vacuum pressures described above. For example, a low pressure can be applied to a sample of the material as a means for causing one or more volatile substances to be detectably released from the material (or a vacuum can be applied that would increase the release of one or more volatile substances or gas(ses) from the sample if such a volatile substance is present). The precise amount of vacuum will vary depending on the material and other conditions of the method. Commonly the pressure will be below atmospheric pressure but greater than about $3\times10\text{-}4$ millibars. In another aspect, practicing a method of the invention comprises applying a vacuum to the sample at a pressure that is between atmospheric pressure and about $1\times10\text{-}3$ millibars. In yet another aspect, the method comprises applying a vacuum to the sample at a pressure that is between atmospheric pressure and about $25\times10\text{-}3$ millibars. In still another facet, practicing a method of the invention comprises applying a vacuum to the sample at a pressure that is between atmospheric pressure and about $1\times10\text{-}3$ millibars. In yet another aspect, the method comprises applying a vacuum to the sample at a pressure that is between atmospheric pressure and about $1\times10\text{-}2$ millibars. In still another sense, methods of the invention can comprise a step of applying a vacuum to the sample that is defined by a pressure of between about 1 to about 100 millibars.

In other particular aspects, the method comprises applying a positive pressure to the sample. A positive pressure can be any pressure that is in excess of ambient atmospheric pressure and that results in a measurable release of desired gas(ses) (at least under conditions in which volatile substances that form such gas(ses) are present in the sample). Positive pressure can be applied by any suitable means, such as, for example, using a piston. The method can include one or more applications of positive pressure, or the combination of application of positive pressure with any of the other methods described herein for aiding disrupting the sample and/or extracting fluids from the sample. The specific pressure applied will depend on the other conditions of the method, such as the nature of the material and whether other forces are applied to the sample. In one example, a pressure of about 400 to about 4000 pounds is exerted on the sample (e.g., about 1000 pounds to about 3500 pounds), although higher pressures also can be exerted by using certain methods available in the art, such as hydraulic pistons.

In another aspect, the method also or alternatively includes application of a physical force, such as crushing, abrasion, thermal decrepitation, grinding, and/or drilling. For example, materials can be loaded into a sample container comprising a crushable portion, such as a crushable sidewall, and the sample container can be subjected to crushing so as to promote the release of volatile materials. For example, as discussed elsewhere herein, samples that are or that comprise cuttings can include hydrocarbon materials contained in small fissures, pores, and other structures, which are distinguishable from fluid inclusions, by their exposure to the environment and/or in that they are characterized in not being hermetically sealed in an inclusion. These formations in geological material, which are also represented in cuttings taken from such material, can contain hydrocarbons, such as petroleum-related hydrocarbons, which are held in the geologic material. Application of a physical force, such as crushing, can assist in releasing such materials from such formations. Selection of the parameters for these methods will vary with the nature of the material, other parts of the analytical method, etc. A typical exemplary method of the invention will comprise crushing samples, such as cuttings, by about 400 pounds to about 4000 pounds, which can be achieved using some of the exemplary devices described herein.

It should be noted that in certain aspects of the invention no force is applied to the sample. In other words, just the exposure of the material to a release channel, such as a needle that penetrates a container in which a sample of the material is contained, can allow the gas to be exposed for performance of the next step of the method or to flow to either another container, portion of a device of the invention, or the like, wherein such other steps can be performed. For example, in one aspect, the gas that is released from the sample will flow to a gas trap device, such as a liquid nitrogen gas trap, such that a portion of the gas becomes trapped in the trap and thereafter can be released in a predictable manner.

In one embodiment, methods of the invention are characterized by the collection of the sample in a sealed container and by the subjecting the sample for an initial period to approximately the same pressure (e.g., within 90%, 95%, 99%, or more of the same condition) or exactly the same pressure (at least within limits of detection and/or condition, such as at atmospheric pressure without respect to natural fluctuations in such pressure) at which the sample was sealed in the sample container, such that a majority of the volatile materials are not lost when released from the container. Often this means that the sample will initially be subjected to atmospheric pressure.

In another aspect, in addition or alternative to crushing the sample, by the methods described elsewhere herein the methods can comprise mechanically rupturing some or all of the sample, subjecting the sample to a chemical reaction, or performing a combination of any thereof, alone or in combination with application of crushing, compression, or the like. In another facet of the invention it is characterized by the lack of any step that comprises application of heat (e.g., an increase of temperature of about 25% or more, about 35% or more, about 50% or more, about 75% or more, about 100% or more, etc.) for a period of more than about 12 hours, such as more than about 6 hours, more than about 4 hours, or more than about 2 hours.

In one aspect of the invention the method comprises isolating or "trapping" some portion of the gas released from the sample by contacting the released gas with a "gas trap" (which may also simply be called "a trap").

"Trapping" means that the trapped gas is collected and maintained or held in a device, medium, and/or location. Trapping in the context of these aspects of the invention typically occurs in a releasable manner, and commonly the gas is trapped in a manner such that parts of the trapped gas can be released from the trap in a predictable manner, such as when some kind of change is made to the condition of the trap. For example, in one aspect the trap is a material that bonds to some portion of the gas and the gas is released by changing the conditions of the bonding, for example, by increasing the temperature.

In a preferred aspect, the trap is a cryogenic trap, such as a liquid nitrogen trap, which traps gasses through freezing of volatile compounds onto a surface that has been cooled by liquid nitrogen or other cryogenic methods thereby freezing the volatile compound to the trap device or trap media. In such embodiments, the method can include the step of releasing of volatile compounds from the trap due to warming of the trap, thereby releasing volatile compounds from the trap in a predictable sequence for further analysis and/or treatment. Freezing traps can be operated under any suitable conditions. Typically, conditions will be selected based on the properties of the material to be trapped by the media or device used in the inventive method. In one aspect, the trap is a material or device that is cooled to about minus 50 degrees C. or less in the performance of the method (e.g., about minus 100 degrees C. or less, such as about minus 150 degrees C. or less, such as about minus 190-200 degrees C., although in some cases colder temperatures can be obtained and employed). Commonly, the cryogenic trap will be cooled to such a temperature prior to the exposure of the gas released from the sample to the trap. In this respect, as in some of the preferred devices described below for practicing the inventive methods, there may be one or more controllable valves that are used to controllably expose the sample-release gas to the trap, and the method correspondingly will include the step of exposing the trap to the sample-release gas in a controllable manner, after such cryogenic cooling.

Other types of traps may also be suitable for performing steps of the inventive methods. In one case the trap may be selective, in that it is either capable (or more capable) of selectively binding to certain materials and/or selectively not binding certain materials. In one case, for example, the trap is selected such that it is selective for not trapping water, carbon dioxide (or other compounds that might interfere with parts of the analysis, make analysis more difficult and/or less accurate), and/or make analysis take longer or cost more) and/or one or more organic acids, particularly if analysis of the organic acids is also a part of the method.

Typically, however, the trap used in the inventive method is a non-selective trap, at least with respect to target substances of interest. The term "non-selective trap" in the context of this invention typically means that the trap binds to all or substantially all of the volatile compounds present in the sample or all of the relevant volatile compounds that are present in the sample. The operation of such a non-selective trap can be contrasted with a selective trap, such as may be found in a gas chromatograph ("GC"), which binds to a certain compound or a class of compounds, but does not bind to other compounds. This is not to exclude application of GC technology in performing certain aspects of the invention, as aspects of the invention in which GC technology is used are described elsewhere herein and, as noted above, in certain cases selective traps, such as using a GC material (or set of such materials), could be part of a trap component of the invention, or could constitute the trap.

In aspects where the gas is subject to a trap, the material contained in or that is otherwise bound to the trap can be considered to form an "aliquot" that is used for further analysis according to various aspects of the invention.

As noted above, gas trapping devices, media, or systems, which can be used in various contexts of the invention, can be either selective or non-selective. In one aspect, the gas trapping device is a non-selective trap, capable of capturing gas containing a number of different types of volatile compounds, such as a cryogenic trap which freezes volatile compounds to fix them to a media. A liquid nitrogen trap is an example of such a cryogenic trap.

The gas released from the sample (or "first gas") will be allowed to contact the trap for any suitable period of time. The optimal time of contact will vary with the trap, the gasses that are present or expected to be present, and other factors. For cryogenic traps, such as the liquid nitrogen trap described above, the time of contact between the trap and the volatile substances can be relatively short, such as less than about a minute, and commonly less than about 45 seconds, usually less than about 30 seconds, and often as little as about 15 seconds, about 10 seconds, or less than about 10 seconds (such as 7, 6, or even 5 seconds) will be suitable. In certain cases, the trap will comprise a pumping function, such as in the case where the trap is a cryogenic trap/pump, which may occur by the action of freezing substances to the trap. In this respect, having conditions that cause freezing quickly can be important, as such quick freezing removes volatile compounds from the atmosphere surrounding the sample, which will, in turn, cause more volatile compounds to be released from the sample (as the system works towards equilibrium).

However, the entire period that gasses released from the sample are exposed to the trap will be significantly longer than these short periods, such as a period of about 10 minutes or longer, for example about 15 minutes or longer, about 20 minutes or longer, about 30 minutes or longer, about 40 minutes or longer, or about 60 minutes or longer. The amount of time of exposure depends on the pressure applied, the nature of the sample, and other factors. When, for example, seeking to release and analyze more refractory substance in the sample and/or when dealing with a particularly difficult sample material, longer times of application may be required, such as about 15 to about 30 minutes. However, in other aspects, the amount of time that is applied is about 10 minutes or less, such as about 8 minutes or less, about 6 minutes or less, or even about 5 minutes or less.

In some cases, where the method is performed with repeated cycles, the cycles can vary in terms of the amount of time in which gas is exposed to the trap. For example, in the first cycle of a method the time may be relatively shorter, such as less than about 10 minutes, where there may be more gas readily available in association with the cycle, whereas in subsequent cycles, where it is more difficult to extract gas from the sample, a longer period of time may be employed, such as about 10 minutes or longer, so as to permit the second cycle gasses to sufficiently bind to the trap.

In aspects in which an extended time prior to the warming of the liquid nitrogen trap is provided, the extended time is not solely to provide more time for the gasses to bind to the liquid nitrogen trap, but, rather, such an extended time can provide for improved extraction or liberation of volatile species from the sample. Thus, the liberation of volatile gasses from a sample can be, at least in some respects, considered to depend on the variables of the nature of the sample, the nature of the volatiles, the forces applied on the sample to promote release of such volatiles, and the time given to permit such release and/or collection of gasses. It is often preferred that all volatile fluids that are gaseous in the sample are collected prior to exposure to any vacuum. Where the sample contains volatile liquids, the application of vacuum to the sample, such as after "passive" (non-vacuum) collection of gaseous volatile substances from the sample, can be desired, inasmuch as such application of vacuum may lead to boiling of substantially all or all of such liquids, or at least result in the boiling of a substantial proportion of such volatile substances (at least 20%, at least 30%, or at least 33% of the amount); a majority of the substances; a substantial majority of the substances (at least 66.66%, at least 75%, at least 90%, at least 95%, at least 99%); or at least a detectable amount of such substances. In any case, the boiling of such volatiles that are normally liquid (at atmospheric pressure and typical ambient temperature) will render such boiled substances or boiled fraction of such substances gaseous. The length of time required to achieve a desired level of boiling of liquid substances in the sample is dependent on factors similar to those described above with respect to release of gaseous volatile compounds, but will primarily depend on the weight of the substance (heavier materials typically require longer to boil). Application of longer periods of vacuum, and resultant boiling, can, thus, result in the conversion of a significant amount of liquid volatiles into gaseous species for analysis in accordance with the inventive methods described herein. Thus, the certain aspects of the invention that comprise application of extended periods of time for release of gaseous volatile substances from a sample and/or application of vacuum to boil liquid volatile compounds in a sample provide the inventive methods a unique advantage over the prior art in that more of the volatile substances in a sample can be fully analyzed by allowing the time required for more of the volatile liquids to be released and/or captured.

In one aspect of the method, the change in temperature used to release gas species from the liquid nitrogen trap is performed in less time than flash warming methods used in gas chromatograph (GC) methods that also use liquid nitrogen trapping. Such GC methods use "flash" or rapid warming applied to a liquid nitrogen trap used in the GC method, which release many, most, or substantially all of the gasses trapped to the liquid nitrogen trap at once. GC methods also require that all of the gasses to be analyzed enter the GC media simultaneously, such as a trap if used in the method, nearly simultaneously, as the presence of all of the gasses to be analyzed at the same time is necessary for the effective performance of such analytical methods. These limitations are typically not required (or desired) for the inventive methods described herein, and as described elsewhere a gradual warming of the liquid nitrogen trap over a more sustained period of time to permit for the predictable release of trapped gasses is a common aspect of methods of the invention that comprise a trap, such as a liquid nitrogen trap. Also, this negates the need for any kind of separation of gasses other than the warming of the liquid nitrogen trap in these aspects of the invention. Thus, in another facet of the invention, the invention lacks any step of molecular selection, such as molecular distillation or similar method, being performed on the substances to be analyzed in the method.

In some aspects, a relatively high vacuum can be applied to a trap or applied in the device or system used to carry out the inventive method such that the trap is under vacuum conditions for a period of time. For example, in some cases where a relatively high vacuum is applied to a sample that vacuum also may be applied through other parts of the system, including the trap. In other aspects, the method also or alternatively comprises a method in which vacuum is applied to capture non-condensable gasses and remove such material from contact with the trap (or to at least substantially achieve such a state).

In certain aspects, such as where relatively high vacuum is applied to the trap or in the system such that a vacuum condition is present at the trap for a period, it can be advantageous to continue to reinforce the trap media or device with whatever substance is used to trap the target gasses, such that gasses that might be easily/readily released from the trap are maintained in contact with the trap. For example, in the case of a liquid nitrogen trap the method can comprise continuously applying liquid nitrogen to the trap while the vacuum condition is present so as to retain substance of interest (e.g., ethane, ethene, etc.) trapped into the trap until they are ready for release in a predictable manner.

Another action that can form part of the methods of the invention is the step of isolating the aliquot from the sample. Commonly, once gasses are collected from the sample to form an aliquot, that aliquot can then be isolated from the sample, such that the remainder of the analysis of the method or at least that step or part of the method is conducted on the aliquot without further collection of gas from the sample for the collection of the present aliquot (or if this is the final aliquot or only a single aliquot is being collected for the particular application of the method). This method of isolating can be performed for many reasons and using any suitable technique. Where devices of the invention described elsewhere herein are used in the practice of the method, for example, one or more valves may be engaged, which results in isolating the gas of the aliquot from the sample. The method also or alternatively can include the step of isolating the trapped gasses from access to other components of the device or system in which the trap is situated. For example, where the method is performed with a device of the invention that comprises (a) a sample holding unit, (b) a gas trap, and (c) a mass spectrometer, the method typically will comprise the step of isolating the gas trap from both the sample holding unit and the mass spectrometer for one or more periods of time (e.g., isolating the trap from the samples after a sufficient passage of time and/or application of conditions necessary to collect gasses from the sample and isolating the mass spectrometer until it is time to release the gasses from the trap to it for analysis).

In aspects of the invention in which one or more gasses released from the sample are subjected to a trap to form an aliquot, the method typically includes the step of releasing volatile substances from the aliquot as trap-released gasses in a predictable sequence. For example, where the sample is comprised of one or more drill cuttings obtained from an oil well site, gas is obtained from cuttings, either passively or by the application of one or more forces, such as mechanical crushing and/or application of one or more vacuum pressures on the sample, and then subjected to a trap, such as a liquid nitrogen trap. Much of the gas from the cutting samples will be captured by the trap. Allowing the trap to heat, either passively, or, more typically through the application of heat, directly or indirectly, to the trap, will allow for volatile substances in the gas that are frozen to the trap to be released in a predictable manner.

A "predictable manner" means that substances such as individual volatile gasses or mixtures or other types of volatile gas species are released from the trap in a manner such that if gasses are present their release can be predicted from the timing and/or condition of their release. For example, in one aspect a predictable manner means that different species are released as a function of time. In many aspects, the release of species can overlap the release of other species, such that, for example, there may be first period of release of one or more first species (e.g., lighter or more volatile compounds), a second period in which there is a release of one or more second species (e.g., heavier or less volatile compounds), and an intervening period in which both the one or more first species and one or more second species are both being released. In many aspects, there will be several such periods and intervening periods. The periods and intervening periods may, however, form a predictable pattern of release such that if expected compounds are present in the sample it will be known to expect them to release at a certain time and/or under the application of a certain condition.

Another step of the inventive methods also or alternatively analyzing gasses that are directly released from samples, typically after the application of an energy to the gas, to break down (decompose) substances in the gas, thereby turning volatile species in the gas to target substances for analysis. For example, such a method of the invention can comprise taking a volume of a sample, such as cuttings, optionally applying one or more forces to the sample so as to release one or more endogenous volatile gasses (such as formic acid, acetic acid, carbonic acid; or other organic acid), applying an energy source to volatile gasses so as to break down the volatile species to one or more target compounds (such as carbon monoxide), and analyzing the target compounds to determine whether the endogenous volatile substances were present, particularly if the presence of such endogenous substances are indicative of the presence of petroleum or another material that is desired. In such methods, optionally no trapping of a gas is performed and/or no mass spectrometry or similar method is applied. This aspect of the invention provides simple methods that can be readily performed with limited amounts of equipment, while still providing a sufficient indicator that petroleum or another target substance is in the relevant formation associated with the sample.

The amount of energy to be applied can be any suitable amount of energy and/or force to break down the volatile substances into the target substances. In one aspect, the invention comprises applying heat of about 400 degrees C. or higher or another temperature or condition so as to disassociate formic acid, carbonic acid, or both (in one aspect, carbonic acid only) to one or more components thereof, such as carbon monoxide and/or carbon dioxide. In another aspect, the method comprises applying a vacuum to the sample to assist or handle the breakdown of the endogenous volatile substances into the target gas(ses). Vacuum conditions described elsewhere herein have been associated with such breakdown of endogenous gasses and may be applied in this aspect as well. In still another aspect, the invention also or alternatively comprises contacting the sample with one or more chemicals that assist in the release of the target gasses from the endogenous gasses, such as application of a desiccant. Another aspect comprises application of radiation, such as microwaves, to the sample, to aid with the breakdown of the endogenous gasses.

The methods of the invention also include the step of analyzing gasses generated or released in the various methods (e.g., trap-released gasses or decomposed gasses generated where no trapping is performed), so as to determine if substances of interest are present in the formation or material from which the sample was taken or with which the sample was associated. Any suitable type of analysis can be applied to such gasses and any suitable combination of methods can be applied as well, if desired and possible.

A preferred aspect of the inventive methods described herein comprises the application of mass spectrometry analysis to trap-released gasses. Any suitable type of mass spectrometry method can be used in this respect.

When performed in the practice of the invention, a mass spectrometry method typically will be selected to be suitable for the identification of expected or desired target substances. For example, if the desired task is to identify the presence of petroleum-relevant hydrocarbons and/or organic acids and/or inorganic gasses (e.g., $H_2S$, helium, and $CO_2$) in cuttings obtained from an oil well, the mass spectrometer will be selected and operated such that it can identify, among other things, volatile gasses such as octanes, nonanes, and larger hydrocarbons that are indicative of the presence of petroleum in the geological formation from which the cuttings originated. Mass spectrometry is typically a preferred method as it works rapidly and provides a useful, detailed level of analysis. There are a variety of mass spectrometry devices that can be used in performing methods involving mass spectrometry. A quadrupole mass spectrometer (residual gas analyzers (RGAs)), for example, are readily available devices, which might be suitable for many of the methods described herein. Time of flight mass spectrometers, which provide rapid analysis, also may be suitable in many instances. More complex systems, such as mass spec/mass spec (dual mass spectrometers/triple quads) also could be used in some cases and may be advantageous for better resolving substances with masses that are similar to other substances which may be present.

Mass spectrometry is not a required component of the invention, however, as other analytical methods can be used to analyze samples in accordance with the invention. Flame Ionization Detection could be used for analysis of various hydrocarbon species. Gas chromatography also or alternatively can be used to analyze gasses in certain aspects of the invention. It also or alternatively may be possible to analyze hydrocarbons via infrared spectroscopy or Raman spectroscopy.

Other times simpler methods can be used in the place of mass spectrometry or such sophisticated methods, such as gas chromatography. In important aspects of the invention the invention comprises detecting the formation of target substances which are released from organic acids, such as carbon dioxide or carbon monoxide, which can be detected using conventional, commercially available detection devices or the technology in such devices. Pressure release, for example, may also or alternatively be used as an indicator in some methods. Water release could simply be measured using a humidity meter, and also or alternatively provide relevant information in certain aspects of the invention.

Although the methods of the invention can be performed with various approaches, in some aspects methods can be characterized by steps that are not performed and/or the components that are absent from a device or system of the invention. For example, one aspect of the invention is characterized by the lack of any gas chromatography step in the method (or, correspondingly, by the lack of such device/ component in the system/device of the invention). Other steps that may be excluded from the methods of the invention include infrared analysis. It will be understood that generally the principles described herein with respect to the methods of the invention will implicitly carry over to the devices and systems of the invention, such that this description should also be interpreted as disclosing devices and systems lacking infrared capabilities.

In aspects of the invention where a trap is used, another optional step of the inventive method is collection and analysis of non-condensable gasses (i.e., gasses that will not condense and securely bind to the trap, and/or other materials from the sample) ("NCGs"). In some aspects, application of one or more other steps of the method may generate materials that will not bind to the gas trap. For example, where a liquid nitrogen gas trap is used some materials may not be too volatile and/or some gasses may not bind the trap or at least not bind to the trap completely or bind to the trap in sufficient quantities to indicate an accurate amount of the material or even to indicate the presence of the material at all in the sample. In such cases the method can include collecting non-condensable materials and/or non-binding gasses. These materials may be collected, such as by applying a collection method to isolate such material for later analysis. In the use of devices of the invention, the device can include a mechanism for collecting such materials in a manner that isolates them from the rest of the material to be analyzed. A vacuum can be applied to gasses that are not bound by a trap, for example, to collect such gasses. Ideally such gasses are isolated and captured in a container or structure functioning as a container in a device and then selectively subjected to analysis before or after analysis of the trapped gasses. In some aspects, the NCG material may be in too great a quantity for analysis and the method will comprise a step of limiting the amount of NCG material that is analyzed and/or controlling the rate of analysis of the NCG material.

In some aspects, the methods of the invention can include the step of repeating various steps of the method. For example, in one aspect the invention provides methods comprising a cycle of repeatedly applying one or more forces to the sample to cause or assist in the release of volatile compounds from the sample. Such methods can include the repeated application of the same type of force or applications of two or more different forces or the application of the same type of force but in a different amount, duration, etc. For example, in one aspect the invention provides methods in which vacuum is applied to the sample several times, at different pressures, for different periods, or both. In some aspects, gasses expected to contain certain volatiles under this condition are the target of one or more analytical methods practiced on the gasses or on trapped gasses generated from the sample-released gasses. Such methods typically also will include multiple steps of capturing the multiple gas aliquots generated by application of the multiple forces, releasing such respective gasses, and analyzing such released gasses, which can then be examined in combination to obtain a profile for the sample.

Analysis of substances by the methods of the invention can be qualitative (determining the presence, but not the amount), quantitative, or both. Methods of the invention in which trapping and predictable release of trapped gasses occur are particularly amenable to quantification. In one aspect, the invention provides a method that is capable of quantifying the amount of one or more volatile compounds contained in the sample. Quantification can be performed through analysis against a standard. For example, a standard of a gas at a known volume and known pressure can be generated and a sample can be compared to this standard. Similarly, a drop of a liquid of known volume and composition can be analyzed by the method employed and then the result(s) from the sample(s) compared to such a standard. Standard compositions are typically comprised of a NCG, such as nitrogen (e.g., at least about 80% is nitrogen or at least about 85%, at least about 90%, or more of the standard is nitrogen and/or methane), with the small remaining amount comprising a known amount of one or more hydrocarbons, which will be released from the trap at different temperatures, and allowing for quick analysis of the standard material. Because standards may not be contained in a material such a cutting the method may comprise controlling the volume and/or rate of release of material analyzed (e.g., by using a needle or constricting passageway to control the flow of the sample material to the analytical components of the system).

Methods of the invention can comprise analyzing the sample for the presence of organic acids and/or hydrocarbons, with the analysis of the presence of organic acids (which typically is done by analyzing for the presence of other target substances, such as carbon monoxide, which indicate such organic acids are present) typically being preferred or selected if only one of the two are analyzed. Nonetheless, the analysis of hydrocarbons also can be important. For example, analysis of C5-C10 hydrocarbons in the sample can provide information about the entire volume of petroleum in a formation, once the presence of petroleum is established by identifying target substances that indicate the presence of petroleum-associated organic acids (e.g., formic acid and/or carbonic acid, or only carbonic acid). Where samples sealed at the well or other collection site are analyzed in the method of the invention, hydrocarbon data can directly correspond to the presence of oil in the associated formation. In the case of old, non-sealed samples, hydrocarbons are likely to be associated with fluid inclusions only, and the presence of hydrocarbons alone in such materials may not be sufficient to accurately identify the presence of petroleum in the formation in question.

In one aspect, the analytical method comprises analyzing the amount of water in the analyzed gasses (e.g., the trap-released gas in a method in which gasses are trapped and released). I have surprisingly discovered that high water concentration (in geologic material and/or in a sample of such material) can be an indicator of oil saturation. While not wishing to be bound by any particular theory, I believe that one or more organic acids, such as carbonic acid, formic acid, and/or acetic acid, which is/are present in cuttings or samples will break down in the performance of certain aspects of the inventive method thereby generating more water than would ordinarily be present in the sample (e.g., from analysis of such cuttings by extraction of gas therefrom containing volatile compounds, capturing such gasses on a liquid nitrogen trap, releasing such gasses from the liquid nitrogen trap in a predictable manner, such as through accelerated warming of the liquid nitrogen trap, and subjecting the released gasses to mass spectrometry analysis). However, in other aspects of the invention, other compounds than water are also or alternatively analyzed to assess the sample. This is particularly true as other organic acids associated with samples may not release water.

In one aspect of the invention, detection of excess water associated with a sample as an indication of petroleum-associated hydrocarbons is made under conditions in which petroleum compound-associated excess water in the sample can be detected and distinguished from other water in the environment. For example, in aspects of the invention in which a liquid nitrogen trap is used in the method and/or incorporated into the device/system of the invention, the observation of water at temperatures below that which normal water release is expected. Thus, for example, in one aspect the method comprises the detection of water at a temperature that is significantly colder than −55 degrees C. (a temperature representing about the lowest temperature at which water would typically be expected to be released and detected), such as a temperature of about −70 degrees C. or less (colder), about −80 degrees C. or less, about −100 degrees C. or less, about −110 degrees C. or less, about −120 degrees C. or less, or even cold temperatures, such as about −130 degrees C. or even about −140 degrees C. (e.g., about −100 degrees C. to about −200 degrees C., such as about −120 degrees C. to about −180 degrees C.). In experiments conducted with systems of the invention, such as the system exemplified in FIG. 1, water can be detected when released at temperatures of about −140 degrees C. (a temperature normally associated with a carbon dioxide peak/release) and at higher temperatures (present in the system when the system is allowed to warm or is warmed by the application of heat from heaters in or on the system), but above −55 degrees C. Typically, the detection of water by a mass spectrometry system will occur in a plurality of distinct peaks associated with such temperature increases, ranging from about −140 degrees C. to about −55 degrees C. in such a system/device. Without being bound by theory, it is believed that the detection of water under such abnormally cold conditions reflects the breakdown of organic acid compounds during or after release from the trap and/or from water generated by acid decomposition by ion fragmentation resulting from electron bombardment under high vacuum in the mass spectrometer. In any event, the detection of water under such cold conditions, especially when combined with conditions that would lead to and/or permit the decomposition of organic acids associated with samples, such as petroleum well-associated cuttings, is another important aspect of the invention.

In particular aspects, if the water evolution (generation) caused by acid decomposition occurs during, or after, acid release from the liquid nitrogen trap then some of the water, but typically less than all of the water, created by acid decomposition may be re-trapped on the LN2 trap, but the remainder of that newly formed water escapes the trap and is analyzed. Other noncondensable gasses that form from the acids' decompositions, e.g., methane from acetic acid and carbon monoxide from formic acid, typically are not trapped back onto the trap, but are usually transported and analyzed in the mass spectrometer upon the acid's evolution from the trap.

The separation of water evolved from acid breakdown from normal water via evolution from a trap, for example a cryogenic trap such as a liquid nitrogen trap, has not been previously described by others, and this phenomenon is a unique advantage of this invention. As discussed herein mapping of oil and gas associated acids using water and other indicator compounds is a unique feature of this invention and has many applications for oil and gas exploration and production.

In yet another aspect, the method comprises a $P_2O_5$-based analysis of the water content of one or more samples analyzed in the method. Gas from a sample (typically after heating to drive water off the rock before release of the gas) can be transferred around/over a $P_2O_5$-containing apparatus or container (with a known weight) and the weight thereafter measured to determine the amount of water present in the sample. Such methods can be advantageously performed on water in fluid inclusions as part of the inventive method, as water can be difficult to analyze in the context of analyzing fluid inclusions.

In one aspect, the method includes using hydrocarbon-containing fluid inclusions as a negative indicator of the presence of oil. In certain aspects the presence of hydrocarbon-containing fluid inclusions is a negative indicator of the presence of oil in a material and the presence of a low number of hydrocarbon-containing fluid inclusions, particularly immediately adjacent, usually overlying, a zone of abundant oil and gas fluid inclusions, is typically indicative of a high chance of oil in the material. Such analysis can be included as part of the inventive methods described herein, and, in and of itself, represents an aspect of the invention. Thus, for example, the invention provides a method of oil pay zone mapping by solely or in combination with other methods examining the number of hydrocarbon-containing fluid inclusions in a material and identifying areas where the number of petroleum-relevant hydrocarbon fluid inclusions are relatively low (less than about 10% of the number, e.g., less than about 5% of the number, of fluid inclusions in water-associated areas, such as a water leg) or not detectable as areas having a high likelihood of representing oil pay zones. Of course, this is not true for the pore fluids (present day fluids present at the site), which can be analyzed by the other aspects of the invention.

In another aspect of the invention the method comprises the step of analyzing released gasses for carbon dioxide. Carbon dioxide, like water, can be produced from the breakdown of organic acids contained in the sample. In other aspects, this step is avoided, as may also or alternatively be the case with respect to analyzing for the generation of water. This is because either substance, and particularly carbon dioxide, can be confused with other sources of the substance, which may make the analysis more difficult. Nonetheless, in certain instances the analysis of carbon dioxide in the analyzed gasses, is an aspect of the invention.

In another respect, methods of the invention can comprise analyzing the analyzed gasses for the presence of carbon monoxide, which can be indicative of formic acid being present in the sample (and, thus, useful in mapping of oil pay zones). Carbon monoxide can be detected using conventional carbon monoxide detection devices, which are commercially available, or by using technology similar to that which is employed in such devices. The carbon monoxide detection can be used to identify pay zones within a well, where areas of a well associated with a relatively high amount of carbon monoxide indicate the presence of petroleum in such an area (e.g., at a certain depth of a well). Within a well, the presence of about 35% or more, such as about 50% or more of the maximum detected amount of carbon monoxide (which can be set as 100%) is typically indicative of a petroleum-relevant amount of carbonic acid and/or formic acid, typically formic acid, at such site (in some cases, the method is focused on the identification of the presence of carbonic and/or formic acid, typically formic acid, which will be indicative of the presence of oil in the sample and related material).

In another facet, the invention provides methods for determining the permeability of a formation or composition. Such methods typically require a multiple aliquot method applied to samples under different conditions, such as different pressures, so as to assess the permeability of the sample (and, correspondingly, the formation).

Such methods are typically performed with samples primarily or entirely containing non-fluid inclusion volatile substances. In other aspects, the methods are performed in materials comprising fluid inclusions.

A sample can be, for example, subjected to different pressures to release different aliquots, and each respective aliquot analyzed for one more substances, such as hexane (or methane, propane, pentane, etc.). The relative amounts of the target material released under both conditions is analyzed with the output of the analysis being indicative of the permeability of the sample (and thus the formation). The analysis of such methods can at first appear counter-intuitive, this is because many samples, such as cuttings, can either be highly permeable, relatively impermeable, or contain zones of both high and low permeability. For example, with respect to hexane, if the application of a first and relatively weaker vacuum results in a relatively large amount of hexane being released from the sample and analyzed (compared to the second aliquot performed under a stronger vacuum), this result will typically be indicative of low permeability of the sample. This surprising outcome is because most of the petroleum-related hydrocarbons that could be lost in the first aliquot in such material will be lost between the generation of the sample (e.g., the drilling that produced the cutting) and the analysis of the sample for high permeability samples. Therefore, if a greater amount of hexane or other relevant target substance is released and analyzed when the first vacuum condition is applied such a result indicates that the permeability of the sample is relatively low, because the hexane was not lost between generation of the sample and analysis. If the sample has relatively greater permeability it typically will release more hexane on the application of a strong vacuum, because only the material in the sample with low permeability will release hexane at such time. Thus, the proportion of hexane or other target substance released from a first aliquot and a second aliquot by methods of the invention can be compared to provide an indication of permeability of the sample is another aspect of the invention. The other gases analyzed besides hexanes can also be used in evaluating permeability. In fact, it can be useful to study the relative permeabilities of the various volatile constituents of the sample.

In other aspects, permeability can be assessed by infusing the sample with a substance, such as a noble gas, and then measuring the release of that infused substance, alone or in combination with the release of endogenous volatile substances, such as hexane.

In one aspect, the invention provides a method of determining permeability of a material by comparing the release of one or more volatile substances and/or classes of volatile substances from the same sample from the material under two or more different conditions that promote the release of volatile substances from the sample, such as applying two different pressures to a single sample. In some aspects, this process is applied to a plurality of samples, such as at least 10, at least 20, at least 50, at least 100, at least 250, at least 500, or even at least 1,000 samples. In some facets, at least three conditions, at least four conditions, at least five conditions, or more are applied to a single sample to aid in the assessment of permeability.

In one example of the permeability evaluation method described above, a first aliquot is extracted from a sample, such as a cutting from an oil well, at a pressure of about 50 millibars. A second aliquot can then be extracted from the same sample at a pressure of about 5 millibars. Permeability can then be estimated by comparing the data obtained from these two analyses. In other words, the force required to extract volatiles out of a sample can aid in the determination of permeability. This is of further significance in that conventional permeability measurements cannot be performed on cuttings samples, but, rather, are typically applied on conventional core or rotary side wall core samples and are based on the pressure required to push a fluid through a uniformly shaped piece of rock, usually a cylinder. Typical fluids used in conventional permeability measurements include helium and mercury. Such permeability measurements cannot be applied to well cuttings as they require a coherent volume of intact rock.

A formula that can be useful in estimating the permeability using hexanes in accordance with the above-described aspects of the invention is: $100*(\text{hexanes}^{aliquot\ 2}-\text{hexanes}^{aliquot\ 1})/(\text{hexanes}^{aliquot\ 2}+\text{hexanes}^{aliquot\ 1})$. In one aspect, this formula is used in the determination of permeability. Values obtained from this expression range from 100 to −100. A value of 100 indicates hexanes were only obtained from aliquot 2 in a 2-aliquot analysis with no hexanes analyzed in aliquot 1, these are the most permeable samples. A value of −100 indicates hexanes were only obtained from aliquot 1 with no hexanes analyzed in aliquot 2, these are the least permeable or the tightest samples.

The nature of the calculation reflects an unexpected aspect of the invention. Ordinarily it would be expected that the most permeable samples will have high hexanes on aliquot 1 and low hexanes on aliquot 2. This however is not the case. I have surprisingly discovered that in the most permeable samples the most easily removed hexanes are lost between the time the rock is disrupted by the drill bit and its rise to the surface suspended in the drilling mud, until the sample is sealed in a brass tube either at the well site, or at some later time. Hence, the most permeable samples show the least amount of hexanes from aliquot 1 and the most amount of hexanes from aliquot 2, in the type of method descried here. Thus, a sample that shows high hexanes on aliquot 1 and low hexanes on aliquot 2 is a sample with very low permeability such that hexanes are not predominantly lost from the sample by drill bit disaggregation and transport to the surface in the drilling mud at residence time under atmospheric conditions before being sealed in a container, such as a brass sample tube, and analyzed.

Permeability in samples analyzed according to these aspects of the invention can vary as a function of compound size, shape, mass, and chemical affinities. It is therefore instructive to consider a range of permeabilities using several of the compounds that are analyzed, or all of the compounds that are analyzed. Hexanes can be a preferred measure of permeability for the method (or inclusion in the method) because under natural conditions prior to analyses the hexanes should be liquids. And under all analytical conditions used in our analyses the hexanes should be gaseous. This then removes any possibility with confusing boiling for permeability.

As mentioned elsewhere herein, in some aspects, the method of the invention comprises analyzing the presence of hydrocarbons. In some cases, the method comprises the analysis of short hydrocarbon chain molecules. In other aspects, the method comprises analyzing both long chain and short chain hydrocarbon molecules. For example, C2-C15 hydrocarbons, such as C2-C12 hydrocarbons, e.g., C2-C10 hydrocarbons can be trapped and analyzed using a cryogenic trap method, and methane can be collected and analyzed using NCG methods described elsewhere herein.

The analysis of long chain hydrocarbons is another facet of the invention which distinguishes it from prior art methods which are typically performed very quickly and, thus, are incapable of analyzing such materials effectively, in that such methods do not sufficiently cause longer chain hydrocarbons to be released from samples. Where a longer period of time is used to trap materials, such as where a cryogenic trap/pump is employed for about 10 minutes or longer, such as about 12 minutes or longer, or about 15 minutes or longer, relatively longer chain hydrocarbons can be capture and then analyzed by the method, which is another distinguishing characteristic of such methods from the prior art. Relatively longer chain hydrocarbons means hydrocarbons comprising a backbone of six or more carbon atoms, such as seven or more carbon atoms or eight or more carbon atoms.

In a further aspect, the invention comprises consideration of pressure changes in the performance of the method. Methods of the invention can comprise the breakdown of compounds, such as organic acids (e.g., formic acid, carbonic acid, or acetic acid) to other compounds (e.g., carbon monoxide and water in the case of, e.g., carbonic acid, or methane and carbon dioxide in the case of, e.g., acetic acid), which can result in changes (typically increases) in pressure in the system because of the generation of such non-condensable gasses (carbon monoxide and methane).

In still a further facet of the invention, methods in which changes in moisture are performed on samples are provided, particularly after such samples are subject to conditions in which organic acids, such as formic acid or carbonic acid, can be formed, particularly from materials present in the sample. For example, in one aspect the method comprise subjecting samples to conditions that can form carbonic acid, which may be associated with and/or may further be broken down under such conditions or other conditions achieved in the performance of the method to form water, wherein the presence of such generated water is indicative of the carbonic acid or formation of the carbonic acid, and thereby indicative of the presence of oil-related hydrocarbons in the sample (and the material). For example, subjecting oil well cuttings to methods described herein wherein gas is released from the cutting, such as under varying degrees of vacuum pressure, trapped by a liquid nitrogen trap or a similar device, and released from such a trap to mass spectrometry analysis, water can be formed, and such water can be detected by any type of conventional method, including humidity or moisture detection techniques that are known in the art. The detection of water can, in some contexts, provide an indication that oil-related hydrocarbons are present in the sample and material and thus the method can comprise running an analysis for changes in moisture, humidity, or otherwise detecting changes in water content, following application of such methods or forces on the sample.

In another aspect, the invention comprises analyzing the effects of pressure in the formation by examining the sample for the effects of formation pressures. In such aspects, typically a number of samples from different areas or depths are obtained and examined for changes in fluid composition, which can be indicative of a discrete/large change in hydrostatic pressure between the different areas of the formation (e.g., from a zone of unusually high pressure to normal pressure or from a zone of normal pressure to a zone of unusually low pressure), which can be relevant to how materials in the formation will behave under different conditions.

Any of the analytical methods described herein that can be applied to analyzed gasses in the methods of the invention can be, and often are, combined, to provide a more complete analysis. For example, in one aspect the method includes the step of analyzing the analyzed gas for the presence of carbon monoxide, increased water content, and/or presence of C5-C10 hydrocarbons. In another exemplary aspect, the method comprises analyzing the analyzed gas for the presence of carbon monoxide and carbon dioxide.

The methods described above can be practiced with or without the application of other methods used for the identification, assessment, and/or characterization of formations and/or materials therein, such as the petroleum content of a formation. For example, in one facet of the invention, the inventive methods described herein are applied without performing conventional fluid inclusion analysis or gas chromatographic analysis of the material or sample. However, in another dimension, the methods of the invention can be performed in combination with such other conventional analytical methods, so as to potentially enrich the information gathered about the material. Another method that can be combined with these methods is to examine samples for fluorescence data which can provide evidence of oil staining of the sample.

In one exemplary aspect, the invention comprises combining information gathered from the primary methods described herein with information gathered from fluid inclusion analysis. Methods of performing fluid inclusion analysis are described in my previous patents referenced and described elsewhere herein. In one aspect that may be particularly advantageous in certain contexts, the method comprises performing a fluid inclusion analysis that comprises analyzing fluid inclusion-trapped oxygen, nitrogen, or the combination thereof, which are associated with the material. These non-condensable gasses can provide information about the paleontological (paleo-exposure) surface of the material, which may assist with, for example, oil exploration.

In still another aspect, the methods are practiced in combination with gamma ray mapping for, e.g., identification of types of geologic formation, e.g., identification of sands vs. shales. Including gamma ray mapping as a component of the analytical method can determine the nature of the formation material (sand vs. shale). The size of a formation can be relevant to assessing whether the deposit of the material (e.g., oil) is of sufficient amount to be economically advantageous for producing the material (again, typically oil) from the formation.

In another, more general sense, the invention provides methods of analyzing the content, such as the organic acid content and/or water content, of cuttings that were intimately associated with drilling muds, for example, to perform oil pay zone mapping. In fact, generation of oil pay zone mapping is a preferred and particularly advantageous application of this and other methods of the invention. Most cuttings from oil well sites will be intimately associated with drilling muds (an exception is an air drilled cutting). I have discovered that such cuttings can provide a unique opportunity for analysis of drilling areas. While not intending to be bound by any particular theory, I believe that the interface between such cuttings and drilling muds will form physiochemical structures that retain organic acid contents and possibly other contents, due to the normal differences in pH of the respective materials (mud and cuttings). Accordingly, methods of petroleum analysis, and pay zone mapping, comprising preferentially using such materials, is an important aspect of my invention. The methods that can be used to analyze the organic acid content of such cuttings can be any of the methods that are described herein or that otherwise are known in the art. What characterizes the methods of this particular aspect of the invention is that the method, at least in part, focuses on cuttings that have had such intimate interactions, thereby likely forming such unique conditions for maintaining their organic acid content. Again, the application of methods of this invention to determine the organic acid of such cuttings is particularly useful in pay zone mapping. This is because such organic acids are typically in cuttings that are co-located with petroleum in many geological formations.

One of the advantageous aspects of the inventive methods described herein is the application of the invention (such as the analysis of organic acid content) using samples obtained from fresh water environments (environments in which the water associated with most, substantially all, or all of the samples analyzed contains relatively little or no salt). For example, in certain aspects the method is performed with water having a saline content of less than about 10,000 ppm, such as less than about 5,000 ppm, such as less than about 2500 ppm. In this respect, the organic acid content analysis methods of the invention can work under conditions where conventional well logging methods fail, due to the nature of the fresh (low saline) water present at such sites.

In still another aspect of the invention, mud-associated cuttings have retained or captured water/brine from the site at which the cuttings are generated, and the method comprises analyzing the water/brine associated with such mud-associated cuttings, for example by analyzing the conductivity of such water/brine. Again, most cuttings will be mud associated when taken from petroleum drilling sites.

These amounts of water/brine are typically small and the method may comprise freezing such micro-amounts of water and then subjecting them to a suitable method for analysis, such as scanning electron microscopy with energy dispersive x-ray fluorescence, electron microprobe, and/or an ion probe, or other suitable method, to analyze the water/brine composition of the water in such cuttings. Such data can be used by petrophysicists to evaluate the oil and water saturation of a well as currently determined by conventional well logging methods. This and other such information that is obtained from such mud-associated cuttings can be used to map the presence of oil or other substances from such samples, and, thus, can be used as another method to perform "pay zone mapping", in accordance with the invention. In one aspect, the method comprises only analyzing such brine/water content. These methods can be particularly important in that resistivity (which today is successfully based on the presence of brine in a material) currently is commonly used as a key quantifier of petroleum content of drilling sites and other geological formations.

The methods of the invention that involve the analysis of volatile substances can be performed with any suitable number of aliquots taken from any suitable number of samples. In some cases, it can be advantageous to take a single aliquot from each sample in a set of samples. Thus, the invention provides a method in which a suitable sample is provided, the sample is subjected or exposed to forces that cause release of a gas containing an analyzable amount of one or more volatile substances, and the method includes the step of capturing (e.g., trapping and concentrating) a first trappable gas (such as a condensable gas in a system that relies on condensation of the gas) in or with a media or other means in an analyzable amount to generate an aliquot, optionally but typically isolating the sample from the aliquot, and optionally but typically releasing at least an analyzable amount of the volatile substances from the trap or collecting means, and thereafter analyzing at least one aspect of the chemistry of the one or more released volatile substances. Often it will be the case that the "single aliquot" will actually comprise a condensable gas component (sub-aliquot) that is trapped with a first trap and a non-condensable gas component (sub-aliquot) that typically is separately collected and/or separately analyzed from the condensable gas sub-aliquot.

The forces applied or to which the sample are exposed can be any suitable forces, such as those described above. In one set of facets, the method comprises subjecting the sample to a pressure of at least 1 millibar and less than 1 atmosphere, such as between at least 1 millibar to about 100 millibars. The sample can be exposed to such forces for any suitable amount of time. Particularly unique aspects of the invention comprise applying a gentle vacuum pressure, such as between about 1 millibar and about 500 millibars, such as about 1-300 millibars, about 1-250 millibars, about 1-200 millibars or about 2-200, 2-150, 2-100, 3-200, 3-250, 3-100, 5-250, 5-200, 5-100, 1-50, 2-50, 3-50, or 5-50 millibars of pressure for a period of less than 15 minutes, such as less than 10 minutes, such as less than about 9 minutes, less than about 8.5 minutes, less than about 8 minutes, less than about 7 minutes, less than about 5 minutes, or even less than about 3 minutes, less than about 2 minutes, or less than about 1.5 minutes or less than about 1 minute, such as about 0.25-15 minutes, about 0.33-12 minutes, about 0.5-12 minutes, about 0.33-10 minutes, about 0.33-11 minutes, about 0.5-11 minutes, about 0.5-10 minutes, about 0.65-about 11 minutes, about 0.65-10 minutes, about 0.5-7.5 minutes, about 0.33-7 minutes, about 0.5-5 minutes, about 0.33-5 minutes, about 0.75-7.5 minutes, about 0.75-5 minutes, or about 1-10 minutes, such as about 1.5-9.5 minutes, such as about 2-9 minutes, such as about 4-8.5 minutes, such as about 5-8.5 minutes, or such as about 6-8.5 minutes. The sample also or alternatively can be exposed to other forces comprises, such as subjecting the sample to a crushing force, optionally in addition to one or more other forces such as vacuum pressure, vibrational energy, or radiation energy, such as laser excitation, or a combination of any or all thereof. Application of crushing forces can provide a frackability aspect to the method, in which measures such as ductility and/or hardness are determined (e.g., by crushing a flexible container comprising the sample) as described above. The volatile substances can be analyzed by any suitable means, typically by means that comprise mass spectrometric analysis. In some aspects, the method can comprise removing potentially interfering gasses from the media, but in other aspects such a step is not practiced or is not necessary. In some cases these methods are characterized by not heating samples to temperatures of greater than 100° C. in performance of the method. In some aspects, the method comprises collecting and sealing samples at the wells versus loaded in lab samples. Such methods can comprise collecting and analyzing samples in close proximity to the well site. For example, the method can comprise performing the method within 200 feet, such as within 100 ft, 75 ft, or even 50 ft of where the samples are delivered to the surface. The method may comprise transfer of the samples by conveyor, pneumatic tube system, or other system to a site, or even delivery by drone, to a laboratory for analysis, which may be situated within 0.5 miles, such as within 0.25 miles or even 0.1 miles of the well site.

In another aspect, these methods are performed in relation to an active well, such as a well that is under active drilling, such that the method can provide real-time or near real-time analysis of samples. For example, in some aspects the difference or lag time between the site of drilling (location of the drill bit) and the location of the samples in which the most recent analysis is performed is than about 50 feet, such as less than about 40 feet, less than about 30 feet, less than about 20 feet, or less than about 10 feet, 7 feet, 5 feet, or even less than about 1 foot. Such methods may comprise actually collecting samples in the well line and, e.g., transmitting the data connected with the hardness of the samples, such as by crushing or squeezing in-well collected samples, to the surface through fiber optics, well line vibrational signaling, or the like. In other cases, the analysis of samples at the surface of the well can still provide an inexpensive alternative and/or complement to gamma ray mapping which is currently performed and a faster analysis than x-ray diffraction methods currently performed and can still be used as a means of mapping a material (formation, region), and directing drilling/fracking operations. Data collected from such operations can be digitized or otherwise relayed as data through a computer system and then used to automatically direct or provide information to human operators through, for example, a graphical user interface, which can aid in the direction of well site operations. In some aspects, the method is performed with a well that has increased mud flow as the compared with current rates of mud flow so as to provide improved real-time analysis through cuttings, which may be particularly useful when the real-time cuttings analysis is performed with cuttings delivered to the surface.

The data collected in the analysis can be any suitable kind of data, but, as described herein, will favorably often include analysis of acetic acid, formic acid, and/or oil saturated water associated with the sample. The analysis also or alternatively can include measuring the amount of methane, carbon dioxide, and/or carbon monoxide that is released from the samples or released from a volatile compound trap.

Given the variable nature of materials to be analyzed the scale of the data that is analyzed in methods that are related to volatile compounds analysis can vary. This can be true even for a particularly kind of data as the conditions in which the sample are collected can vary. For example, with respect to cuttings the age of the cutting, condition of the cutting and its storage, and the nature of the materials contained in the cutting can influence the scale. Thus, in one aspect the method can comprise evaluating the material either through routine experimentation or by guidance provided through standards or similar means, such as machine calibration that is programmed based on the variables (e.g., known oil wells of a similar nature can be mapped and used as a calibration for similar wells), to assess the right scale of measurement for plotting or otherwise analyzing the data, as exemplified in the Examples provided below. The method typically then comprises seeking indication of the presence or absence of one or more of the compounds of interest. Where multiple samples from multiple locations are taken typically a map or plot will be generated, again as exemplified in the Examples. In such a case the method will typically comprise manually or automatically seeking patterns in the data at the selected scale(s) that will indicate changes or anomalies or "hits". In some cases, the change in the amount of a target substance in a scale will be from a "0" or near 0 level, or lack of detection, to the detection of any value above 0. As another example, for example, where oil as a percent of total rock value is used as a measurement, in some contexts (e.g., rocks with a porosity of about 8%) a measurement of at least 2% would be considered "high" oil value, and low values could be set at 0.1% or lower. By plotting the data clear patterns can be seen. Often times, a measurement of about 15% of the scale or more (e.g., about 25%, about 30%, about 40%, about 50% or more), would be considered a "hit". The analytical aspect of a volatiles facet of the invention also can comprise analysis of two or more types of data, such as permeability at one depth and non-permeability at another, e.g., to identify trapped zones of oil that can be very beneficial. Also or alternatively, various measurements, such as oil saturated water can be combined with other measurements such as formic acid, acetic acid and the like, such that one can measure the petroleum pay zone and formations around the pay zone that are in fluid communication with the pay as evidenced by formic acid, acetic acid, and oil saturated water. The combination of permeability and other information, especially when combined with other data from conventional means, can provide maps that identify one or more pay zones in a material/region. Use of data including other hydrocarbons can further explain the nature of the oil, such as whether there is heavier or lighter oil present (or otherwise whether the oil and/or gas deposits are of a similar or different nature and/or whether gas can be relied on to aid in the transport of oil to the surface, etc.), and relative petroleum deposit locations, whether there is a "seal" (low permeability region) around the oil deposit, and/or oil deposit locations in relationship to water and other pockets of oil and/or water in the material/region. Such data can aid in determining whether or not different pay zones can be obtained together or separately and under what conditions pay zones can be obtained. Thus, for example, analysis of such data can reveal whether or not an oil or gas deposit is compartmentalized with respect to other deposits of oil in the material/region.

As stated above, the various disclosures relating to the methods of the invention can be readily applied to devices and systems of the invention, which are also exemplified in the examples provided below. Thus, in another facet, the invention provides devices that comprise (a) a container or chamber for receiving and isolating samples of a material and (b) a detection component capable of detecting the amount of one or more target volatile substances released from the sample, wherein the substance comprises carbon monoxide, acetic acid, formic acid, or a combination thereof, optionally in combination with hydrocarbons, inorganic gasses, or a combination thereof. In still another facet, the invention provides a device comprising a crushable component or material that can contain samples, which when crushed provides information concerning the strength of the sample (and thus the material) and a system that comprises such a device and means for crushing the device (as well as optionally means for measuring the information, storing the information, relating the information, etc.). In still another facet, the invention provides devices and systems that are capable of both analyses.

With respect to devices that are capable of volatile substance analysis, a device of the invention typically comprises an energy input component that promotes the release of volatile substances from the sample. The energy input component typically is or comprises (a) a pressure generating device or system, (b) a device or system that promotes release of volatile substances through mechanical forces, thermal forces, or both, or a combination of (a) and (b). Often the device or system will comprise means (component, system, or the like) for isolating volatile substances released from the sample from the sample, the environment, and/or other components of the system or device, such as one or more operable valves. Devices and systems often will include a trap, which may be a non-selective or a selective trap, or comprise both kinds of traps. The trap can be, for example, a liquid nitrogen trap, which is capable of capturing volatile, condensable gasses, released from samples, such as cuttings. The dimensions of such devices are described elsewhere herein, as are suitable materials from which such devices can be made.

Devices for volatile compound analysis typically include means for measuring the volatile substances. This can include, e.g., a carbon monoxide detector or other kind of chemical detector and also or alternatively a less specific detection system, such as a mass spectrometer, examples of which are provided elsewhere herein. Where advantageous, the analytical parts of the system may be optionally isolatable from other parts of the system, such as to ensure proper operation and/or to avoid false signal events. The device/system of the invention may further comprise a programmable or data logic component for collecting data, relaying data, storing data, and the like, which may include alarms, automatic device means (such as means for controlling directionality of a drill), and/or a graphical user interface. The operation of the components of the device/system can similarly be automated and/or placed under control of a programmable unit or computer system.

In another aspect, the invention provides systems or devices for chemical analyses of volatile compounds in a sample of a material that comprises (a) a cryogenic trap that can be cooled and held at temperatures that are capable of capturing target volatile substances when such substances are in fluid communication with the trap (e.g., temperatures of about −100 degrees C. or colder, such about −110, about −120, about −130 degrees C. or less) (e.g., the device/system will typically include a cooling component or cooling means that is capable of selectively cooling the cryogenic trap, which can be in practice one, two, or more separate traps); (b) optionally, but typically, a component or system for selectively warming the cryogenic trap in a controllable manner, (c) one or more devices or systems for applying one or more forces to samples that the system is applied to, such as a vacuum system, preferably with the ability to apply multiple levels of vacuum pressure to the sample, and in preferred aspects the ability to apply relatively low/gentle vacuum on a sample, such as about 25-150 millibars of pressure (e.g., about 60-120 millibars of pressure) to a sample, (d) components for containing the volatile substances and keeping the substances isolated from the environment, such as a housing, (e) components for selectively isolating the trap from the sample, such that volatile compounds can be exposed to the trap only after cooling to a desired temperature, (f) an optional component for the capture of volatile substances that will not condense on the trap, which typically is selectively isolated from the other substances such that the noncondensable materials can be separately analyzed from the materials that condense on or otherwise bind to the trap and are thereafter released from the trap, and (g) a device for analyzing at least some of the volatile substances released from the trap, such as a mass spectrometry device, optionally with means/components for selectively allowing access of the volatile substances to the analytical device (e.g., one or more selectively openable valves), and (h) means or components for causing the transport of at least some of the volatile substances captured in the enclosed system. Such a system may also or alternatively further comprise (i) a component or means for evacuating any noncondensable gases out of the cryogenic trap as and if necessary without release of any condensable volatiles from the cryogenic trap if the analytical method requires high vacuum, such as a selectively operable pumping system. Systems that have means/components for analysis of non-condensable gasses/materials may further comprise means for capturing a set volume of such non-condensable materials, such as selectively operable vacuums that can act on such materials and/or components/means for selectively exposing such materials to the analytical part of the system and often means/components for transporting such materials to the analytical componentry of the system/device.

As described above, a cryogenic trap can be generated by contacting a suitable medium with a cryogenic substance such as liquid nitrogen, liquid argon, liquid oxygen, liquid air, liquid helium, dry ice, a dry ice slurry, normal ice, a normal ice slurry of water ice in fresh water, a normal ice slurry of water ice in a saline brine, or any other naturally cooling substance capable of achieving the minimum temperature required to freeze the substance(s) of interest onto the cryogenic trap. A cryogenic state may also or alternatively be achieved with mechanical refrigeration or cooling as may be achieved with a Kelvinator device. The Kelvinator or other cryogenic device must be able to achieve the minimum temperature required to freeze the substance(s) of interest onto the cryogenic trap.

A cryogenic trap component can have any suitable configuration. In one exemplary embodiment, the trap will be configured such that cooling of the cryogenic trapping device occurs on the exterior of a cryogenic chamber and volatile substances adhere to the interior of the cryogenic chamber. Alternatively, a trap can be provided wherein cooling of the cryogenic device occurs on the interior of the cryogenic chamber and volatile substances adhere to the exterior of the cryogenic chamber.

In one aspect, the cryogenic trap comprises one or more materials that are suitable for cyrogenic trapping, which typically are selected from materials that comprise one or more suitable metals, such as aluminum, copper, gold, silver, platinum, palladium, stainless steel, brass, bronze, nickel, cobalt, or any other appropriate metal, including alloys and/or any suitable combinations of such materials. A trap also or alternatively can be composed of a non-metallic material, optionally a non-metallic material that forms a substrate for trapping of volatile substances, such as, for example, carbon fibers, peek, natural or industrial diamonds or diamond films, glass, ceramics, or any other appropriate non-metallic substance or combination of such substances, alone or in further combination with one or more metallic substances. The trap can have any appropriate shape or configuration, including, for example, a shape selected from cylindrical, a u-tube, polygonal, sphereical, funnel shaped, ribbed, helical, and/or botryoidal shape, or any other appropriate shape.

A system or device comprising a cryogenic component or system according to such aspects of the invention can be configured to analyze any type of volatile compounds or volatile compound-associated sample(s). While the description herein places significant focus on extracting volatile substances from geologic materials, especially from materials from oil and gas wells, and particularly from cuttings from oil and gas wells, the methods of the invention can be performed, as stated already herein, with other types of samples and in another facet of the invention may even be practiced with volatile fluids that are independent of any kind of solid sample. For example, in one aspect one or more volatile analysis methods of the invention, such as those described above, is also or alternatively applied to a liquid, such as one or more drilling muds. In another aspect, such a method or set of methods is also or alternatively applied to a gaseous substance (e.g., a substance that is substantially, predominately, or entirely in a gaseous state under normal atmospheric conditions). In such aspects of the invention the inventive method can comprise filling a container or a component of the system with the gas to be analyzed and allowing the gas to make contact with a trap, such as a liquid nitrogen trap, and then subjecting trap-released gasses to analysis, such as by mass spectrometry. Where the gas is provided in a container, such as a vial, the method can include the step of filling the vial, optionally sealing the vial, and optionally forming a fluid flow in a sealed manner between the vial and the system such that volatile substances in the gas are not lost either due to escape or reaction. Alternatively, gas can be captured in a device, such as a syringe, and introduced into a system, e.g., a system under vacuum, by passage of a needle through a septum, and thereby emptying some, most, all, or essentially all of the components of the syringe into an inlet into the system and eventually, immediately, or near immediately thereafter into an inlet to a trap and thereafter an analytical device (or where a trap is not used, directly to an analytical device according to such aspects of the invention). Yet another alternative facet of the invention provides a method in which a gas containing amounts of volatiles, such as very low/trace amounts of volatiles in the gas, is to permit condensation of the gaseous volatiles on a trap, such as a liquid nitrogen trap, over a relatively longer period of time, to allow accumulation of even trace amounts of volatiles on the trap. Such a process could be used to detect extremely small amounts of explosive associated volatiles in air, or of trace amounts of hydrocarbons and/or organic acids in air associated with petroleum seeps or other relevant trace chemicals such as environmental contaminants. As such, such an instrument, and even many of the other devices and systems described herein, may be useful deployed as a mobile unit in a car, truck, plane, boat, or even a rocket. A system with multiple liquid nitrogen traps would provide continuous monitoring as while one trap was extracting a sample to analyze, another trap would be analyzing the previously trapped sample.

Systems and devices of the invention will typically comprise a device or a means for introducing volatiles from a sample into the system in an isolated manner. In one advantageous aspect, as exemplified elsewhere herein, the system includes componentry and/or means for introducing volatile substances to the device/system by way of syringe or needle injection, which often advantageously comprises a portion that punctures, pierces, or otherwise traverses a septum, which typically will be associated with a sample container in which the samples can be contained, preferably in a sealed state, such that loss of volatile substances is minimized (e.g., the system can comprise one or more samples that are hermetically sealed to a cryogenic trap inlet). The system will typically comprise componentry/means for generating flow of gasses to the cryogenic trap, such as pumps and the like. The system may further optionally comprise sources of gas, such as air or other gasses, which can aid the flow of volatile substances in the system/deice.

An analytical device for the assessment of volatile compounds according to such aspects of the invention typically comprises a mass spectrometer, but also or alternatively can comprise one or more additional analytical devices including, for example, a gas chromatograph; an infrared spectrometer; a Raman spectrometer; or any combination of these including multiples of the same type device (e.g., multiple mass spectrometers); or any other appropriate analytical means and/or combination of analytical means. As described elsewhere the device/system will often include programmable logic means/components that can put the operation of the device under automatic control and capture, record, and/or transmit and/or display data obtained from the performance of the method in digital form, print form, or in other known forms.

The combination of the above-described components into devices and systems provides several useful and novel additional or alternative aspects of the invention. Thus, for example, the invention provides a novel and useful device that comprises (a) a cryogenic trap device/component that is in fluid communication, typically selective fluid communication, with one or more mass spectrometers, usually in a configuration such that permits the release of material from the cryogenic device/component to the mass spectrometer component. Such a device can comprise means/components for flow of material through the system and means/components for selectively heating the cryogenic trap.

In another aspect the invention provides devices and systems comprising (a) a non-selective trap that can capture volatile substances in sample of materials, (b) a housing or other enclosure that prevents loss of volatile substances in materials in the system (at least to significant amounts, such as by maintaining at least 90%, at least 95%, at least 98%, or even 99% o more of the volatile substances associated with the sample once the sample is placed in a secure manner in communication with the system), (c) an analytical device that can detect one or more primary and/or secondary compounds that are associated with target materials, such as oil and/or natural gas, (d) components or means for transporting volatile substances to the trap and (e) components or means for selectively releasing materials from the trap in a manner that allows for determination of the presence or absence of at least one, preferably at least two, and typically 3, 4, 5, or more (e.g., at least 6, at least 7, at least 8, or even 10 or more) substances from the system. Typically such a system will further comprise one or more forces that can be applied to the system for promotion of the release of volatile substances, such as different pressures, which may reveal additional information elements concerning the substances such as permeability of the sample and/or will comprise means/components for causing chemical reactions of the volatile substances, for example by producing water in the system from one or more trapped substances. The systems can also include means/components for selectively crushing/squeezing the samples and providing a related measurement thereto such that compressibility and the related ductility/hardness of the sample can also or alternatively be provided. The sample containers provided by the invention are also novel and useful devices in and of themselves. Thus, for example, the invention provides a sample container comprising a selectively puncturable section, a housing that is capable of containing sample materials, such as oil-well associated cuttings, and that also is at least substantially impervious to the release of volatile substances, and optionally a crushable selection or component that allows for the application of crushing/squeezing forces on the container, in a known manner, resulting in a measurable amount of compression of the container that provides relative information about the hardness/ductility of materials in the container and also optionally promotes the release of volatile substances. Optionally and often such a container is configured to be in sealed fluid communication with one of the devices of the invention.

EXEMPLARY EMBODIMENTS & APPLICATIONS OF THE INVENTION

The following examples further illustrate various aspects of the invention but should not be construed as in any way as limiting the scope of the claims or the rest of the disclosure provided herein.

Example 1

This example provides a description of an exemplary device/system according to certain aspects of the invention and that also is suitable for application of several of the inventive methods described herein. An overview of the exemplary device is provided in the following figure (FIG. 1).

With respect to the device/system shown above, #1 depicts a first sample container, as described elsewhere herein. The first sample container #1 contains the sample of the material, such as cuttings taken from an oil well. The sample container #1 in the case of the depicted system is sealed and made of an impermeable material. The top portion of any sample container used in the system, such as the first sample container #1, is penetrable by the needle #2, which provides a passageway and means for transferring gasses released from the sample into the rest of the system, either immediately after penetration and/or after generation through the application of one or more forces acting upon the sample.

A second sample container #2 and a third sample container #3 are also shown, reflecting the fact that systems of the invention often are run with numerous samples in a given run or load (e.g., at least 5, at least 10, at least 15, at least 20, at least 25, at least 30, at least 35, at least 50, or more samples). In the case of the depicted system, a sample carousel, #4 is provided, into which the several samples to be analyzed in the particular run are loaded. Other types of automation other than a carousel could also be used, such as a cartridge holding a plurality of samples in either a vertical or horizontal profile (not shown), or in any angle between vertical and horizontal, that can deliver samples in any position appropriate for volatiles analyses (also not shown). The samples loaded in a particular load or run typically are related to one another, such as samples taken from a particular well site and maintained under particular conditions, but this is not necessarily always the case. In some embodiments of the invention, the carousel #4 is automated to run once the analysis on a particular sample is complete, often this will be controlled by a programmable computer which is connected to the system and in control over various functions operating in the system (and thus components of the system). Thus, for example, when analysis has been completely performed on the first sample container #1, the carousel can automatically rotate placing the second sample container #3 into position, whereby a penetrable portion of that sample container, can be penetrated, such as by the needle #8. The loading and transferring need not be in the form of a circular carousel, but could be, for example, in the form of a conveyor, or any other suitable sorting mechanism. The penetration of sample containers by the needle can, also, be under automatic operation or, more typically, is subject to operation by robot or computer once certain conditions have been satisfied (and subject to manual override). The sample containers depicted here comprise sidewalls that are made of a sturdy but crushable/collapsible material, such as brass, of a relatively fixed thickness.

The depicted system also comprises a ram #5 which is made of a material that is suitably composed and configured such that it can deliver an impact on the crushable sidewall or other modifiable portion of the container. For example, ram #5 may be made of a stronger metal, such as steel, which can repeatedly be used to crush the sidewall of the container and thereby delivering a crushing force to any sample materials contained therein, such as oil well cuttings. Ram #5 is typically connected to pistons #6, which can be air pistons or another suitable type of piston(s). Pistons #6 and ram #5 typically form a squeezing or crushing apparatus or system together, as depicted. The pistons #6 can be used to drive the ram #5 into the crushable portion of the sample container, e.g., #1, either upon a user command, under some automatic condition, and/or when directed by a computerized control system. The ram is typically driven by the piston or other driver mechanism (e.g., a powerful spring) into the container with a force that is suitable for crushing a portion of the container and delivering enough force to crush the sample material, thereby either releasing volatile compounds or assisting in the release of such volatile compounds in combination with the application of other forces or energies, such as vacuum pressure. The system typically comprises an anvil, #7, which assists in the crushing of the container, #1, by providing a hard surface against which the container is pressed when the ram #5 is brought into contact with the container #1 by application of the pistons #6.

The needle #8 also is typically associated with a needle assembly, which comprises a connection block #9, which, as depicted, is connected to a leveling screw, #10, which can raise or lower the needle, so as to cause the needle #8 to puncture a seal or other puncturable portion of the container #1 when engaged (alternative devices or means for raising and/or lowering the needle also or alternatively could be used). Engagement can be performed manually, automatically, and/or by computerized program control. The connector block #9 comprises a channel portion that gas passing from the sample container #1 and through the needle #8 can flow. In the depicted embodiment, the channel portion of the connector block #9 is in communication with a selectably engagable (closable/openable) right-angle valve #11, which controls the flow of gasses from the sample container/needle/connector block into the other portions of the system. "In communication" in the context of the depicted device means that gas can flow between the chambers, elements, or devices being described as being "in communication." The first right-angle valve, #11, as with other components, can be opened or closed manually, automatically, and/or under control of a computer, attached to the system, so as to practice the methods of the invention. In some cases, for example, the valve is closed to allow for controlled release of gasses from the sample container #1 into the rest of the system. The control afforded by inclusion of this first right-angle valve, and other valve controls in the depicted system, can, for example, permit different "runs" of the system on a single sample, under different conditions, such as under the application of different vacuum pressures on the sample. Other types of valves, such as ball valves, in-line valves, or any other type of valve that can satisfactorily operate in a vacuum system (not shown) could be used instead of right-angle valves as are exemplified here and described in any part of this disclosure.

Another two right-angle valves (#12 and #13) are connected to and in communication with the first right-angle valve, #11, and respectively control the flow of dry nitrogen into the system and the flow of gas from the sample in container #1 into the liquid nitrogen trap container. Other purge gases such as dry air, argon, oxygen, helium, and others also or alternatively can be used as the purge gas instead of dry nitrogen. Similarly, other cryogenic fluids such as liquid oxygen, liquid argon, liquid helium, and any other suitably cooling fluids also or alternatively could be used as the chilling means instead of liquid nitrogen exemplified here and described elsewhere herein.

The right-angle valve exterior is connected to a flexible vacuum hose, #14, which accommodates the up and down motion of the needle assembly raising and lowering into various sample containers (#1, #2, #3) on the carousel (#4). The vacuum hose #14 also is used to allow flow of gases to create vacuum pressure and to also allow sample gasses to pass further into the system. A pressure gauge #15 provides the operator with pressure conditions in the system, and thereby provides a check on whether the system is operating as expected, which is important to ensuring the validity of experiments and analyses performed in the system (other means/devices for measuring pressure also or alternatively could be used). A fourth right-angle valve #16 controls access to a diffusion pump #16a, (which typically are directly connected, as shown), which is used to expel gasses from the system (alternative means and devices for pumping also or alternatively could be included in such a system). A fifth right-angle valve, #17, provides a second inlet control on the liquid nitrogen trap container. As already mentioned all of these valves are controllable and control over the valves can be configured to operate in any suitable manner, so as to perform the various methods of the invention.

A relatively long first tube, #18, which is typically comprised of aluminum or a similar material, provides communication between the right-angle valve #17 and the liquid nitrogen cooling chamber, #20, which also acts as the exterior of the liquid nitrogen trap components of the system. Along the tube #18, one or more heater(s), #19a and #19b, can be placed, which allow for the application of heat, in a relatively predictable manner, to the system, which will aid with the release of gasses frozen to the liquid nitrogen trap. The heaters can be any suitable type of heaters, including units that radiate heat, that blow hot air, or that heat the tube by other suitable means. Typically, heaters (#19a and #19b) are placed at the ends of the first tube #18.

The liquid nitrogen cooling chamber #20 is the exterior of the liquid nitrogen trap freezing region. Here gas can come into contact with the liquid nitrogen cooled componentry of the system and freeze onto the trap. The flow of liquid nitrogen is controlled by a liquid nitrogen valve, #21. A thermocouple, #22, provides the user with the ability to monitor the temperature of the system, and optionally can be configured to send information to an associated computer system, which may control certain functions of the system. The liquid nitrogen trap has its own temperature controller, #23, which helps in controlling the application of liquid nitrogen. A sixth right-angle valve, #24, is positioned at the exit of the liquid nitrogen trap region and controls the flow of gasses from the trap into the remainder of the system. A specialized right-angle valve, the release valve, #26, is a pin hole bypass for analyzing gas that is released upon warming of the liquid nitrogen trap due to operation of heaters, #19a and #19b. As described generally above, liquid nitrogen is applied to this region of the system, lowering the temperature to a point at which volatile compounds contained in the sample can freeze to this trap region. The application of the heaters then permits the release of the frozen gasses from the region to the remainder of the system, including the mass spectrometer, #31.

A pin hole apparatus, #25, is configured to regulate flow of non-condensable (noncondensable) gasses from the noncondensable gas trap, #27, into the mass spectrometer, #31. The noncondensable gas trap, #27, is configured to collect gasses that will not bind to the liquid nitrogen trap. The noncondensable gas trap #27 comprises a right-angle valve, which allows for selective opening of this part of the apparatus, such that the gasses released from the warming of the liquid nitrogen trap are kept separate from the noncondensable gasses.

Diffusion pumps, #29 and #33, which may be backed by roughing pumps, provide flow and pressure control in the system, and are controlled by respective valves, #28 and #32. Often, any other type or types of suitable high vacuum pump(s), such as turbomolecular or cryogenic pumps or any other types of high vacuum pumps can be used instead of where diffusion pumps are cited in any part of this application. Control via manual operation or the computer system provides different amounts of pressure (positive or negative) in all or parts of the system, through the operation of these pumps. As discussed above, in operation several runs of the system can be performed on even a single sample by "pulling" on the sample through the application of different vacuum pressure conditions, thereby releasing different amounts of different gasses, thereby forming different aliquots from a single sample.

Access to the mass spectrometer, #31, is controlled by a mass spectrometer valve, #30. Any suitable mass spectrometer can be used in the system, and many are discussed above. The mass spectrometer #31 is configured to send information to a computerized system (not shown), typically via a data output connector (shown as wires connected to mass spectrometer #31), indicating the presence of target compounds of interest, such as hydrocarbons, inorganic gasses, carbonic acid, acetic acid, or another organic acid, or the anticipated breakdown products thereof, such as water or carbon monoxide.

Example 2

This example demonstrates the use of methods of the invention to determine oil and water saturation in a formation based on analysis of cuttings taken from an oil well, as well as permeability analysis obtained by analyzing a series of cuttings taken from the well.

Thirty samples of non-sealed cuttings taken from different depths in an oil well that had been stored in unsealed containers for a period of approximately three months under warehouse conditions in the summer (about 100-130 degrees F. estimated maximum daily temperature) were subjected to analysis using a device as described in Example 1 to provide information concerning the permeability of samples taken from different depths in the oil well, based on the release of target substances. The cuttings were subject to two runs of the system, forming two aliquots, based on the application of pressure conditions of 50 millibars and 5 millibars, respectively.

Figure 2:
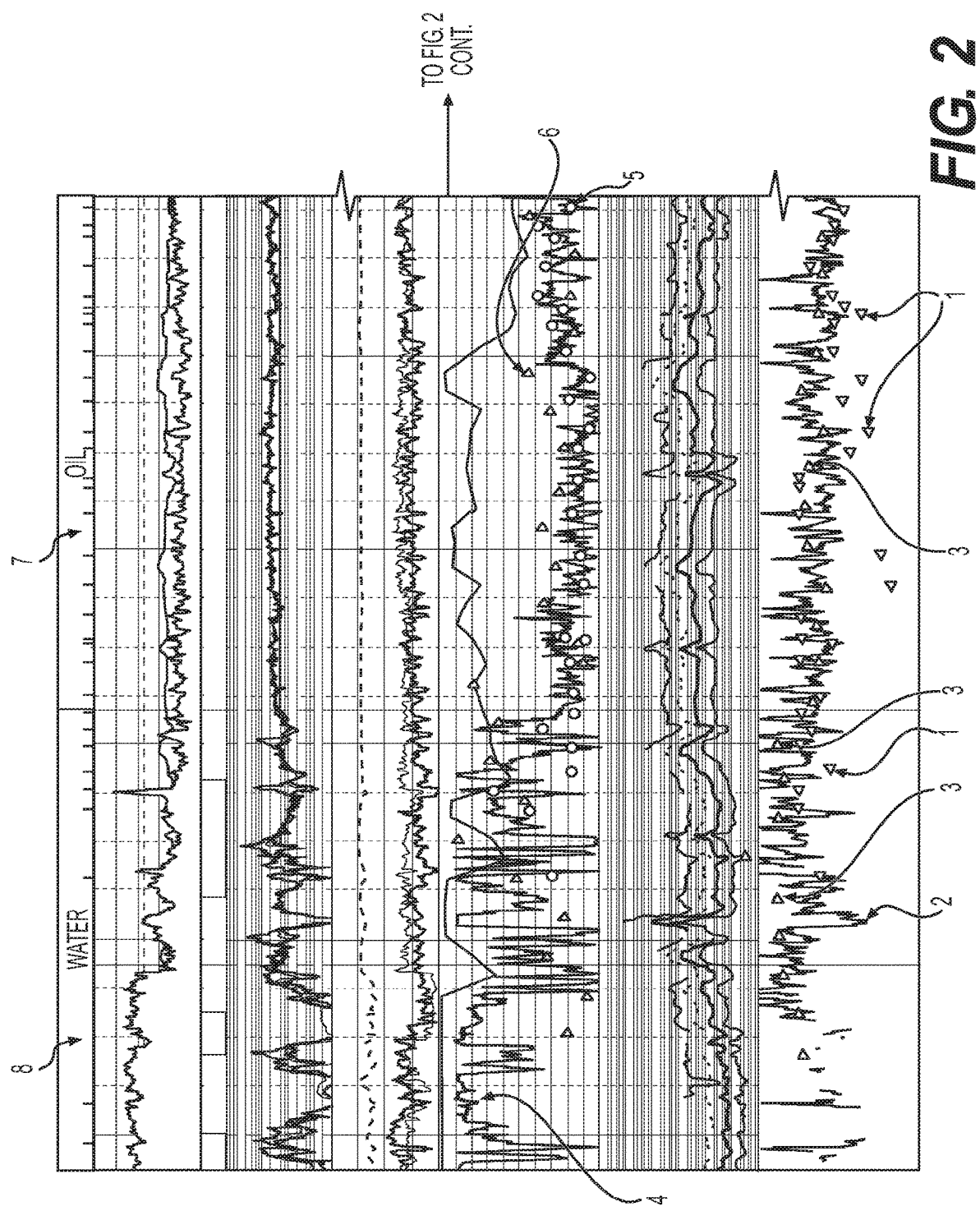
FIG. 2 is an example of a data set obtained by performing methods of the invention in connection with petroleum well-associated cuttings.
Figure 2:
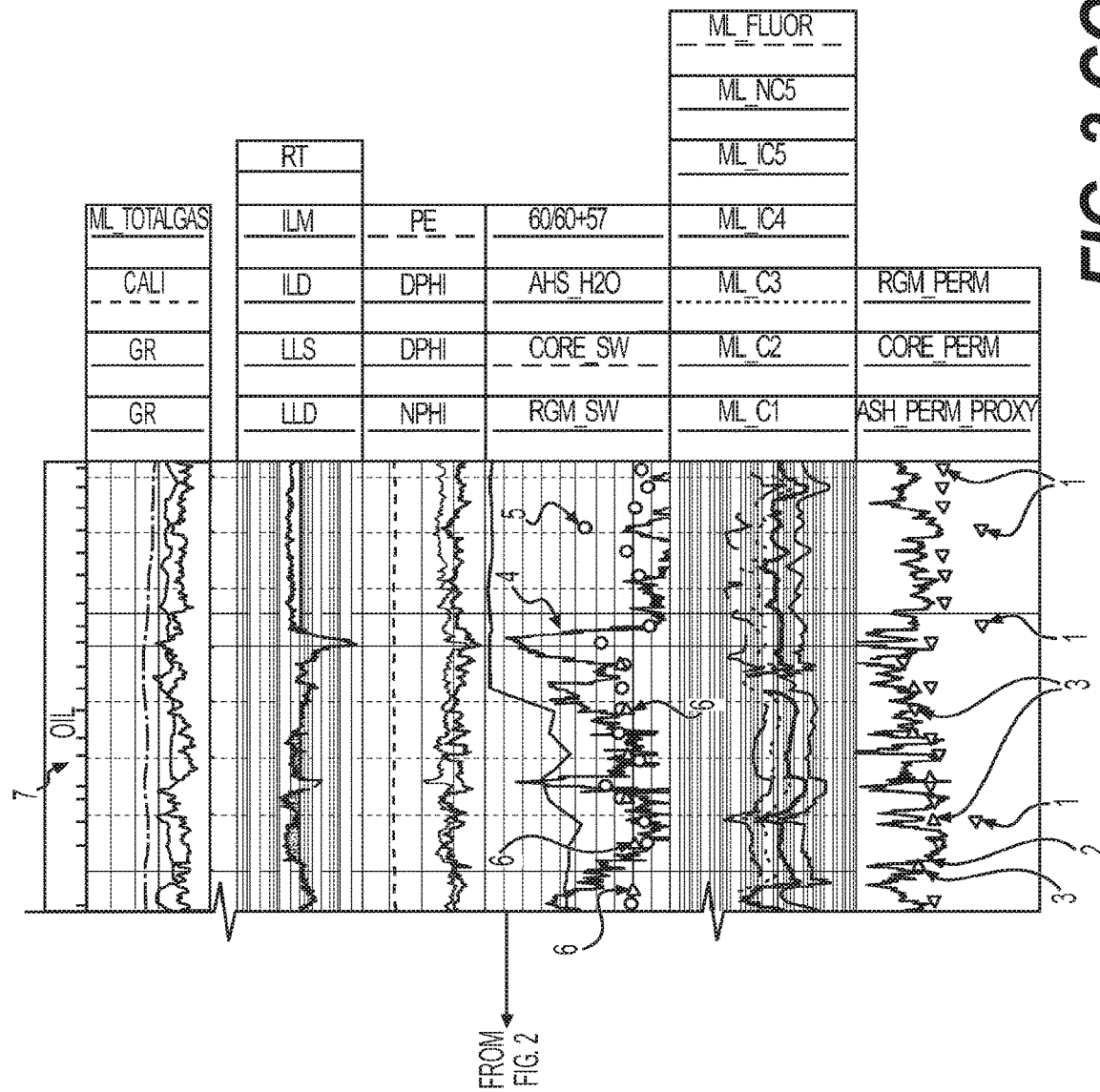

The right-hand column of FIG. 2, shown below, depicts an actual plot of the relative permeability of these samples, provided by two conventional permeability methods (e.g., the downward pointing triangles #1 are conventional sidewall oil core permeability measurements; curve #2 represents permeability assessments made through conventional well logging methods) and by application of the inventive method (upward pointing triangles, #3), as applied to cuttings from an oil well site. This data represents one of the first times that permeability information from a site was obtained from oil well cuttings, and the data shows that oil well cuttings can provide permeability information which correlates well with data obtained from significantly more expensive traditional methods. The permeability data was plotted either in millidarcies or in relative proportion to other permeability measurements using conventional techniques.

Other information included in FIG. 2 is a plot of mud logging data (gas chromatography data), in the second column from the left, indicating the presence of C1-C5 hydrocarbons in muds obtained from the respective plotted depths of the well (y axis).

The middle column provides $S_W$ plots obtained from various methods (the continuous line, #4, represents data from conventional well logging and the dots, #5, represent data taken from sidewall coring methods). The triangles, #6, are data obtained by the inventive method being applied directly to cuttings from the well. The results demonstrate a strong correlation in terms of $S_W$, here being obtained directly from cuttings and also and from more conventional and often more expensive conventional methods. This is another breakthrough aspect of the invention, obtaining both permeability and $S_W$ data from cuttings in a single run and providing a comparative analysis of such data, for different depths of a well, against other conventional methods of assessing a well site.

Other information provided in FIG. 2 include the mud log resistivity curve, data from oil staining on cuttings, caliper data (measuring bore hole sizes, red dashed lines), and conventional gamma ray data (which provides information about the type of material at the site—such as shale versus sandstone, carbonate, etc.) (plots in the first column on the left). Correlation of this information was used to identify the zones, which are indicative of the presence of oil, as marked by the vertical bar on the very left, #7. The water leg below the oil pay zone is indicated by the lower vertical bar on the left, #8.

In this data, conventional resistivity data failed to convincingly identify the presence of oil that could be detected by the method of the invention. This may be due to the inability of resistivity data to differentiate between oil and gas, because both compounds are non-conductive. This is one potential advantage of methods of the invention exemplified by this example. The zone of the most abundant oil fluid inclusions was the water leg #8, not the oil pay zone #7. Thus, use of the previously described fluid inclusion methods on this well also failed to identify oil pay zones, which could be identified by the cutting methods of the invention, thereby also reflecting a benefit of the inventive method.

Example 3

This example demonstrates the identification of an oil pay zone, through application of the inventive method on oil well cuttings, which were taken from a section of an oil well that was not being prospected based on application of pre-existing analytical methods.

Five hundred and eighteen cuttings taken from an oil well site, sealed at the well, were used in this analysis. Three aliquots were obtained from each cutting, using pressure conditions similar to those described in Example 2, plus an aliquot following intense sample dehydration. Permeability measures were obtained by the difference between aliquots 2 and aliquot 1 for each cuttings sample, #1. The data from the analysis were plotted and the actual plot of this data is shown in FIG. 3.

Figure 3:
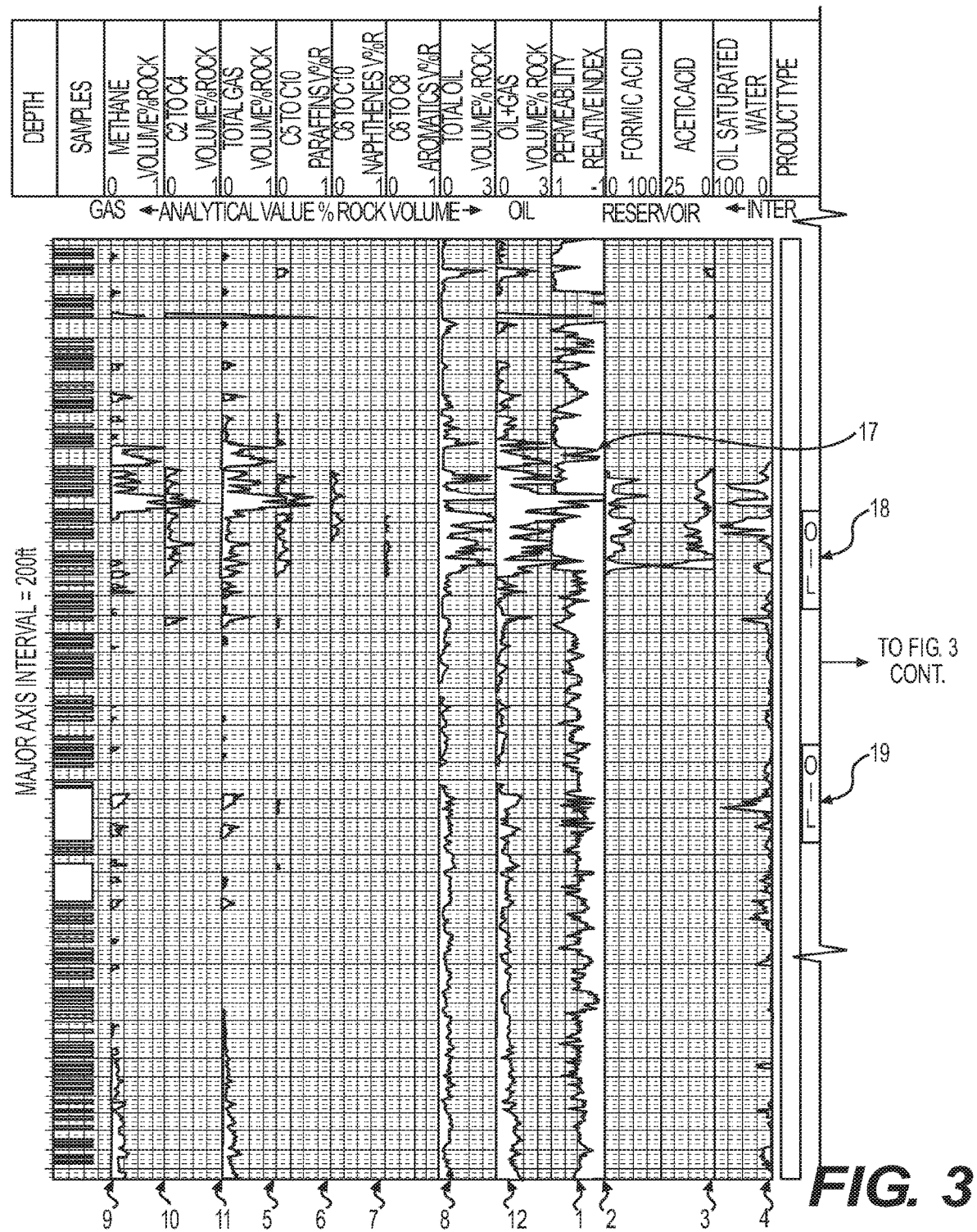
FIG. 3 provides another example of a data set obtained by performing methods of the invention in connection with petroleum well-associated cuttings.
Figure 3:
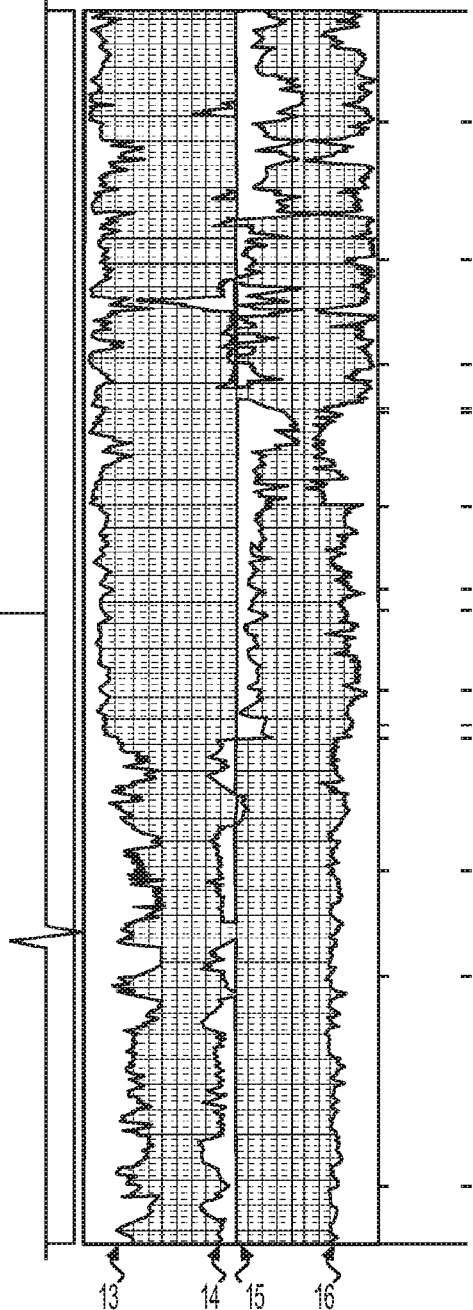

Numerous additional data points were also obtained and are reflected in FIG. 3, such as formic acid #2, acetic acid #3, oil saturated water #4, presence of C5-C10 paraffins #5, C6-C10 naphthenes #6, C6-C8 aromatics #7, and total oil #8. The gas components methane #9, ethane plus propane plus butanes #10, and Total Gas #11 are also plotted, as is the sum of the oil and the gas #12. Oil and gas-indicating measurements were obtained by the sum of the results of all three aliquots. The quality of the oil and gas product is indicated by the C8/(C5+C6+C7+C8) curve which helps differentiate heavier oil that plots to the right versus lighter oil and gas that plots to the left. The GOR (gas to oil ratio) curve #14 helps determine gas prone versus oil prone zones. The paraffins/(paraffins+naphthenes) curve #15, and the aromatics/(aromatics+naphthenes) curve #16 are used to evaluate the quality of the oil and discriminate various different oils from each other.

This data reflects the identification of a discrete oil pay zone. The low permeability region #17 on the graph reflects a tight zone overlying an accumulation. Below this tight zone (a zone of low permeability, generally less than about 10 millidarcies, and typically below about 1 millidarcy) (a tight zone that overlies pay keeping it from migration in the material can be considered a "seal") (these terms are also subject to general understanding in the art), two oil containing zones were identified through the assessment of the various basic data points. The upper zone #18 had been missed by previously applied, conventional methods, but was identified through analysis of oil well cuttings, using the methods of the invention, whereas an actual oil producing zone #19 was confirmed by the application of the various methods of the invention on oil well cuttings.

Figure 3B:
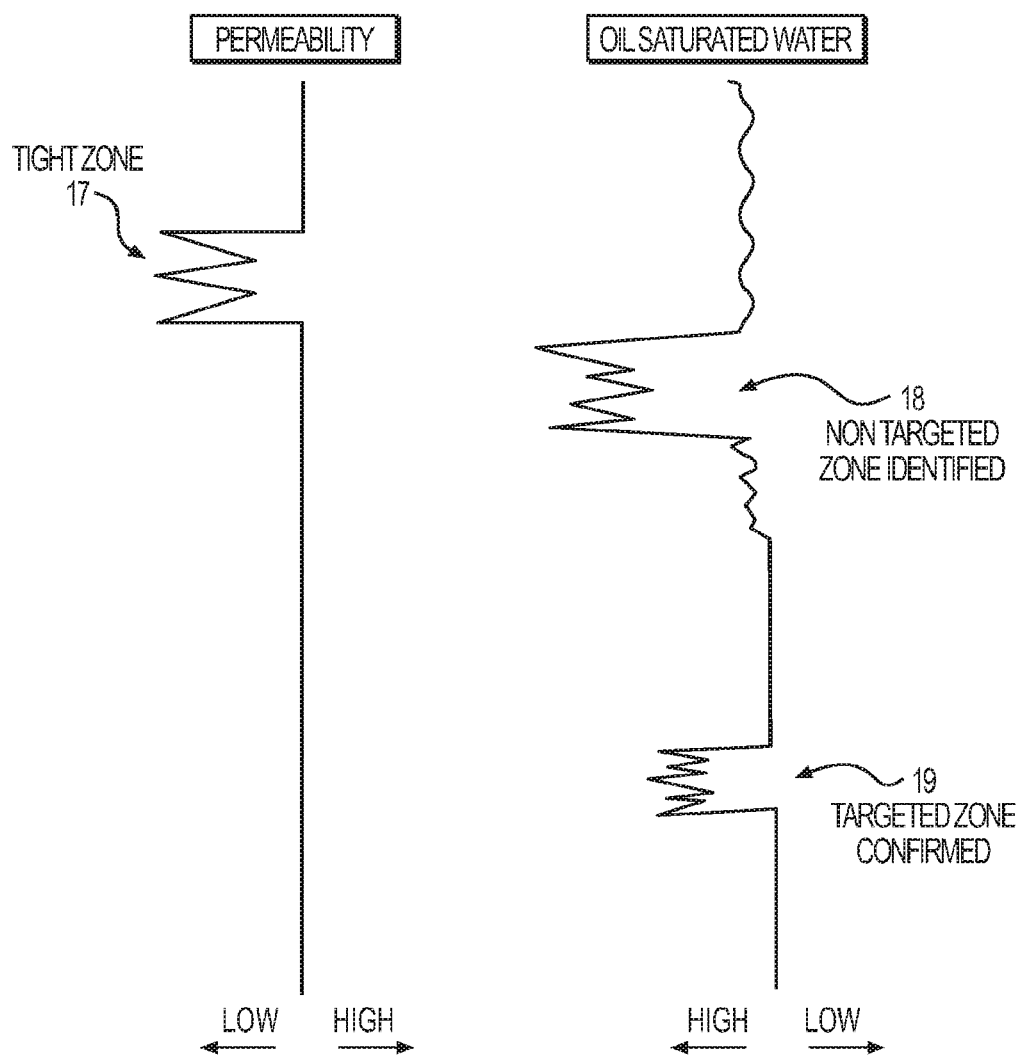
FIG. 3B provides a simplified, stylized view of select data shown in FIG. 3.

A simplistic interpretation of this data is reflected in FIG. 3b, which specifically reflects and focuses on key signals in the permeability and oil saturated water data that characterize the geologic formation (material) studied in this Example. Specifically, the permeability data reveals a tight zone, #17, with little permeability, above a non-target zone identified by oil saturate water according to the inventive method employed in this Example, #18, as well as the confirmation of a zone identified through other conventional methods, #19, through oil saturated water analysis.

The concept of "oil saturated water" has been developed as part of the invention described herein. "Oil saturated water" refers to water that has chemical indications of fluid communication with oil. Specifically, samples indicative of containing oil saturated water refers to those samples that show relatively high amounts of the indicator compounds formic acid, acetic acid, carbonic acid and/or bicarbonate, often from the presence of their breakdown indicator compounds, especially carbon monoxide and/or water, or from a combination of detection of such primary and secondary indicators. Any of these conditions can be combined, such as, for example, methods of the invention can include determining the amount of water, one or more other inorganic gasses (e.g., one or more of hydrogen, helium, nitrogen, argon, oxygen, hydrogen sulfide, carbonyl sulfide, carbon disulfide, and/or sulfur dioxide), carbon monoxide, carbon dioxide, carbonic acid, acetic acid, formic acid, methane or other C1-C5 hydrocarbons, and/or bicarbonate that is associated with/released from a sample as a means for determining if the same is associated with target substances, such as oil and/or natural gas. Conditions of analysis typically must be at least partially controlled in order for water to provide an indication of such material and, thus, communication with oil in a geologic formation. Thus, with respect to a device/system, such as that exemplified in FIG. 1, and described above, water is advantageously released from the liquid nitrogen trap at a temperature colder than the usually water sublimation temperatures in the device/system, usually about 55 degrees centigrade. Some of this water can then be detected at very low liquid nitrogen trap temperatures, such as about −140 degrees centigrade. Water with high amounts of the indicator compounds can be considered oil saturated water, whereas water without these indicator compounds is not oil saturated water. This characterization of water in a formation cannot be made with conventional methods, especially in zones with very high water saturation, where conventional well logs essentially provide no information as to whether or not that specific water is in communication with commercially viable oil and/or gas accumulations. The determination of the presence of the indicator compounds by the inventive analytical methods provided here allows this important distinction to be made. This tool can then be applied to wells that don't encounter commercially viable quantities of oil and/or gas, i.e., dry holes, to determine if such large commercially viable oil and gas occur close to the location of the dry hole, or not. These analyses could also be performed at the well site, and indicated zones of nearby oil and gas could be targeted with side track wells drilled from the initial pilot well at the fraction of the cost of drilling another well to explore for the nearby pay zone at a later date.

This Example shows that cuttings-derived data, such as permeability and oil saturated water, can be used to determine the presence of oil and to also determine permeability and discrete geologic zones containing oil, even ones missed by other, conventional methods.

Example 4

Figure 4A:
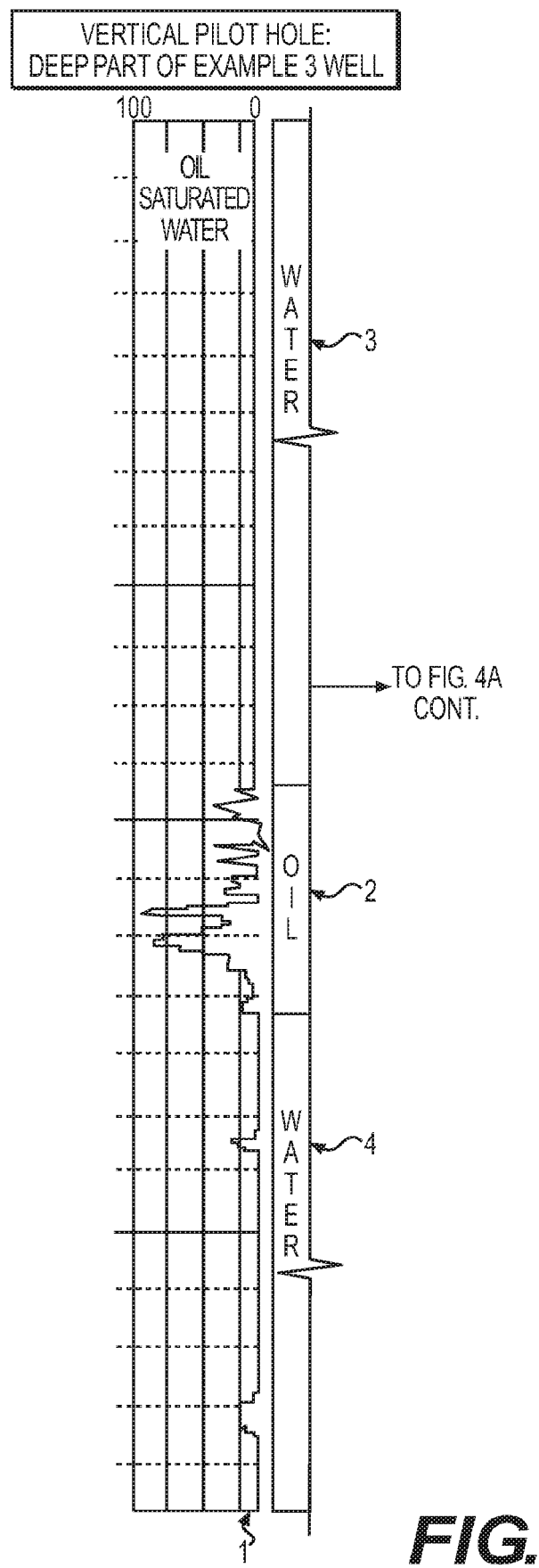
FIG. 4A is an illustrative plot of oil, water, and oil saturated water in connection with a vertically oriented petroleum well.
Figure 4A:
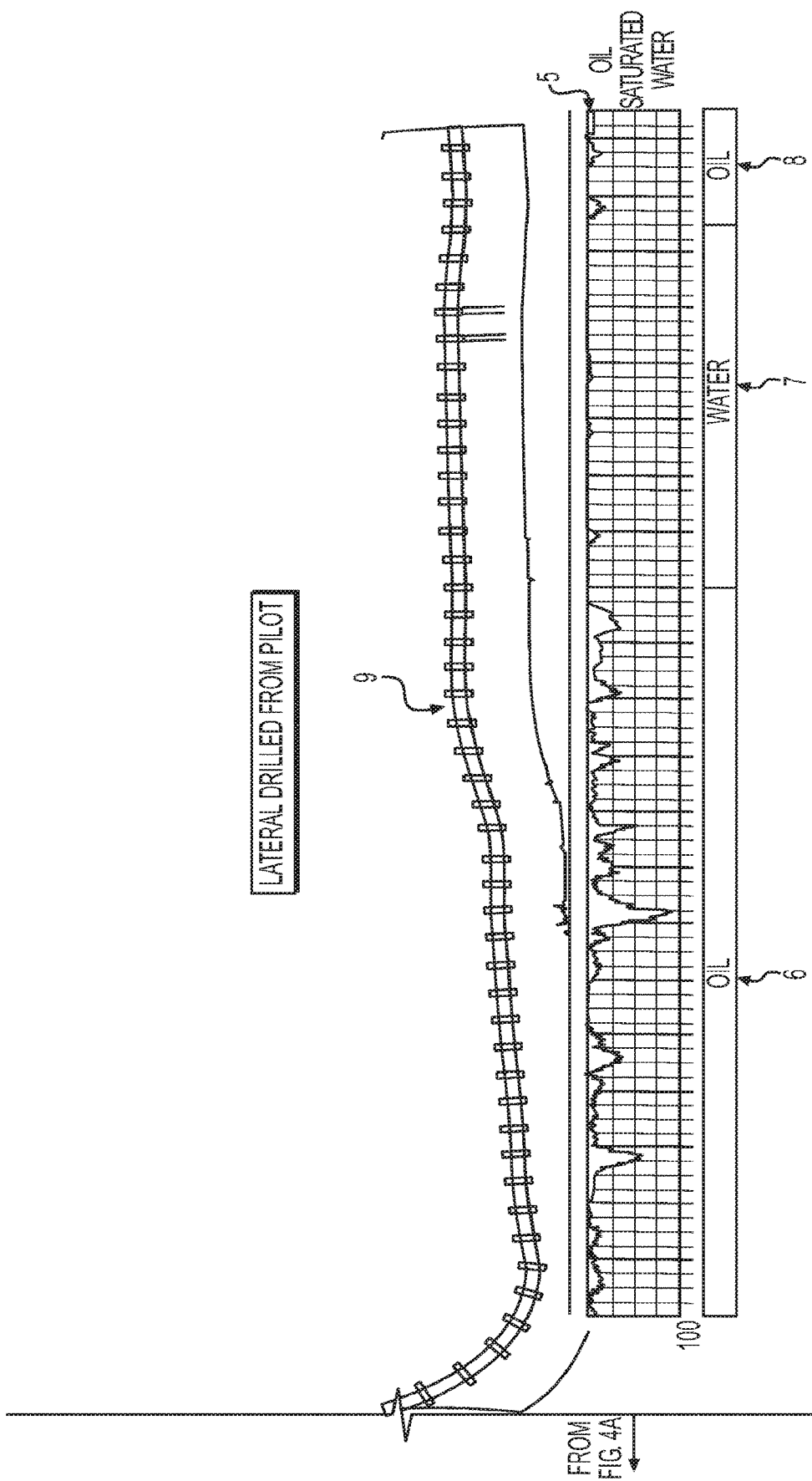

An analysis was performed as described in Examples 2 and 3 on 139 cuttings that were sealed at the well or the deeper section of the vertical pilot oil well described in Example 3, other samples were taken from a lateral line drilled as a sidetrack from the pilot well following the evaluation of the pilot hole to locate the deep pay zone. Three aliquots were analyzed for each sample under the pressure conditions described above in Example 3. The oil saturated water results are shown in FIG. 4a (labeled element #1).

The oil saturated water anomaly in the vertical pilot well reveals an oil rich pay zone #2, which then became the target for drilling and fracking the lateral sidetrack. High water saturations are indicated above #3 and below #4 the oil pay zone #2. To be able to use this information to aid in deciding at what depth to drill and land a lateral sidetrack to a pilot hole requires very quick analytical and interpretive turn-around time. Usually the interpretation needs to be delivered within 24 hours of the vertical pilot well reaching its total depth. Samples are often air expressed back to the lab, or hot shot by car if close enough, once or twice a day so the analyses can keep up with the drilling of the well as much as possible.

The oil saturated water data of the lateral sidetrack #5 shows the lateral was in the oil pay zone #2 penetrated by the vertical pilot well for about 2,700 feet, this is shown as #6. Following drilling in the oil pay zone #6 for about 2,700 feet the lateral sidetrack drilled through a zone of low water saturation for about 1,000 feet #7. At the end of the lateral sidetrack, the oil pay zone was re-entered for about 500 feet #8. The lateral's well track #9 shows that the deepest part of the lateral was at the beginning of the lateral. The lateral continued to drill shallower and stay in the oil pay zone #6 until the bore hole became sufficiently shallow that the lateral was no longer drilling in the oil pay zone #6, but that further drilling was above the oil pay zone and in the shallower water leg #7. Towards the end of drilling the lateral the well's track dips back down as shown towards the end of #9. Dipping back down results in the borehole re-entering the Oil Pay Zone as #8, as revealed by the oil saturated water curve #5.

Figure 4B:
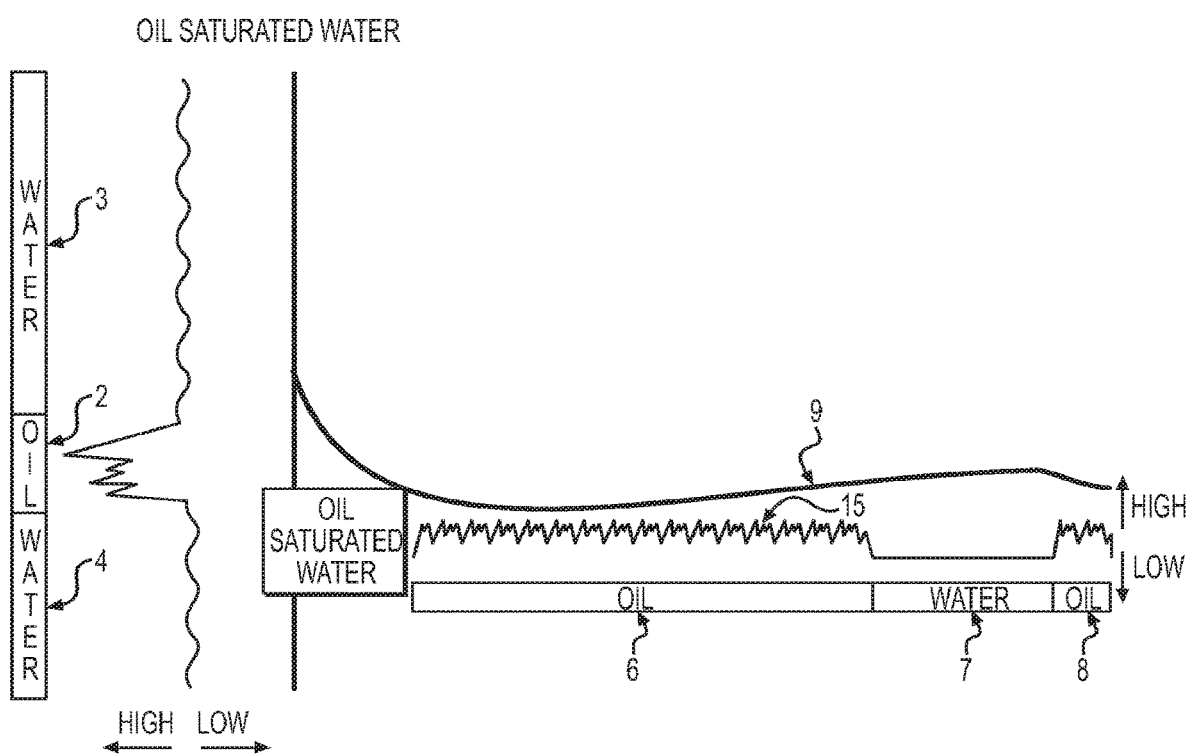
FIG. 4B is a simplified representation of key data provided in FIG. 4A.

A stylized/simplified representation of certain elements of this data is provided in FIG. 4b. Specifically, vertical zones of water #3, oil #2, and water #4 zones are plotted, with oil saturated water #15 along the well track #9 identifying lateral zones of oil #6, water #7, and oil, #8. This reflects the ability of methods of the present invention to be applied to wells that have both vertical and lateral characteristics, and to provide "maps" of data in both directions, even in a single well or area.

This Example demonstrates that the methods of the invention can allow for real-time data collection at the site of a lateral being drilled, such that this real-time data can be used to help "steer" (direct, guide) the direction of the lateral, so as to keep the borehole in or very close to the oil pay zone.

Example 5

This Example demonstrates application of a method of this invention to distinguish between oil pay zones and gas zones in a well site.

In this Example, 205 sealed oil well cutting samples were subjected to analysis as described above. Three aliquots were obtained from each sample, under the discrete pressures (25 millibars, 1 millibars, and 0.1 millibars)

SW was calculated from conventional petrophysical data, indicating the presence of hydrocarbons in the geologic formation at the site. However, SW cannot distinguish between water and gas deposits, as discussed above.

Figure 5:
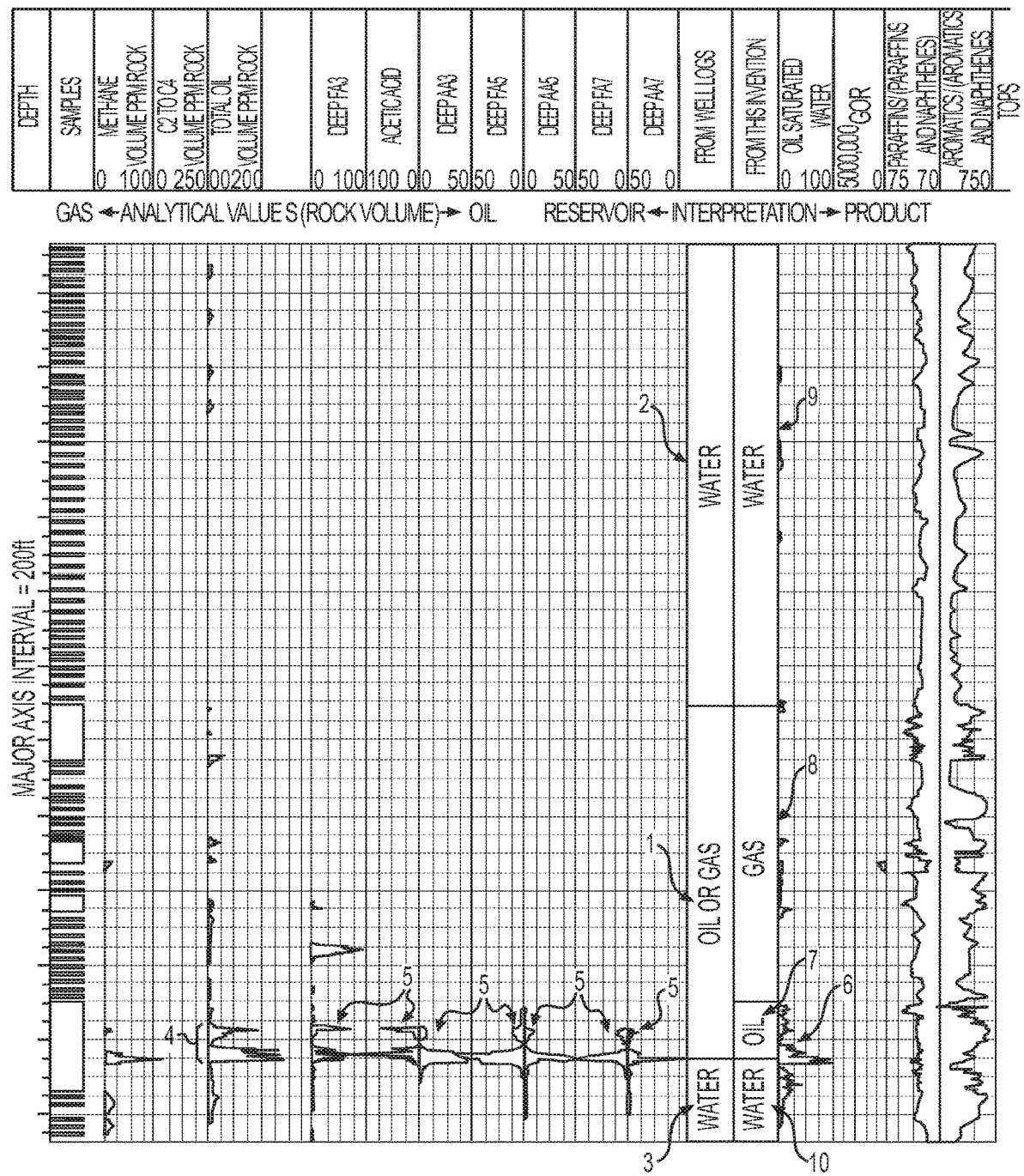
FIG. 5 provides yet another example of data obtained by performing methods of the invention on cuttings.

The results of the various data obtained by the performance of the method, such as acetic acid and formic acid information, are plotted in FIG. 5. A stylized interpretation of this data is shown in FIG. 5B using the same numbering scheme as in FIG. 5.

A post-drilling appraisal of the target indicated the well under analysis in this Example was a gas well and as such was not economic and was abandoned. Conventional well logs indicated a large pay zone #1 of several hundred feet in thickness overlain #2 and underlain #3 by strata having high water saturations. The well was perforated and tested at about the middle depth of the pay zone. The well flowed gas. At that time the operator abandoned the well thinking the pay zone was all gas.

Analyses using methods of the invention, however, indicates the bottom 200 feet of the pay zone to be oil #7. This determination was based on high total oil responses #4, high acetic and formic acid responses #5, and high oil saturated water #6. The remaining pay zone above the oil pay is then gas #8, as tested. Above the gas are strata with high water saturations #9, and below the oil pay are strata with high oil saturations #10.

Figure 5B:
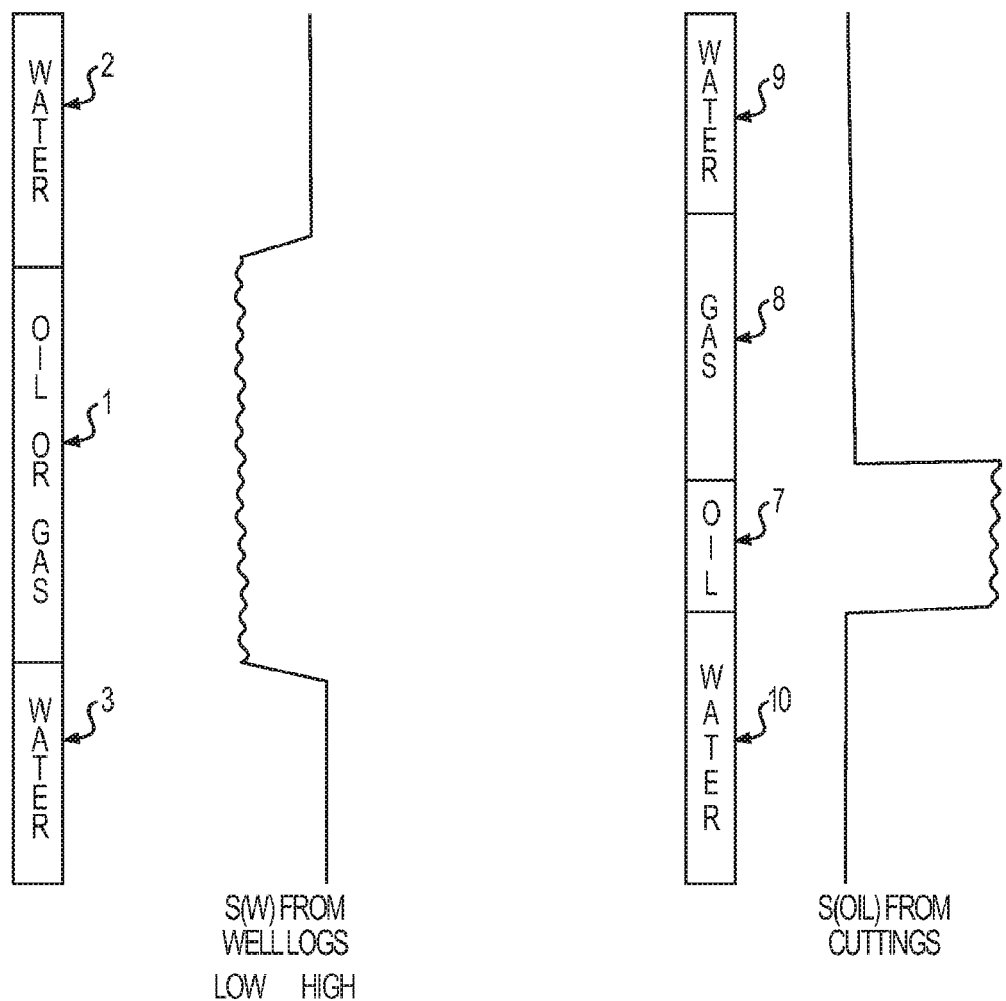
FIG. 5B provides a simplified representation of select data presented in FIG. 5.

The data shown in FIGS. 5 and 5B demonstrates that cutting-derived data obtained by applying methods of the invention can distinguish between oil and gas pay zones, which is of significant economic importance.

The data shown above demonstrates that cutting-derived data obtained by applying methods of the invention can distinguish between oil and gas deposits and also can confirm conventional core analysis information. As conventional core analysis is significantly more expensive and more time intensive than the cutting analysis of the invention this provides yet another important benefit of the inventive methods.

Example 6

The methods of the invention can be applied to large regional areas or wells that span large regional areas to provide plots of entire fields, regions, or cross-regional wells. The identification of acetic acid and/or formic acid and/or oil saturated water in cuttings can indicate that although that a subject well is a "dry hole" (a well not producing appreciable amounts of oil or gas), the well is nonetheless in proximity to a field. This data can then be used as a means for guiding exploration from the well site in terms of lateral drilling or the drilling of new, nearby wells. A simple, stylized version of a plot of data that would be obtained from performing such an analysis is shown as FIG. 6.

Figure 6:
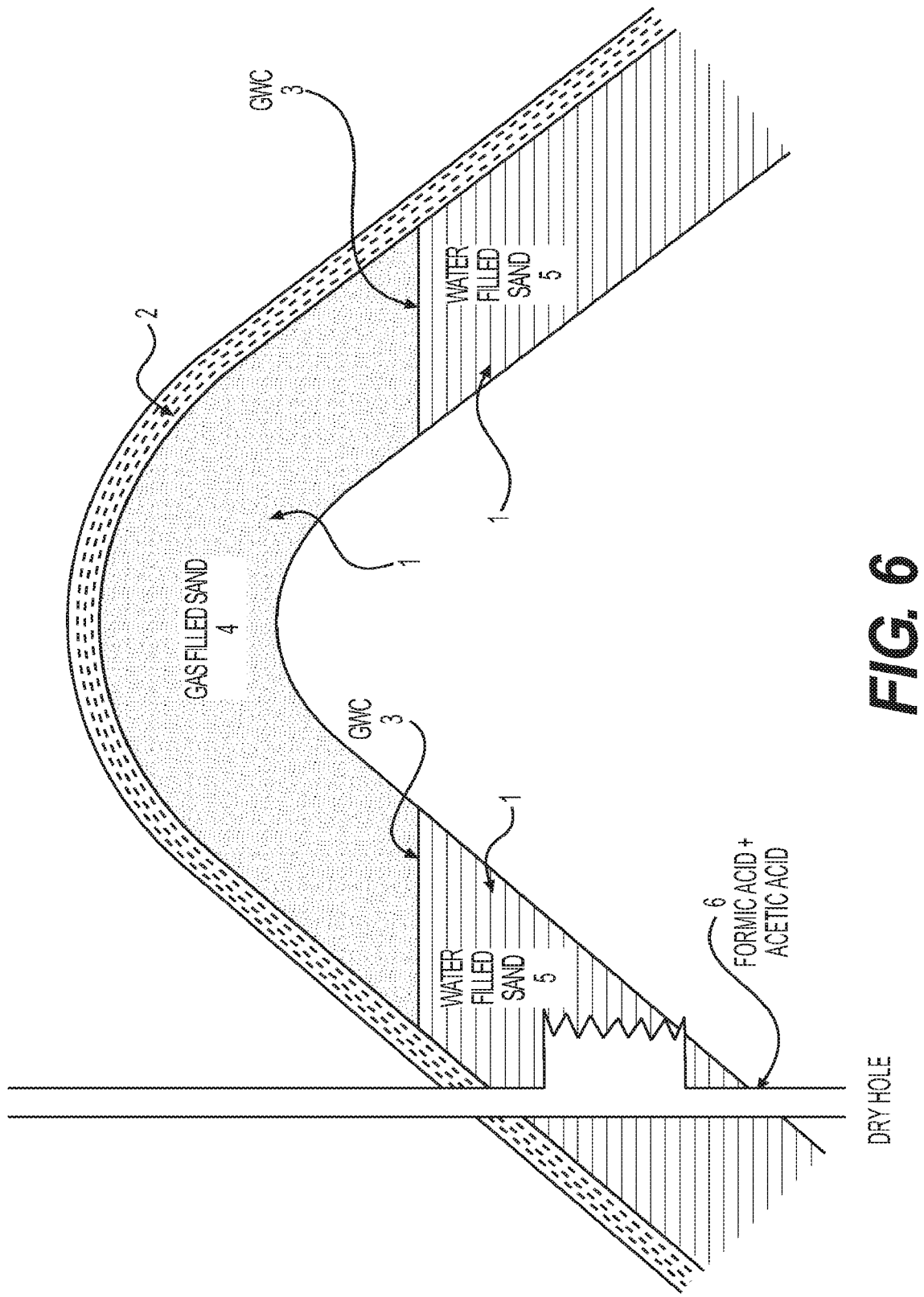
FIG. 6 is a representation of a type of petroleum-associated geologic formation that can be identified and characterized by use of methods of the invention.

More specifically, FIG. 6 provides a simplified 2-dimensional representation of a large conventional gas field. A permeable sandstone reservoir rock has undergone deformation so as to have a structure suitable for trapping oil #1. The sandstone reservoir #1 is overlain by a shale having low permeability #2 that acts as a seal. Gas has migrated into the sandstone reservoir #1 from a deeper source and now fills the sandstone down to the gas water contact (GWC) #3. The sandstone shallower than the GWC is charged with gas. The pores in the sandstone, which are deeper than the GWC, are filled with water. Formic and acetic acids occur in oils and wet gases, and can partition out of the gas and oil phase into the water phase. These light carboxylic acids are miscible in water. An aspect of the invention is the realization that measurement of high amounts of these acids in formation waters in water-filled permeable reservoir formations indicates close proximity to large economic pay zones in conventional oil and gas plays #6. In unconventional reservoirs with very limited permeability the oil and gas coexist in intimate contact with high amounts of formation water, and often in those cases the proximity to pay indicating acids occur in high amounts within the pay zone itself. This is the case in the previous Examples. However, in this conventional high permeability example, the gas and water are able to segregate into separate distinct zones as controlled by gravity separation.

Example 7

Figure 7:
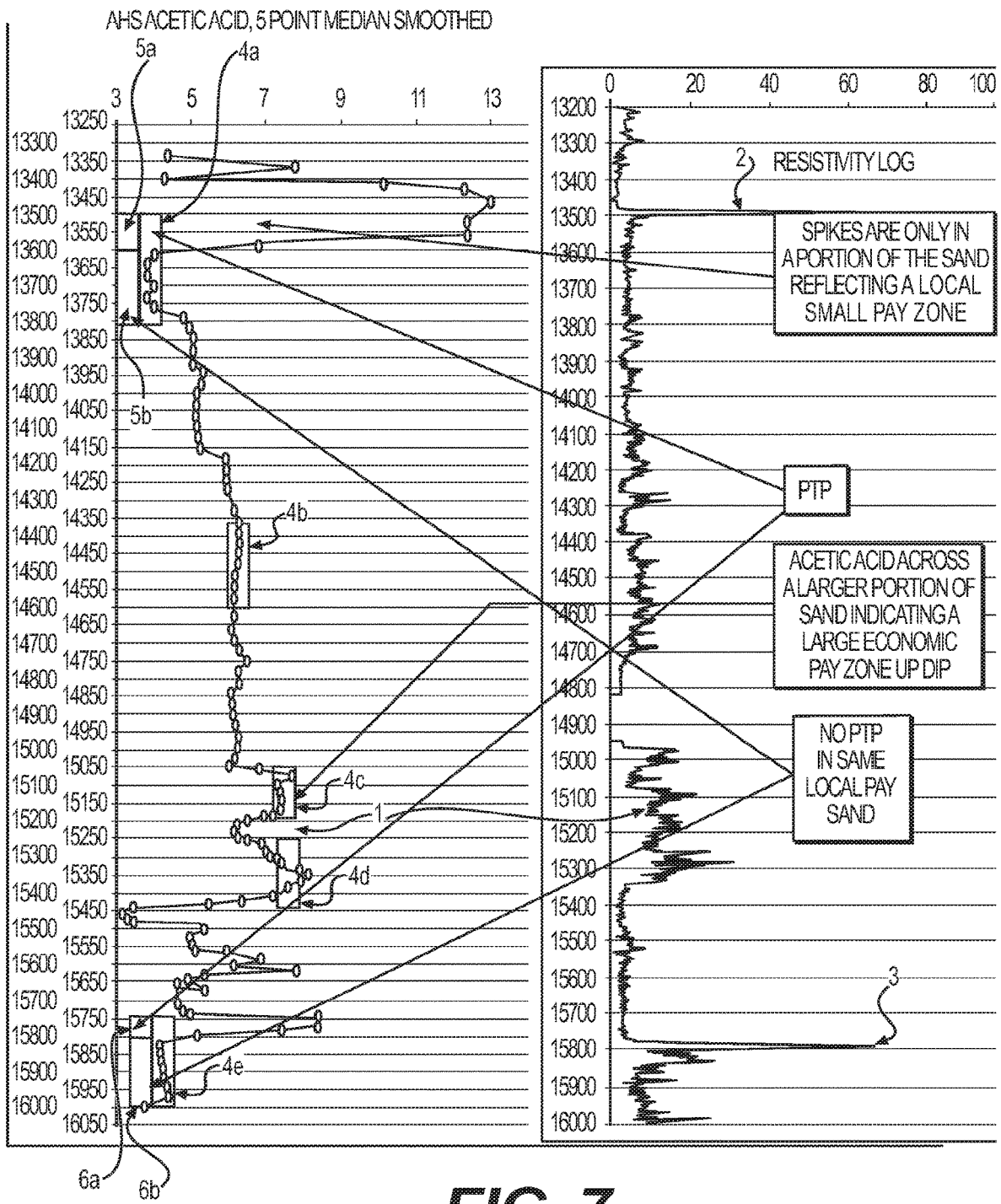
FIG. 7 provides a plot of acetic acid measurements in a geologic formation against resistivity log data to identify petroleum associated regions in sandstone formations/sands.

This Example provides the results of analysis performed with wet reservoir sands directly beneath two small local oil pay zones, as well as two wet sand that are down dip from a giant gas reservoir, as shown in FIG. 7. The resistivity log indicates two small uneconomic pay zones in this well, #2 and #3. Five rectangular boxes, #4a-#4e, are the sandstone bodies in this well as indicated by the gamma ray log. The rest of the penetrated strata depicted here are shales. Sands #4a and #4e have small oil legs at the top of the sands, and are water wet below the oil. Sands #4c and #4d are water wet, but are continuous with reservoir sands to a giant gas field up dip. Sand #4b is water wet and has no updip pay. The acetic acid information is plotted against a resistivity log. This data provides not only information about the presence of oil pay zones, but mapped against the nature of the material also reflects where in the site would provide the best economic payout.

It can be advantageous to relate the methods and results of this Example to the disclosures in Example 6 and FIG. 6, in that the material of this Example contains a thick water charged sandstone having row resistivity and being located about one half mile laterally and 500 feet in depth down dip to a large gas field #1 that produces from the same sandstone formation. There are no seals between the gas field and this dry hole. The sandstone, which is the source/cause of the dry hole, is in good permeable communication to the same sandstone formation in the giant gas accumulation, as shown in FIG. 6.

Although this sand in fully water charged and shows low resistivity at this location, the entire sandstone body shows high acetic acid contents, which, according to an aspect of the invention, is indicative of proximity to the giant nearby gas field #1 in FIG. 7. If this well was drilled prior to the nearby giant field being discovered, the conventional logs and other types of conventional analyses that might have previously ordinarily be applied to these samples, would have provided no indications that this well is in close proximity to the giant gas field. However, the high acetic acid anomalies #1 in these wet sands #4c and #4d, provide a unique indication of the existence of a large nearby petroleum accumulation. This data would strongly support further exploration in this area.

There is another sand in FIG. 7 that is water wet and contains no pay #4b. The acetic acid contents of sand 4b are similar to the surrounding shales above and below it. From other wells drilled in this area it was known that sand 4b is not charged with gas or oil updip to this location. The low acetic acid contents of sand #4b relative to the obviously higher acetic acid concentrations in zones #4c and #4d provides a local calibration that indicates the importance of the acetic acid in sands #4c and #4d with respect to analyzing the characteristics of the material/formation.

There are two more sands #4a and #4e that the resistivity log indicates have small pay zones at the top of each sand. In each of these sands with minor pay zones #4a and #4e, acetic acid anomalies #5a for sand #4a and #6a for sand #4e can be seen. A very interesting aspect of acetic acid anomalies #5a and #6a is that they also only occur near the top of each sand. The acetic acid anomaly for sand #4c and #4d is high for the entire sand body. This is the situation that was expected for a sand such as depicted in FIG. 6, wherein the entire sand body is charged with oil or gas updip. Diffusion and fluid flow in geologic formations is usually much easier along bedding than across bedding. Hence the fact that the entire sands #4c and #4d show high acetic acid contents is an indication that those sands are completely charged at some distance updip, and they are. On the other hand, the fact that sands #4a and #4e show acetic acid anomalies only at the top of the sands is an indication that this is a small oil deposit of only local extent and may be of lower or even insufficient economic interest with respect to drilling. The acetic acid is observed only directly adjacent to the small oil columns seen in the resistivity log as #5a and #6a. Most of each #4a and #4e sand lacks any acetic acid anomaly as shown by the lower portions of each sand as #5b and #6b.

This data reflects that an aspect of the invention is the use of acetic acid data derived from geologic formations to classify the analyzed sands. Sand #4b shows no increase in acetic acid relative to the shales immediately above and below, and therefore sand #4b was determined to be non-prospective, and data from surrounding wells support that interpretation. There are only very localized acetic acid anomalies at the top of sands #4a and #4e, and this data indicates these acetic acid anomalies #5a and #6a are local in nature and not indicative of nearby economically significant pay. On the other hand, the entirety of sand #4c and #4d show high acetic acid contents. Even though the magnitude of the anomaly in sand #4a is higher than that in sands #4c and #4d, the fact that the anomalies in #4c and #4d encompass the entire sand, whereas the anomalies in sands #4a and #4e encompass only the top of the sands is indicative that the #4c and #4d anomalies are related to/indicative of large and likely economically significant pay zones, in contrast to the implications derived from the more limited anomalies in sand #4a and #4e. Thus, this Example demonstrates how the inventive methods of the invention can be used to "map" or characterize an entire geologic structure or region with respect to proximity to petroleum pay zones in the structure/region.

Example 8

Figure 8A:
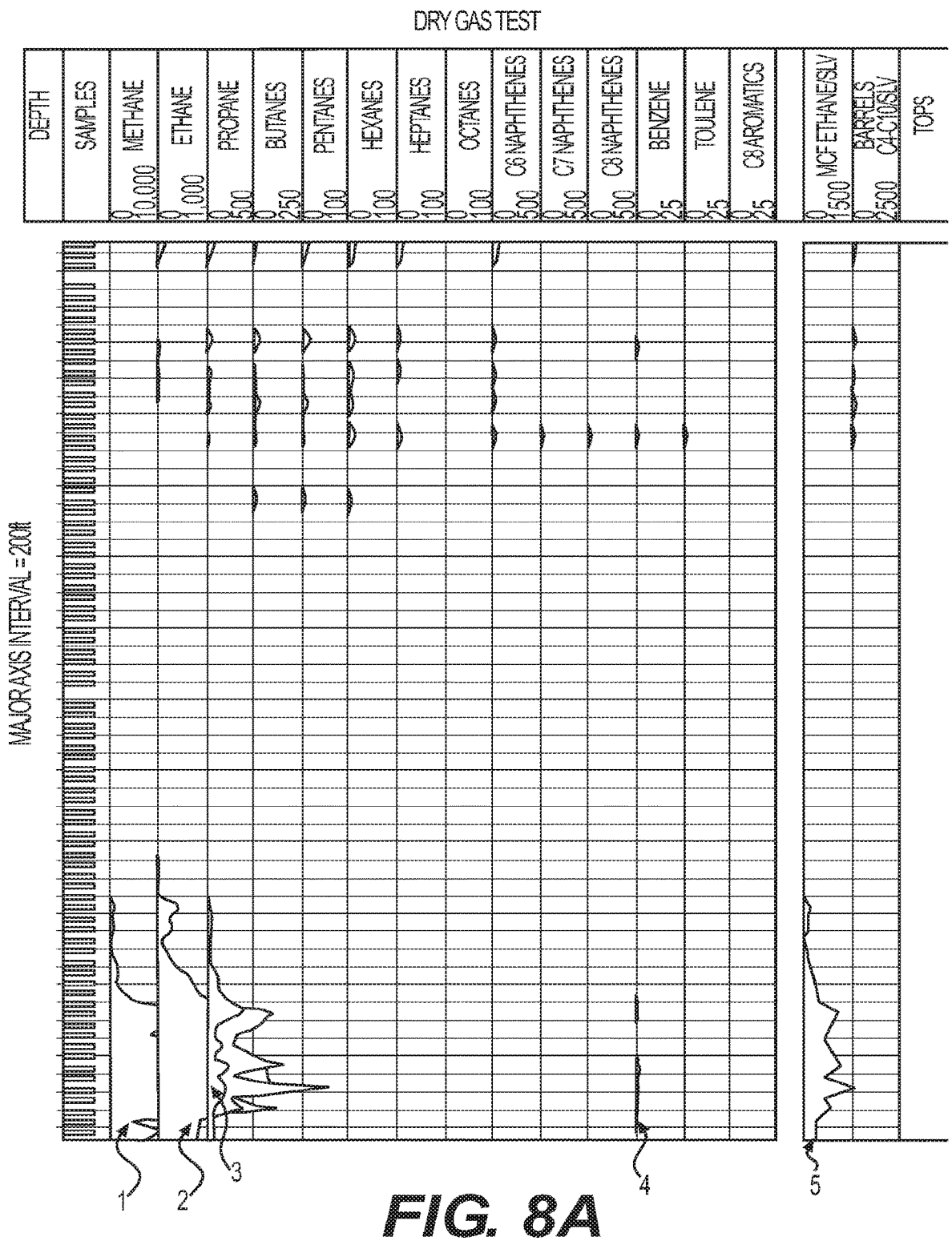
FIGS. 8A and 8B provide a plot of multiple hydrocarbons at different depths to analyze the nature of petroleum deposits in a geologic formation.
Figure 8B:
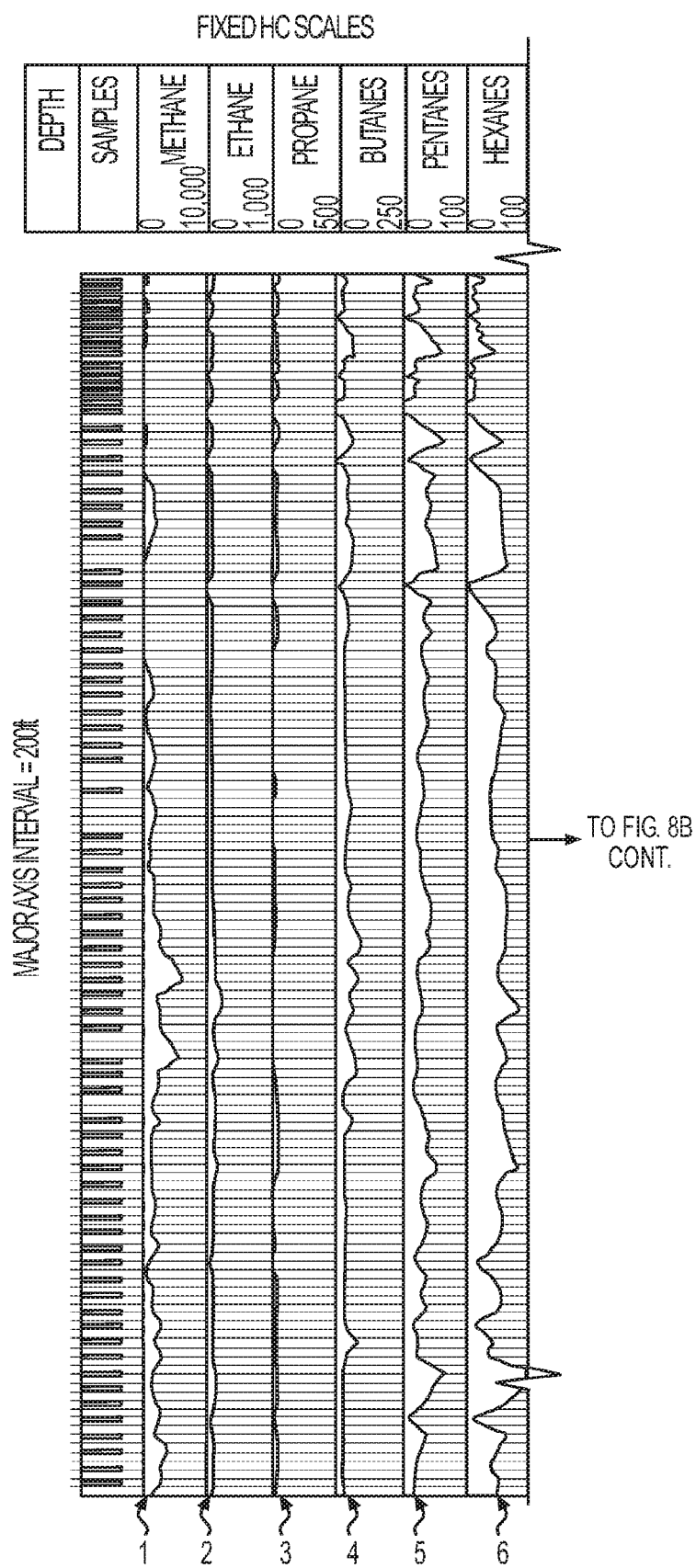
Figure 8B:
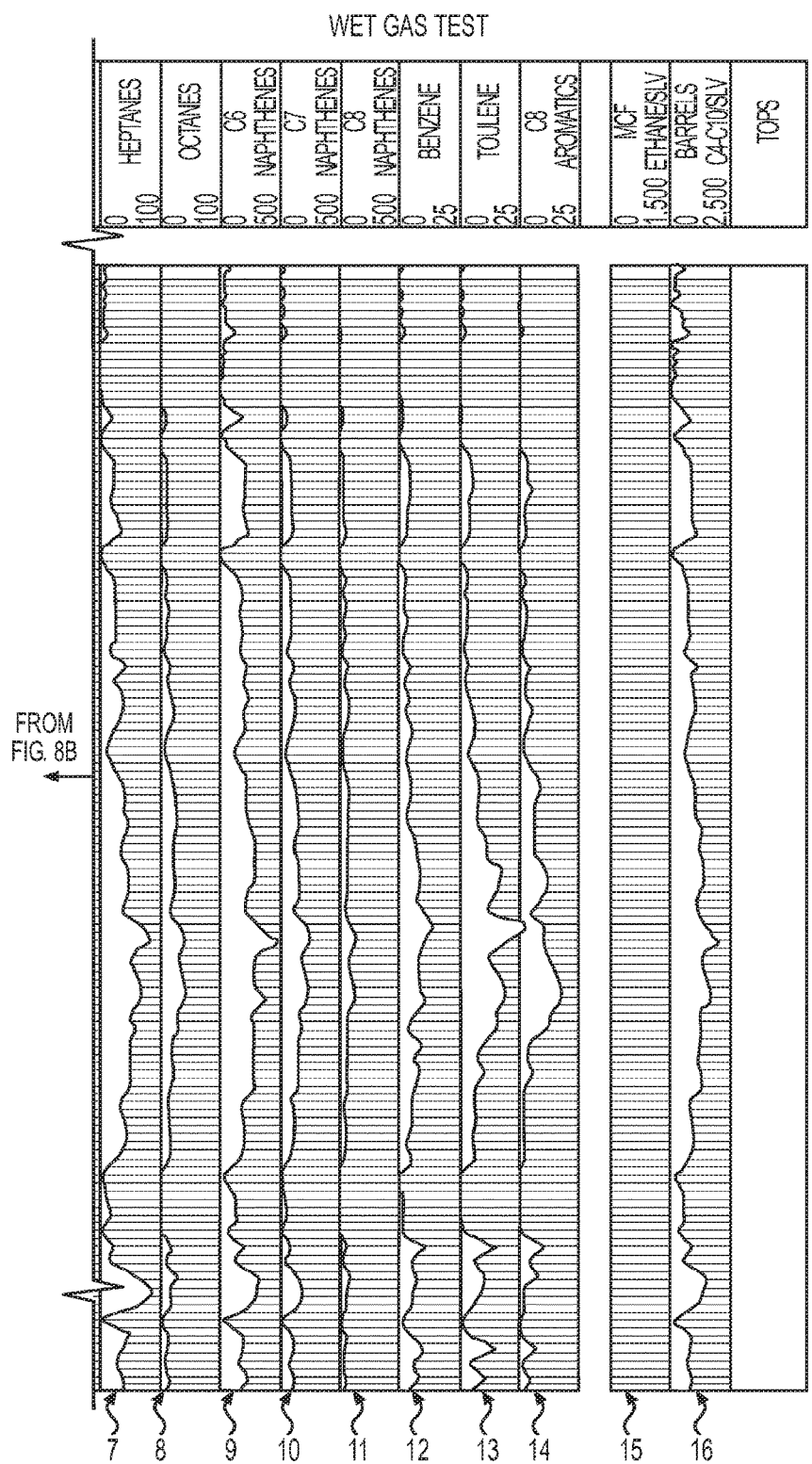
Figure 8C:
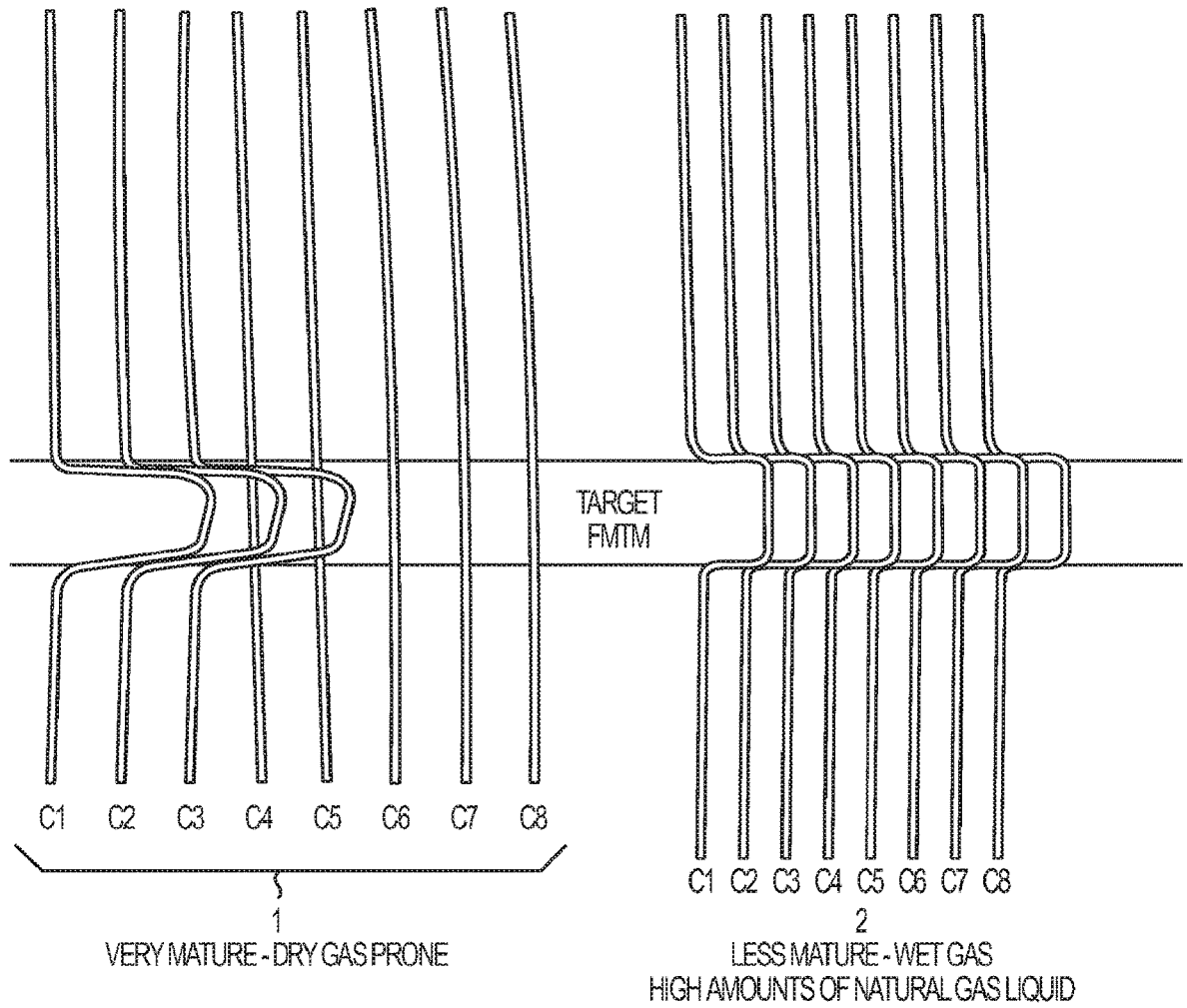
FIG. 8C provides a stylized representation of data associated with a particular type of geologic deposit that can be characterized by methods of the invention.

Plots were obtained from the performance of methods described above for a "dry gas" site and a "wet gas" site. The results of these analyses are shown in FIGS. 8A and 8B. A stylized interpretation of this data is shown in FIG. 8C. This analysis reflects the ability of methods of the invention to distinguish between the nature of various target sites.

In FIG. 8a, a dry gas anomaly deep in the well is dominated by methane #1, ethane #2, and propane #3. Higher liquid hydrocarbons are essentially absent, with the exception of a trace amount of benzene #4 that can be barely seen. The curve #5 shows the total amount of ethane that would be produced from a standard lateral drilled about 4,500 feet long with a production radius of about 50 feet. The analyst can calculate this number as the number of nanomoles of the gases to be analyzed can be determined as the results are quantitative and referenced to analytical standards, and the volume of sample analyzed is kept constant to 400 microliters of rock for each sample. The result shown as curve #5 is simply the result of upscaling the data to how much ethane by volume the analytical results are equivalent to for a cylindrical rock volume that is 4,500 ft long with a radius of 50 ft.

Figure #8B is plotted at the same scale as Figure #8A. As shown, there is much less methane #1, ethane #2, and propane #3 here. Also, the data reflects there is much more liquid hydrocarbon content than seen in the data of FIG. 8A. The C4-C8 paraffins are shown as #4-#8, the C6 to C8 naphthenes are shown as #9-#11, and the C6-C8 aromatics are shown as #12-#14. The track showing predicted ethane production #15 is insignificant compared to the same track #5 in FIG. 8A plotted at the same scale. However, the predicted liquids production is much higher in FIG. 8B than in FIG. 8A. FIGS. 8A and 8B both depict unconventional wells where the source rock is also the reservoir after hydraulic fracking. The source rock in the well shown in FIG. 8A has been buried to much greater depths and thus has generated much drier gas than the source rock in the well shown in FIG. 8B. The gas compositions derived from these analyses thus provide information about burial history of the target formations, which is a critical piece of information in petroleum exploration, both for conventional and unconventional reserves.

This situation is shown in the simplified diagrams on FIG. 8C. The drier gas shown as #1 is produced from the source rock that has experienced much higher temperatures for much longer periods of time then the wetter gas shown as #2.

This data can be used to address a great variety of geologic issues, especially when combined with other information from a variety of sources.

Analysis can be and often will be applied to relatively greater sized hydrocarbons, such as up to C10 hydrocarbons, but the C9 and C10 data obtained in this work were omitted from the FIGS. 8a and 8b for the sake of clarity. Since FIGS. 8A and 8B are plotted at the same scales, it is apparent that the gas from the FIG. 8A well is much drier than the gas from the FIG. 8B well. This Example reflects several aspects of the invention—from making standards to using such standards or more generally comparing data from several well sites to characterize a multi-well geographic/geological area.

Example 9

Figure 9:
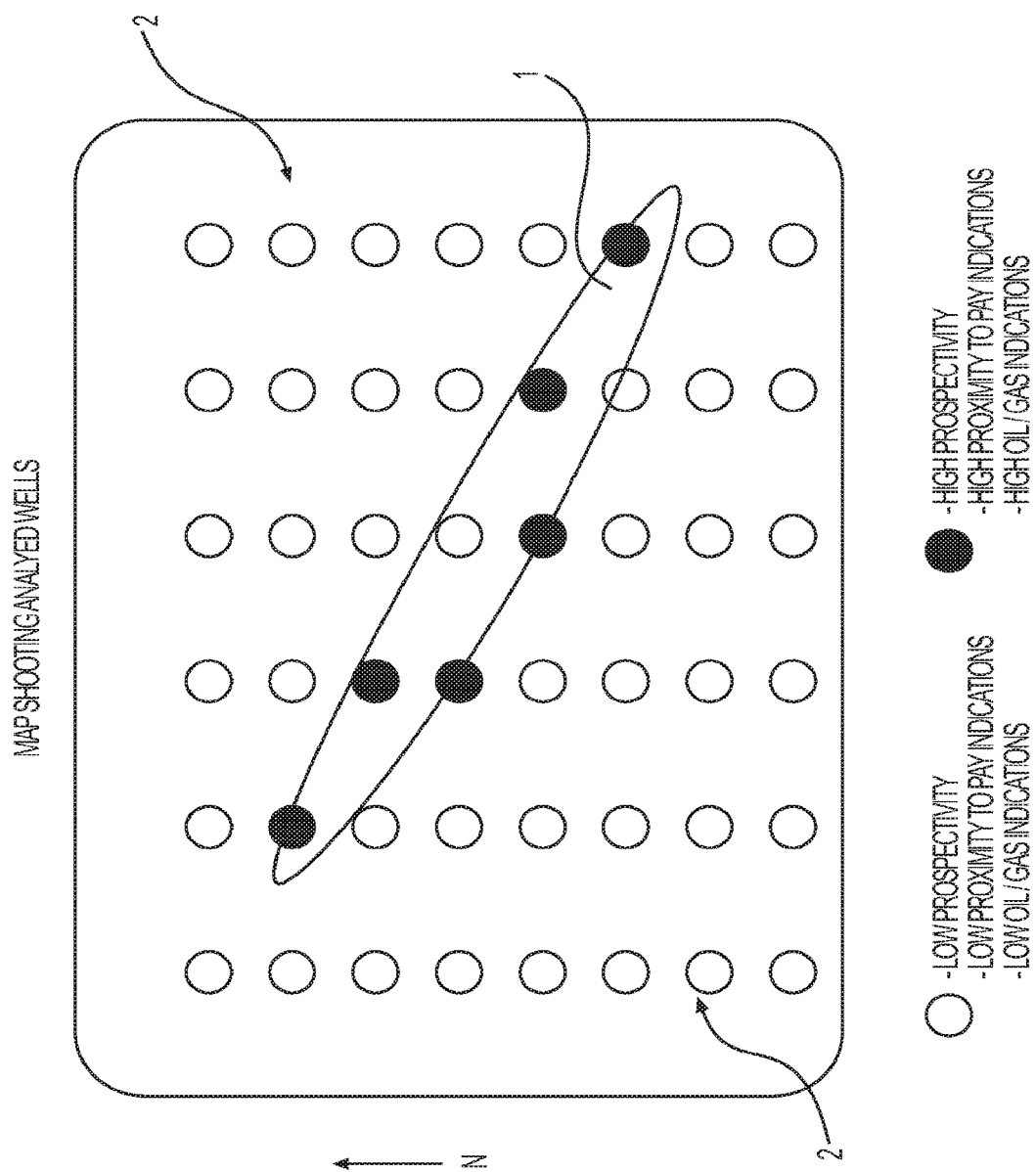
FIG. 9 is an illustrative representation of mapping a region of sites using the method of the invention to characterize a larger area comprising multiple drilling sites.

Methods of the invention could be applied to map out regions, as noted elsewhere herein. An illustration of the concept is shown as FIG. 9. FIG. 9 provides an example of what the output of such a regional mapping of oil well sites would conceptually look like, providing areas of high oil indications #1 and/or other information, such as porosity, which could be used to provide maps of favorable drilling sites and also used to predict other less prospective sites versus zones of low oil indications #2 or zones of low proximity to pay indications, or other indications from the data that can attest to high or low probability of finding oil and/or gas.

Example 10

In this Example, data was gathered in a manner similar to the protocols described in Examples 2-4. The data obtained from this analysis is shown as FIG. 10 and an interpretation of the data is provided as FIG. 10A.

Figure 10:
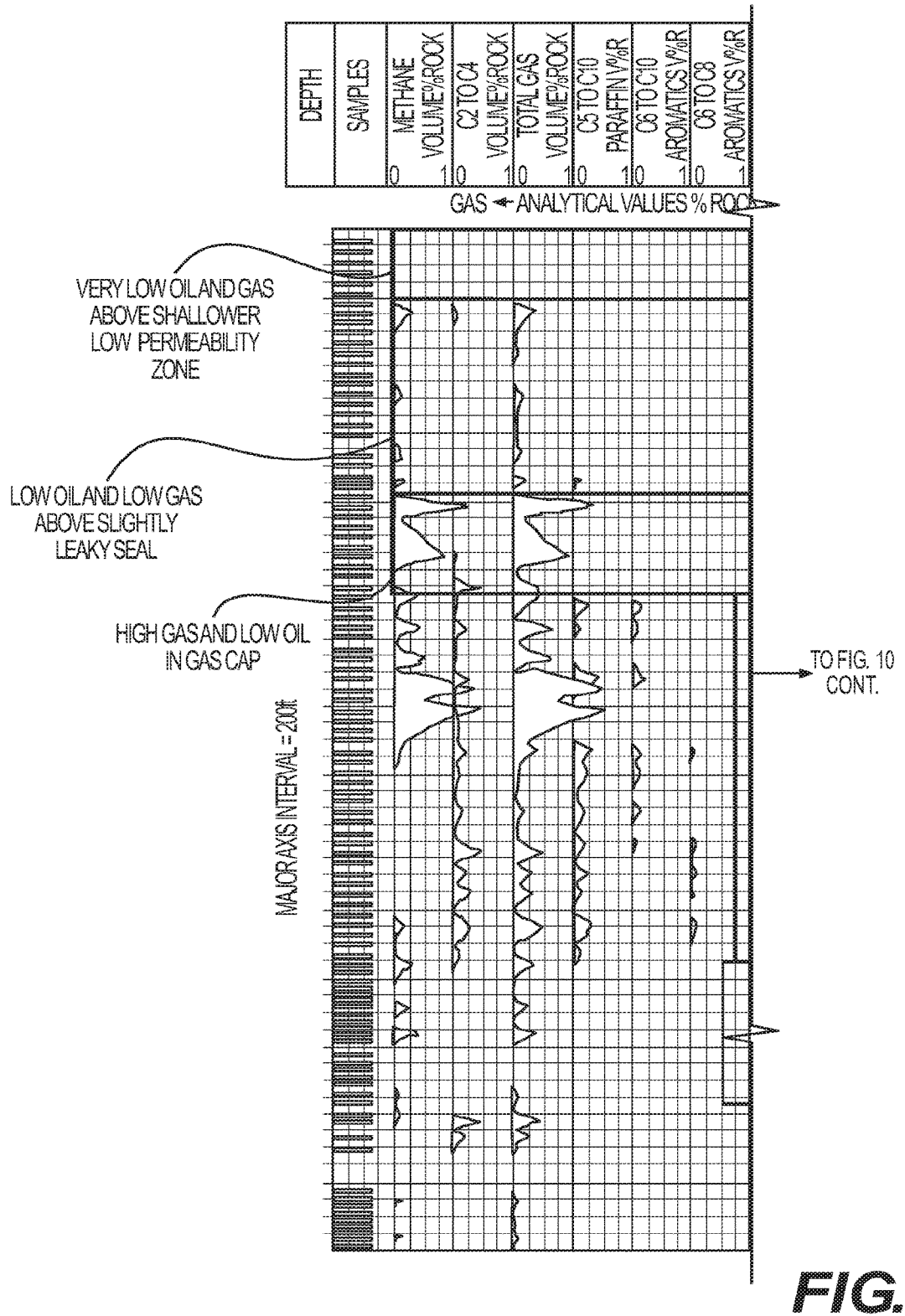
FIG. 10 is another plot of data obtained using methods of the invention including hydrocarbon data, oil saturated water, and other data elements used to identify and characterize deposits within a geologic formation at different depths.
Figure 10:
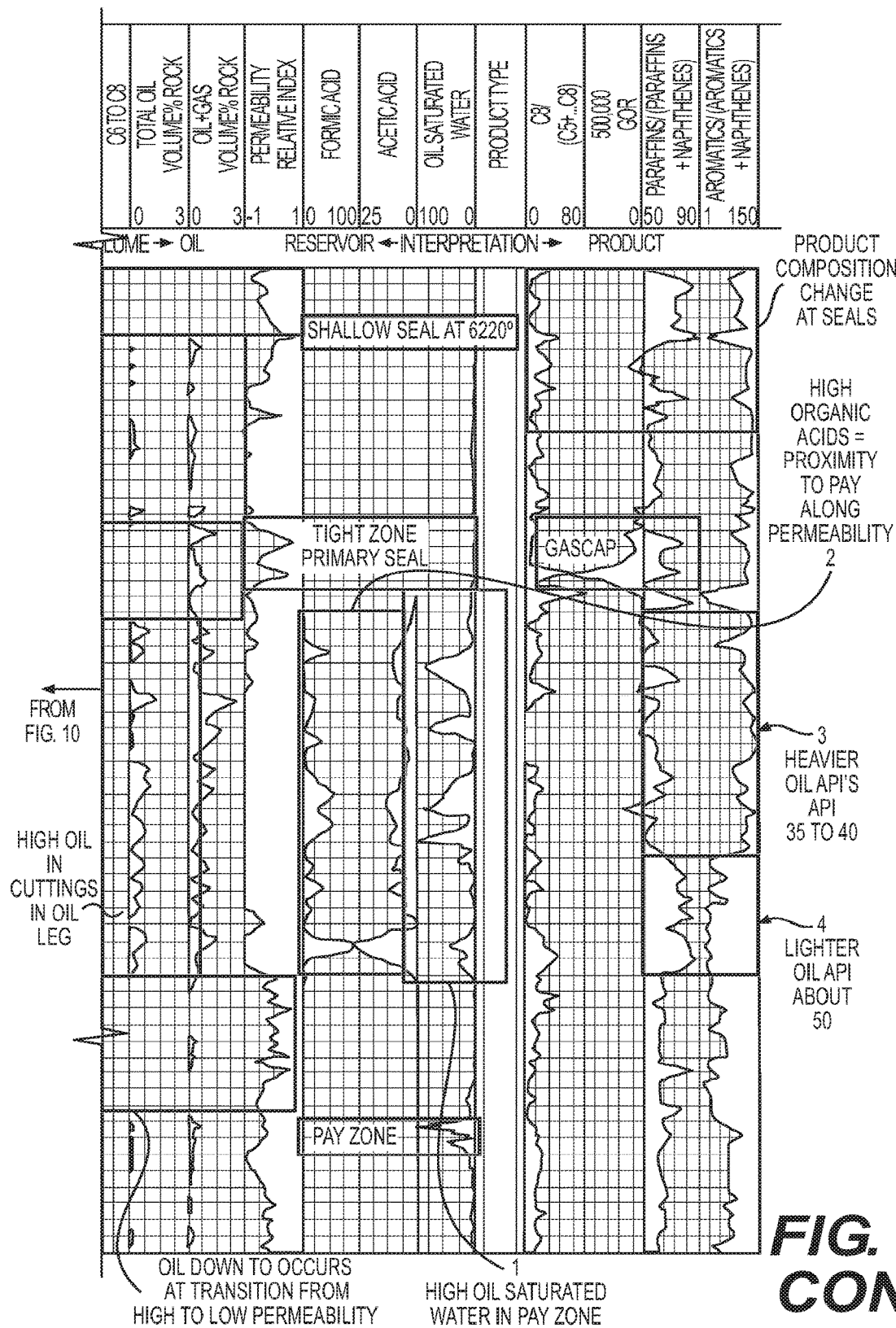

The well depicted in FIG. 10 was drilled for a deeper target and there was no effort expended in searching for pay zones in the shallower part of the well depicted in FIG. 10. However, analyses of samples shown in FIG. 10 revealed a 600-foot oil column that was indicated by high oil saturated water #1 and high formic and acetic acids #2. As discussed above, in unconventional reservoirs having very low permeability, one or more proximity to pay indicators, e.g., formic and acetic acids, can delineate the pay zone in as much as the water and oil coexist in the same strata in an unconventional reservoir, and do not separate out into discrete oil pay zones versus water legs as happens in much more permeable conventional reservoir settings.

The 600-foot oil column detected by oil saturated water #1 and organic acids #2 is actually two oil accumulations that are juxtaposed one on top of the other. Analysis of the data allows for discrimination of these two oils as having different chemical compositions using the paraffins/(paraffins+naphthenes) and the aromatics/(aromatics+naphthenes) curves #3, with relatively low values for both these ratios in the upper 400 feet of the pay zone #3 that was identified defined using oil saturated water #1, and organic acids #2. However, data #4 shows high values for both of these ratios for the deepest 200 feet of this pay zone. The data indicate to those skilled in the art that the oil in upper zone #3 is heavier than the oil in the lower zone #4. This is somewhat unusual if this were a conventional oil and gas reservoir system, as in those systems oil and gas become stratified by gravity according to density, that is to say in conventional reservoirs petroleum is usually stratified with the lighter petroleum above the heavier petroleum. This, however, is not a trend that has particular relevance in unconventional reservoirs with vanishingly small permeabilities. In this case, the data obtained by the inventive method indicates that the #3 reservoir is a tight carbonate into which oil and gas have migrated into from some source rock that is spatially removed from the reservoir. Reservoir #4 in contrast is an organic-rich shale that is both the source for the oil it holds, and the reservoir for the oil. Unconventional oil from source rocks tends to be lighter than migrated oil. Migrated oil tends to lose lighter hydrocarbons during expulsion from the source rock, i.e., primary migration, and transport to the reservoir, i.e., secondary migration, and during the residence of the petroleum in the reservoir. As tight shales can be both source and reservoir, the oil in tight shales does not lose its more volatile components during migration and while being in the reservoir, and hence is usually lighter than conventional oil. Hence it is reasonable to conclude that the overlying oil #3 in a tight limestone is heavier than the underlying oil in a tight organic-rich shale.

From a production point of view reservoir #3 and reservoir #4 will need to be produced as separate reservoirs. Reservoirs #3 and #4 are not in communication. They will produce different types of oil. And various aspects of the reservoir, such as fluid pressure, will be different. This reflects an advantageous element of the invention in identifying and characterizing separated pay zones of separate characteristics.

Figure 10A:
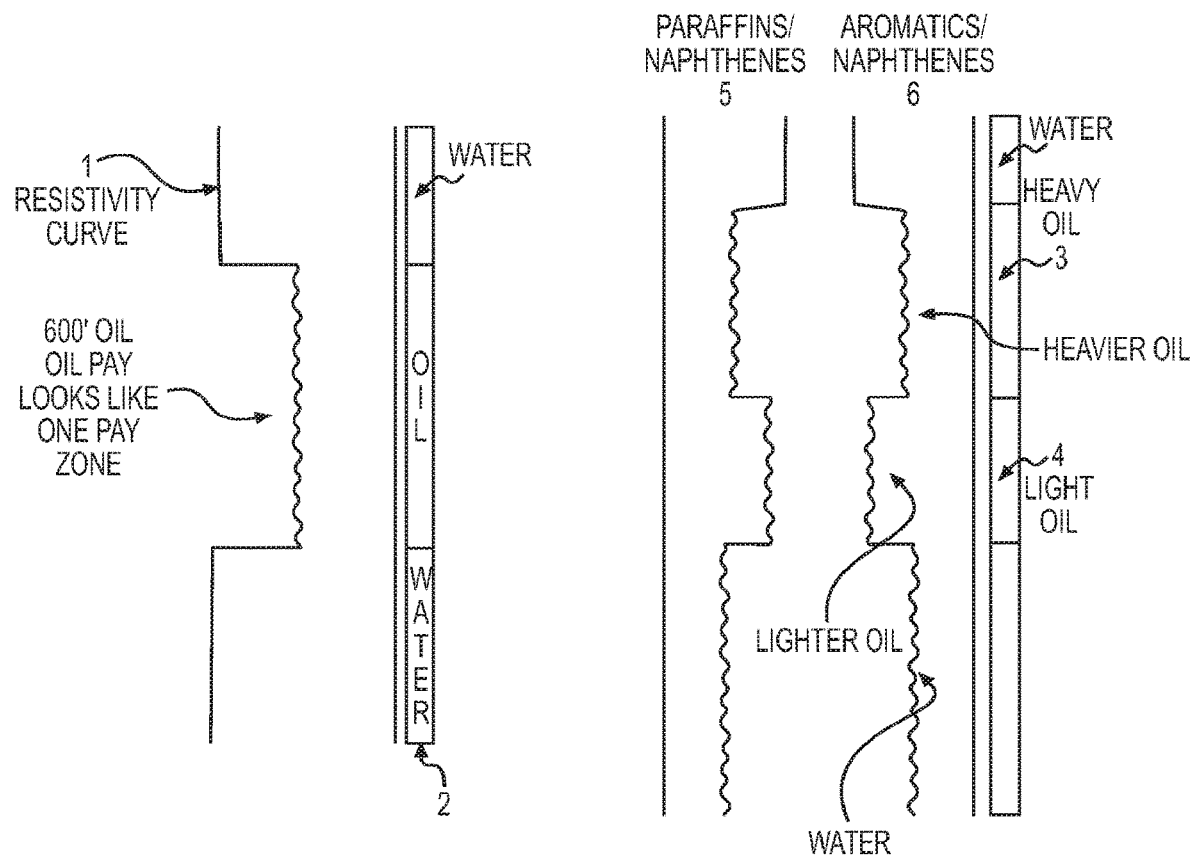
FIG. 10A is a simplified representation of key data patterns in FIG. 10.

FIG. 10A illustrates other aspects of this Example. Curve #1 on the left is the resistivity curve that indicates a 600-foot oil column overlain and underlain by water, as shown by the product type log #2. The 600-foot oil column #1 is shown to be divided into a 400-foot-thick upper heavier oil reservoir and a deeper 200-foot-thick lighter oil reservoir #4. The distinction between shallow heavy oil reservoir #3 and deeper lighter oil reservoir #4 is based on the paraffins/naphthenes ratio curve #5 and the aromatics/naphthenes ratio curve #6.

The results of this analysis demonstrate that methods of the invention as exemplified here can identify two separate oil pay zones, and further demonstrate that the cutting analysis methods of the invention can be used to distinguish between different types of oil pay zones in a well site, which might otherwise be confused with one another based on other methods of analysis.

Example 11

Methods of the invention can be performed to demonstrate different oil pay zones at a site due to the presence of different profiles of hydrocarbons present in the respective sites. In this respect, the methods of the invention could be used to identify compartmentalized and discrete oil pay zone sites. A reflection of this concept is provided in FIG. 11.

Figure 11:
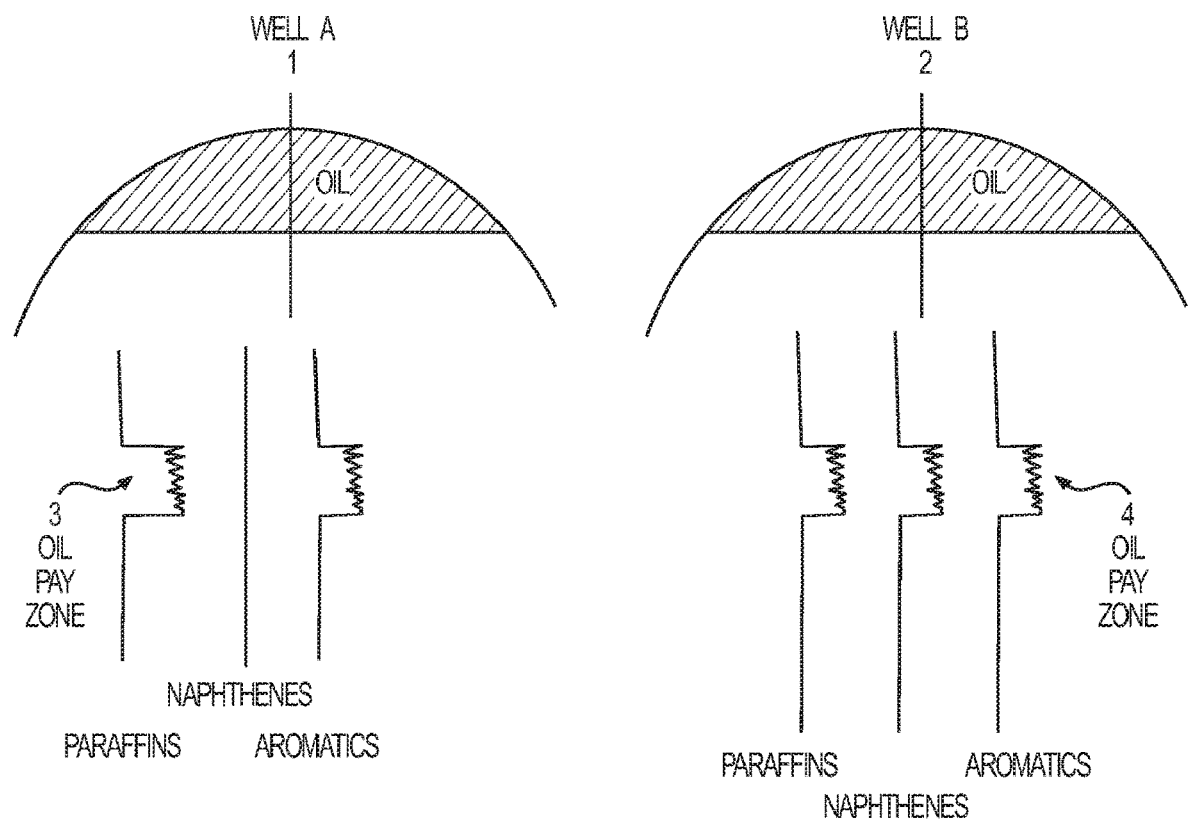
FIG. 11 provides a representation of two data sets for different formations/sites that can be differentially analyzed by methods of the invention.

As shown in FIG. 11, Well A #1 and Well B #2 are both oil wells drilled in similar geologic situations. The oil pay zone in Well A #3 is oil comprised of high paraffins and aromatics content, but low naphthenes content. The oil pay zone in Well B #4 contains oil comprised of high paraffins and aromatics content, but also high naphthenes content. The oil in reservoir #3 will have a different character from the oil in reservoir #4. Documenting the difference using data obtained by the inventive methods described herein will then allow those trained in the art of oil exploration to consider various scenarios to account for this observed difference. Also, the knowledge that two different oils occurring in one area reduces exploration risk in that area as the probability of finding oil is increased if there is more than one oil source that can charge reservoirs in the area being explored.

Example 12

This Example provides an illustration of a method for the measurement of many of the above-described parameters associated with a sample for characterizing a material in a well site device according to certain aspects of the invention, where the inventive method involving the use of the device occurs while the well is drilling at such a rate so that the data are obtained as quickly as possible so that that data can be used to help "steer" the well in a close to "real time" manner (it is expected that there may often be a "lag" of about 10-100, such as about 20-60 feet, from the location of the active drill and the latest location of data analysis, simply given the logistics of well operations, such as limitations of what can be placed at a drill bit, interfering noise and motion, etc.). Aspects of the invention such as the device and method envisioned here can be advantageous for the optimum placement of lateral wells, also known as horizontal wells.

Figure 12:
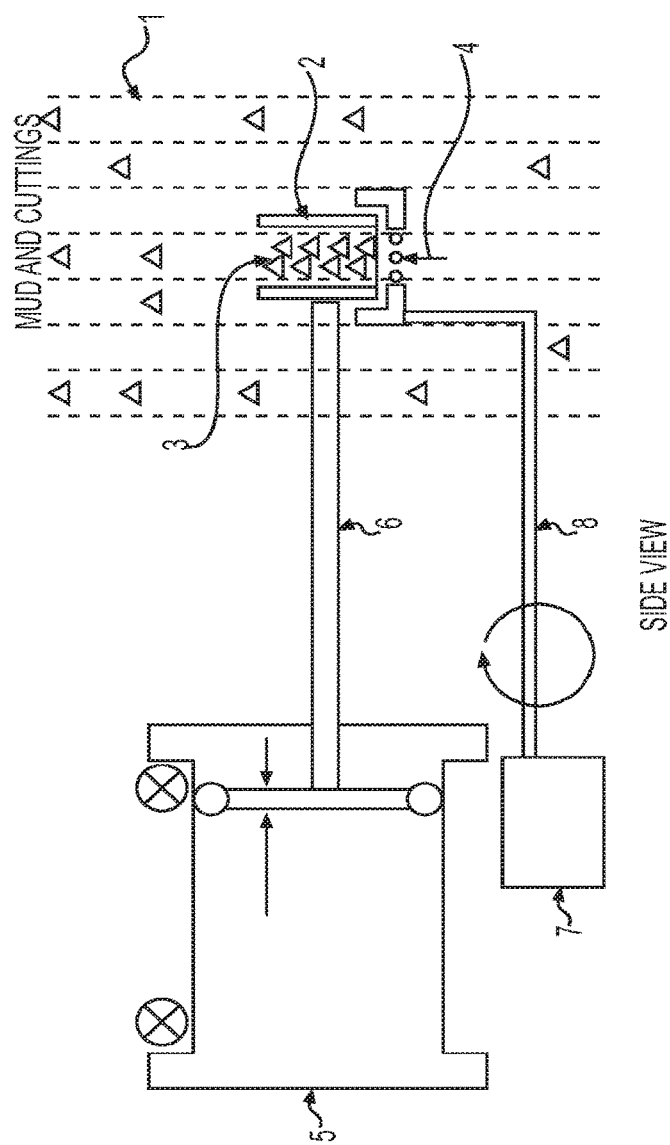
FIG. 12 provides an illustration of a well site device for frackability/compression analysis of cuttings allowing for real time/near real time steering of a lateral well.
Figure 12:
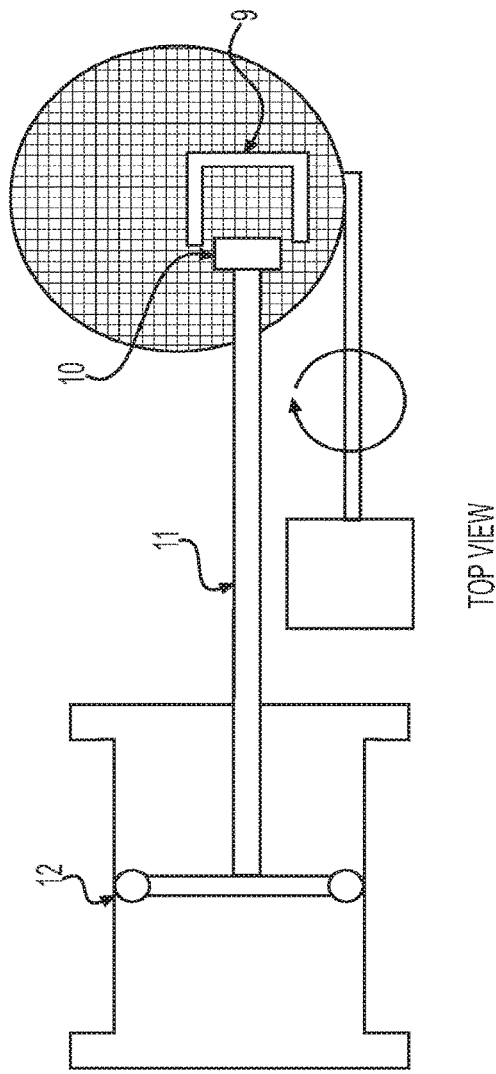

A device for a rapid method for determining frackability on the well site is depicted in FIG. 12. With reference to the device of FIG. 12, #1 depicts the discharge of mud and cuttings from the flow line and into the possum belly of a conventional oil well. A reusable collapsible container, #2, is positioned so that a portion of the mud and cuttings discharge must flow through it. A screen, #4, is placed at the bottom of reusable collapsible container, #2, that allows drilling mud to escape the reusable collapsible container #2, but retains the cuttings #3 inside the container. An air piston, #5, is situated outside of the mud and cuttings discharge #1. The air piston #5 transmits unidirectional force for crushing the cuttings #3 through the elongate rod #6. A rotating device, #7, usually driven by air pressure rotates the screen #4 using rod #8 away from the collapsible container #2 to discharge material from the cuttings #3 after they have been crushed. The screen #4 is retracted from the reusable collapsible container #2 for a sufficient amount of time to allow the now crushed cuttings #3 to be removed from the reusable collapsible chamber #2 to be cleansed from the chamber by the vigorous flow of mud and cuttings #1. The device #7 could be another air piston that moves the screen laterally out from under reusable collapsible container #2 instead of a rotating device.

The top view shows the reusable collapsible container #2 is comprised of two parts. Part #9 is U-shaped in cross section having two right angle corners. The fourth wall of the reusable collapsible container is a plate #10 that has no solid connection with part #9 of the container. Upon filling of the reusable collapsible container #9 and #2 with cuttings #3 from the flow line mud and cuttings discharge #1, the cuttings are crushed by activating air piston #1 to squeeze them through transmitting a force through rod #11 to the plate #10. The frackability of the cuttings is determined by measuring and recording how much the rod #11 has been extended out from the air piston #12. The speed and fluidity of motion of the crushing of the cuttings #3 can also be recorded, as can any recovery of the crushing assembly upon release of force on air piston #12. These parameters can aid in a more complete description of the mechanical properties of the cuttings, including Poisson's Ratio, and Young's modulus. These parameters, along with frackability, can be important and useful in steering a lateral to stay in the rocks of optimum mechanical strength, and in determining the best manner in which to complete the lateral through the fracking and production stages of oil production.

LIST OF ILLUSTRATIVE ASPECTS OF THE INVENTION

The following is a non-limiting list of certain aspects of the invention that can provide additional assistance and guidance in understanding the unique features and advantages that the invention provides.

The first set of aspects relates to methods in which multiple aliquots are obtained from a sample and the volatile substances in such aliquots analyzed:

In aspects, the invention provides a method for analyzing volatile substances in a material comprising: (a) providing an analyzable sample of a material, (b) subjecting the sample to one or more forces to release a first gas containing an analyzable amount of one or more volatile substances, (c) trapping and concentrating the first gas in or with a media in an analyzable amount to generate an aliquot, (d) isolating the aliquot from the sample, (e) releasing volatile substances from the aliquot as released gasses in a predictable sequence, (f) analyzing the volatile substance chemistry of at least one of the volatile substances to obtain an analysis of the aliquot, (g) performing at least one more cycle of analysis comprising repeating steps (b)-(f) of the method, at least one additional time, wherein for each repetition the specific force applied is distinct from the force previously applied to the sample, and (h) analyzing all of the analyses to provide information about the material (aspect 1).

In aspects, the invention provides the method of aspect 1, wherein the one or more forces comprises subjecting the sample to a specific pressure without mechanical disruption, e.g., crushing (aspect 2).

In aspects, the invention provides the method of aspect 2, wherein the sample is initially subjected to the specific pressure at which it was sealed in its container so as no unsealed volatiles are lost. This is usually performed at about 1-100 millibars, such 2-80 millibars, e.g., about 3-75 millibars (aspect 3).

In aspects, the invention provides the method of any one of aspects 1-3, wherein the sample is subjected to the specific pressure and temperature at which it was initially obtained (aspect 4).

In aspects, the invention provides the method of aspect 4, wherein the method comprises subjecting the sample to different pressures, without mechanical disruption (aspect 5).

In aspects, the invention provides the method of any one of aspects 1-5, wherein the analysis of the volatile substance chemistry comprises subjecting the volatile substances to mass spectrometry (aspect 6).

In aspects, the invention provides the method of any one of aspects 1-6, wherein the analysis provides information concerning the quantity of one or more volatile compounds in the material (aspect 7).

In aspects, the invention provides the method of any one of aspects 1-7, wherein step h of the method (the analysis step) comprises comparing at least some of the analyses against one or more standards (aspect 8).

In aspects, the invention provides the method of any one of aspects 1-8, wherein the force comprises dehydrating the sample prior to crushing, applying mechanical pressure on the sample, mechanically rupturing some or all of the sample, subjecting the sample to a chemical reaction, or a combination of any thereof (aspect 9).

In aspects, the invention provides the method of any one of aspects 1-9, wherein the method further comprises subjecting the sample to two or more different pressures, optionally to generate two or more aliquots (aspect 10).

In aspects, the invention provides the method of any one of aspects 1-10, wherein the volatile substances comprise C1-C20 hydrocarbons (aspect 11).

In aspects, the invention provides the method of any one of aspects 1-11, wherein the step of trapping comprises subjecting the gas to a non-selective trap (aspect 12).

In aspects, the invention provides the method of any one of aspects 1-12, wherein the step of trapping comprises cryogenic capture of the gas (aspect 13).

In aspects, the invention provides the method of aspect 13, wherein the trapping step comprises subjecting the gas to temperatures of less than about −50 degrees C. (aspect 14).

In aspects, the invention provides the method of aspect 14, wherein the method comprises contacting the gas to a material cooled by contact with liquid nitrogen (aspect 15).

In aspects, the invention provides the method of any one of aspects 1-15, wherein the volatile substances comprise C1-C10 hydrocarbons (aspect 16).

In aspects, the invention provides the method of any one of aspects 3-16, wherein the pressure is either ambient atmospheric, pressure positive pressure in excess of ambient atmospheric pressure, or a level of vacuum below atmospheric pressure but greater than $3 \times 10^{-4}$ millibars (aspect 17).

In aspects, the invention provides the method of aspect 17, wherein the pressures applied to the sample are greater than $1 \times 10^{-3}$ millibars (aspect 18).

In aspects, the invention provides the method of aspect 18, wherein the pressures applied to the sample are greater than $25 \times 10^{-3}$ millibars (aspect 19).

In aspects, the invention provides the method of aspect 19, wherein the pressures applied to the sample are greater than $1 \times 10^{-2}$ millibars (aspect 20).

In aspects, the invention provides the method of any one of aspects 3-20, wherein the method comprises subjecting the sample to a pressure of between 1-100 millibars (aspect 21).

In aspects, the invention provides the method of any one of aspects 1-21, wherein the sample is a rock that comprises no recent fluid inclusions that could have trapped recent fluids such as present day oil and/or gas (aspect 22).

In aspects, the invention provides the method of aspect 22, wherein the sample has not experienced significant burial diagenesis (aspect 23).

In aspects, the invention provides the method of any one of aspects 1-23, wherein the method comprises removing potentially interfering gasses from contact with the media prior to analyzing gasses released from the aliquot (aspect 24).

In aspects, the invention provides the method of aspect 24, wherein the interfering gasses removed comprise oxygen, nitrogen, or both oxygen and nitrogen (aspect 25).

In aspects, the invention provides the method of aspect 25, wherein the method comprises purging oxygen and nitrogen from contact with the media by contact with an inert gas that does not chemically react with the sample and does not cause any interferences with the chemical analyses of the samples' volatiles (aspect 26).

In aspects, the invention provides the method of aspect 26, wherein the inert gas is an inert gas, such as argon or nitrogen (aspect 27).

In aspects, the invention provides the method of any one of aspects 1-27, wherein more than 50% of the volatile substances in the sample are analyzed by the method (aspect 28).

In aspects, the invention provides the method of aspect 28, wherein more than 75% of the volatile substances in the sample are analyzed by the method (aspect 29).

In aspects, the invention provides the method of aspect 30, wherein more than 90% of the volatile substances in the sample are analyzed by the method (aspect 30).

In aspects, the invention provides the method of aspect 30, wherein more than 99% of the volatile substances in the sample are analyzed (aspect 31).

In aspects, the invention provides the method of any one of aspects 1-31, wherein the first gas is allowed to contact the media for 0.1 seconds to 10 minutes (aspect 32).

In aspects, the invention provides the method of any one of aspects 1-32, wherein the first gas is allowed to contact the media for about 10 minutes or longer (aspect 33).

In aspects, the invention provides the method of aspect 33, wherein the first gas is allowed to contact the media for about 20 minutes or longer (aspect 34).

In aspects, the invention provides the method of aspect 34, wherein the first gas is allowed to contact the media for about 40 minutes or longer (aspect 35).

In aspects, the invention provides the method of any one of aspects 1-35, wherein the method does not comprise heating the sample to temperatures greater than 100° C. (aspect 36).

In aspects, the invention provides the method of aspect 36, wherein the method does not comprise heating the sample to temperatures greater than 60° C. (aspect 37).

In aspects, the invention provides the method of any one of aspects 1-37, wherein the method comprises collecting a portion of the first gas of at least one of the cycles that will not bind to the media as a separate non-condensable gas and subjecting this non-condensable gas aliquot to a separate analysis (aspect 38).

In aspects, the invention provides the method of aspect 38, wherein the media is a cooled surface to which the first gas condenses and at least some of the portion will not condense on the cooled surface (aspect 39).

In aspects, the invention provides the method of aspect 38 or aspect 39, wherein the method comprises isolating the non-condensable gas from the condensable gasses to facilitate separate analysis thereof (aspect 40).

In aspects, the invention provides the method of any one of aspects 38-40, wherein the portion of the non-condensable gas comprises methane, helium, hydrogen, or a combination of some or all thereof (aspect 41).

In aspects, the invention provides the method any one of aspects 38-41, wherein the portion of the non-condensable gas comprise neon, argon, krypton, or a combination of two or more of these gasses (aspect 42).

In aspects, the invention provides the method of any one of aspects 1-42, wherein the method comprises containing the sample in a container which isolates the sample from the environment in a manner that substantially retains volatile substances in the sample from the time the sample is placed in the container until release of the first gas (aspect 43).

In aspects, the invention provides the method of aspect 43, wherein the container comprises a seal that can be selectively punctured to release the first gas allowing gaseous contents of the container to flow into contact with the media when punctured (aspect 44).

In aspects, the invention provides the method of aspect 43, wherein the container comprises a puncture-free connector system (aspect 45).

In aspects, the invention provides the method of any one of aspects 1-45, wherein the method comprises collecting the first gas under each different condition for at least about 1 minute to form each aliquot (aspect 46).

In aspects, the invention provides the method of any one of aspects 1-46, wherein the method comprises the step of substantially removing one or more potentially interfering gasses before trapping the first gas (aspect 47).

In aspects, the invention provides the method of aspect 47, wherein the step of removing potentially interfering gasses is completed in about 3 seconds or less (aspect 48).

In aspects, the invention provides the method of aspect 47 or aspect 48, wherein the potentially interfering gasses comprise oxygen, nitrogen, carbon dioxide, or a combination thereof (aspect 49).

In aspects, the invention provides the method of aspect 47 or aspect 49, wherein the method comprises purging the potentially interfering gas from contact with the media by filling the area surrounding the media with a purging gas, such as a non-condensable gas (aspect 50).

In aspects, the invention provides the method of aspect 50, wherein the purging gas is argon or krypton (aspect 51).

In aspects, the invention provides the method of any one of aspects 1-51, wherein the media is a cooled surface (aspect 52).

In aspects, the invention provides the method of aspect 52, wherein the surface is cooled by indirect contact with liquid nitrogen, or another cryogenic liquid such as liquid argon, liquid oxygen, or liquid helium (aspect 53).

In aspects, the invention provides the method of any one of aspects 1-53, wherein the method comprises performing an optional analysis at atmospheric pressure and at least two analyses at different pressures both of which are below atmospheric pressure (aspect 54).

In aspects, the invention provides the method of any one of aspects 1-54, wherein the method does not comprise performing gas chromatographic analysis (aspect 55).

In aspects, the invention provides the method of any one of aspects 1-55, wherein the method comprises evaluating the permeability of the sample by assessing differences in the aliquots obtained by extraction under two different sets of conditions (aspect 56).

The following listing of aspects of the invention is directed to a method of the invention comprising extracting and analyzing only a single aliquot of material:

In aspects, the invention provides a method for analyzing volatile substances in a material comprising: (a) providing an analyzable sample of a material, (b) subjecting the sample to one or more forces to release a first gas containing an analyzable amount of one or more volatile substances, (c) trapping and concentrating the first trappable gas (such as a condensable gas in a system that relies on condensation of the gas) in or with a media in an analyzable amount to generate an aliquot, (d) isolating the aliquot from the sample, (e) releasing volatile substances from the aliquot as released gasses in a predictable sequence, and (f) analyzing the volatile substance chemistry of at least one of the volatile substances to obtain an analysis of the aliquot (aspect 57).

In aspects, the invention provides the method of aspect 57, wherein the method comprises only forming and analyzing a single aliquot, which may comprise two or more sub-aliquots (aspect 58).

In aspects, the invention provides the method of aspect 58, wherein the single aliquot comprises a condensable gas component that is trapped with a first trap and a non-condensable gas component that is separately collected (aspect 59).

In aspects, the invention provides the method of any one of aspects 57-59, wherein the method comprises subjecting the sample to at least one pressure of at least 1 millibar and less than 1 atmosphere (aspect 60).

In aspects, the invention provides the method of aspect 60, wherein the method comprises subjecting the sample to a pressure of about 1 millibar to about 100 millibars (aspect 61).

In aspects, the invention provides the method of any one of aspects 57-61, wherein the sample is subjected to vacuum pressure for a period of about 0.25 minutes to about 15 minutes (aspect 62).

In aspects, the invention provides the method of any one of aspects 57-62, wherein the one or more forces comprises subjecting the sample to a crushing force in addition to one or more other forces such as vacuum pressure, vibrational energy, or radiation energy, such as laser excitation, or a combination of any or all thereof (aspect 63).

In aspects, the invention provides the method of any one of aspects 57-63, wherein the analysis of the volatile substance chemistry comprises subjecting the volatile substances to mass spectrometry or other method of analysis (aspect 64).

In aspects, the invention provides the method of any one of aspects 57-63, wherein the step of trapping comprises cryogenic capture of condensable gas and optionally capturing a sub-aliquot of non-condensable gas in a separate manner for separate analysis (aspect 65).

In aspects, the invention provides the method of any one of aspects 57-65, wherein the method comprises removing potentially interfering gasses from contact with the media prior to analyzing gasses released from the aliquot (aspect 66).

In aspects, the invention provides the method of any one of aspects 57-66, wherein the method does not comprise heating the sample to temperatures greater than 100° C. (aspect 67).

In aspects, the invention provides the method of any one of aspects 57-67, wherein the method comprises measuring the ductility of the sample by providing the sample in a crushable container and determining the size of the impact of the crushing force on the container and sample (aspect 68).

In aspects, the invention provides the method of any one of aspects 57-68, wherein the method comprises collecting and sealing samples at the wells versus loaded in lab samples (aspect 69).

In aspects, the invention provides the method of any one of aspects 57-69, wherein the method comprises collecting and analyzing samples in close proximity to the well site (aspect 70).

In aspects, the invention provides the method of any one of aspects 57-70, wherein the method comprises collecting and analyzing samples inside a well, such as a well that is under active drilling (aspect 71).

In aspects, the invention provides the method of aspect 71, wherein the method comprises real-time or near real-time analysis of samples, for example where the lag time between the site of drilling and the analysis of samples is less than about 50 feet, such as less than about 40 feet, less than about 30 feet, less than about 20 feet, or less than about 10 feet, 7 feet, 5 feet, or even less than about 1 foot (aspect 72).

In aspects, the invention provides the method of any one of aspects 57-72, wherein the method comprises measuring the amount of acetic acid, formic acid, and/or oil saturated water associated with the sample (aspect 73).

In aspects, the invention provides the method of any one of aspects 57-73, wherein the method comprises measuring the amount of methane, carbon dioxide, and/or carbon monoxide that is released from the trap (aspect 74).

In aspects, the invention provides the method of aspect 74, wherein the method comprises measuring the amount of carbon monoxide that is released from the trap (aspect 75).

In aspects, the invention provides the method of any one of aspects 57-75, wherein one or more steps of the method are performed in close proximity to a petroleum well site (aspect 76).

In aspects, the invention provides the method of aspect 76, wherein the method is performed within about 150 feet of the site of drilling (aspect 77).

In aspects, the invention provides the method of aspect 77, wherein the method comprises pneumatic delivery of samples to a laboratory for analysis (aspect 78).

In aspects, the invention provides the method of aspect 78, wherein the method comprises analysis in real-time while the well is drilling and the data is used to steer the well to keep the borehole in or as close as possible to the target pay zone (aspect 79).

In general, the aspects that are dependent on aspect 57 can apply to the method of aspect 1. The aspects that are dependent on aspect 1 can be applied to aspect 57. In fact, aspect 1 can be considered to depend from aspect 57. Any of these methods reflected in aspects 1-79 can comprise developing a standard and/or adjusting for conditions at a location (e.g., calculating carbon monoxide located at a location and subtracting it from a measured amount, or applying a similar approach to formic acid, acetic acid, and/or oil saturated water).

The following set of aspects is directed to a method focused on primarily assessing ductility (frackability) of a material by performance of a method of the invention:

In aspects, the invention provides the method for analyzing the ductility or hardness of the geologic formation comprising: (a) providing an analyzable sample of a material, (b) subjecting the sample to one or more forces that are capable of compressing material of a given hardness or ductility, and (c) determining the amount of compression of the sample (aspect 80).

In aspects, the invention provides the method of aspect 80, wherein the method comprises compressing multiple sides of the sample contemporaneously (aspect 81).

In aspects, the invention provides the method of aspect 81, wherein the method comprises isotopically compressing the sample (aspect 82).

In aspects, the invention provides the method of aspect 80-82, wherein the sample is obtained from a petroleum well (aspect 83).

In aspects, the invention provides the method of aspect 83, wherein the sample is selected from a cutting and a core sample (aspect 84).

In aspects, the invention provides the method of aspect 84, wherein the sample is a cutting (aspect 85).

In aspects, the invention provides the method of any one of aspects 80-85, wherein the method is performed on multiple samples from a site (aspect 86).

In aspects, the invention provides the method of aspect 86, wherein the samples comprise samples obtained from different depths of a material wherein the depths range from about 0.5 feet to about 100 feet (aspect 87).

In aspects, the invention provides the method of aspect 86 or aspect 87, wherein the samples comprise materials obtained from the same or approximately the same zone of depth but from locations that are separated by about 0.5 feet to 100 feet (aspect 88).

In aspects, the invention provides the method of any one of aspects 86-88, wherein the method comprises analyzing at least 10 samples from different depths (aspect 89).

In aspects, the invention provides the method of any one of aspects 86-89, wherein the method comprises analyzing at least 10 samples from the same zone of depth (aspect 90).

In aspects, the invention provides the method of any one of aspects 86-90, wherein the method comprises analyzing about 10 to about 2,500 samples (aspect 91).

In aspects, the invention provides the method of any one of aspects 80-91, wherein the method comprises combining the results of the method with the results of mineralogic analysis of the sample, other samples, or the material, x-ray diffraction of the samples, other samples or the material; x-ray fluorescence of the samples, other samples, or the material; a total organic content measurement associated with the samples, other samples, or the material, and/or combination with other data such as photography and/or spectroscopy of the samples or other samples or the material by any suitable means in any wavelength, and/or chemical, geochemical, or material testing of the samples, related samples, or the material, or a combination of any or all thereof (aspect 92).

The following set of aspects are directed to a device of the invention for the analysis of oil saturation and/or water saturation from samples:

In aspects, the invention provides a device comprising: (a) a chamber for receiving and isolating samples of a material; and (b) a detection component capable of detecting the amount of one or more target volatile substances released from the sample, wherein the substances comprise carbon monoxide, acetic acid, formic acid, or a combination thereof, optionally in combination with hydrocarbons, inorganic gasses, or a combination thereof (aspect 93).

In aspects, the invention provides the device of aspect 93, wherein the device comprises an energy input component that promotes the release of volatile substances from the sample (aspect 94).

In aspects, the invention provides the device of aspect 94, wherein the energy input component is (a) a pressure generating device or system, (b) a device or system that promotes release of volatile substances through mechanical forces, thermal forces, or both, or a combination of (a) and (b) (aspect 95).

In aspects, the invention provides the device of any one of aspects 93-95, wherein the device comprises a system or component for isolating volatile substances released from the sample (aspect 96).

In aspects, the invention provides the device of any one of aspects 93-96, wherein the device comprises a trap for collection and release of volatile substances (aspect 97).

In aspects, the invention provides the device of aspect 97, wherein the trap comprises a non-selective trap, such as a trap that comprises a liquid nitrogen trap (aspect 98).

In aspects, the invention provides the device of any one of aspects 93-98, wherein the device comprises a mass spectrometer (aspect 99).

In aspects, the invention provides the device of any one of aspects 93-99, wherein the device comprises a component or device for selectively isolating the mass spectrometer from the sample (aspect 100).

In aspects, the invention provides the device of aspect 100, wherein the device comprises a volatile substance trap and the method comprises a component or device for selectively isolating the volatile substance trap from the sample, the mass spectrometer, or both (aspect 101).

In aspects, the invention provides the device of any one of aspects 93-101, wherein the device is part of a system that comprises a mechanism for determining the compressibility of the sample (aspect 102).

The following set of aspects are directed to another type of device provided by the invention:

In aspects, the invention provides a device for chemical analysis comprising: (a) a cryogenic trap, (b) a cooling component for selectively cooling the cryogenic trap, (c) a warming component for selectively warming the cryogenic trap, and (d) an analytical device comprising a mass spectrometer for analyzing one or more volatile substance released from the cryogenic trap (aspect 103).

In aspects, the invention provides the device of aspect 103, wherein the warming component is operable in a manner that provides for controlled warming of the cryogenic trap to promote separate release of two or more amounts of volatile substances from the cryogenic trap (aspect 104).

In aspects, the invention provides the device of aspect 103 or aspect 104, wherein the device further comprises a vacuum that can promote the release of volatile substances from a material in communication with the device, wherein at least one of the volatile substances can be trapped on the trap (aspect 105).

In aspects, the invention provides the device of any one of aspects 103-105, wherein the device comprises one or more housing components that keep at least an analyzable proportion of the volatile substances captured by the trap separate from the environment (aspect 106).

In aspects, the invention provides the device of any one of aspects 103-106, wherein the device further comprises a component for promoting the flow of substances through the device, such as one or more selectively operable pumps (aspect 107).

In aspects, the invention provides the device of any one of aspects 103-107, wherein the device comprises a component or system for capturing one or more substances that do not bind to the cryogenic trap and for separately analyzing such one or more non-binding substances (aspect 108).

In aspects, the invention provides the device of any one of aspects 103-108, wherein the device comprises components for delivering a cryogenic substance selected from the group consisting of liquid nitrogen, liquid argon, liquid oxygen, liquid air, liquid helium, dry ice, a dry ice slurry, normal ice, a normal ice slurry of water ice in fresh water, a normal ice slurry of water ice in a saline brine, or any other naturally cooling substance capable of achieving the minimum temperature required to freeze the substance(s) of interest onto the cryogenic trap (aspect 109).

In aspects, the invention provides the device of any one of aspects 103-109, where the cryogenic state of the trap is at least partially achieved, and the device comprises components for mechanical refrigeration or cooling, as may be achieved with, e.g., a Kelvinator device. The Kelvinator or other cryogenic device must be able to achieve the minimum temperature required to freeze the substance(s) of interest onto the cryogenic trap (aspect 110).

In aspects, the invention provides the device of any one of aspects 103-110, where the device further comprises an additional mass spectrometer, a gas chromatograph; an infrared spectrometer; a Raman spectrometer; or any combination of these analytical devices (aspect 111).

In another aspect of the invention, the methods, systems, and devices described above further comprise components for or steps for determining the permeability of a sample, through application of two different forces, such as two different pressures, to each sample analyzed for permeability, and analyzing the difference in the release of one or more substances or substance classes, such as hexanes, upon the application of the different forces. Any one of the above described 111 aspects can be further modified by addition of such step or the inclusion of settings or components for practicing such steps.

Incorporation by Reference and Interpretation

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for analyzing substances in a non-gaseous material comprising:
   (1) providing an analyzable amount of a non-gaseous material;
   (2) applying force to the material causing the release of a first gas from the material, the first gas released from the material containing an analyzable amount of a substance, wherein the force comprises exposing the material to a vacuum at a negative pressure of $1\times10^{-5}$ millibars or more;
   (3) trapping and concentrating a trappable portion of the first gas in or with a cryogenic trap in an analyzable amount to generate a trapped gas aliquot:
   (4) isolating the trapped gas aliquot from the material;
   (5) releasing a portion of the trapped gas aliquot to form a released gas aliquot;
   (6) analyzing the chemistry of the released gas aliquot through mass spectrometry to obtain an analysis of the substance in the trapped gas aliquot; and
   (7) repeating steps (2)-(6) of the method for at least one additional cycle, wherein step (2) is applied to the same material in the initial performance of the method and each additional cycle, the force applied to the material in at least a first cycle of the cycles comprising the initial performance of the method and each additional cycle is different from the force applied to the material in at least a second cycle of the cycles thereby causing the release of a different first gas in the first cycle from the first gas released in the second cycle and wherein the first gas of the first cycle and first gas of the second cycle are trapped, isolated, released, and analyzed separately from one another.

2. The method of claim 1, wherein the material is collected from a geological site.

3. The method of claim 2, wherein the material is a petroleum drill cutting or a core sample.

4. The method of claim 3, wherein the material is collected from a petroleum well drilled within the geologic site and wherein the method comprises placing the material in a sealable container within about 5 minutes or less of collection of the material sealing the sealable container, and maintaining the material in a sealed state until the force is applied to the sample.

5. The method of claim 1, wherein the method further comprises collecting a second, non-condensable portion of the first gas that does not bind to the cryogenic trap, and separately analyzing the chemistry of the second, non-condensable portion of the first gas as a second non-condensable gas aliquot.

6. The method of claim 5, wherein the method further comprises (1) placing the material in a sample container, the sample container being capable of containing gas and being selectively puncturable to allow for the selective release of gas contained therein, at least part of the sample container being capable of being deformed without releasing any gas contained in the sample container when a mechanical force is applied to the sample container and (2) applying a mechanical force to disrupt the sample container and the material prior to or during application of the force that causes the release of gas.

7. The method of claim 5, wherein the material is a sample of a geologic site and the results of the method provide an indication of the amount of oil, natural gas, or both contained in the geologic site.

8. The method of claim 7, wherein the method is performed on at least 20 sample containers, each of the at least 20 sample containers containing a sample of material that is obtained from an area of a petroleum well, wherein the material that each sample is obtained from is separated from the areas that each of the other samples is obtained from by at least 20 vertical feet, at least 0.75 horizontal feet, or both.

9. The method of claim 1, wherein the force comprises exposing the material to a vacuum at a negative pressure of $1\times10^{-4}$ millibars or more.

10. The method of claim 1, wherein the force comprises exposing the material to a vacuum at a negative pressure of $1\times10^{-3}$ millibars or more.

11. The method of claim 1, wherein step (3) of the method comprises trapping and concentrating the trappable portion of the first gas with a cryogenic trap and step (6) of the method comprises analyzing the chemistry of the released gas by a mass spectrometer.

12. The method of claim 11, wherein the cryogenic trap and the mass spectrometer are contained in a closed system, wherein the closed system comprises a flow path comprising sections, wherein each section is selectively separable from one another and comprises an interior that is configured to contain gas and an exterior that is impermeable to external gas, and the method further comprises (A) purging gas from at least a portion of the closed system by application of a vacuum, (B) filling the closed system with a gas that does not condense on the cryogenic trap, or both (A) and (B).

13. The method of claim 1, wherein the method comprises applying two or more forces and the method comprises two or more cycles.

* * * * *